(12) United States Patent
Nikolskaya et al.

(10) Patent No.: US 8,000,949 B2
(45) Date of Patent: *Aug. 16, 2011

(54) METHODS FOR IDENTIFICATION OF NOVEL PROTEIN DRUG TARGETS AND BIOMARKERS UTILIZING FUNCTIONAL NETWORKS

(75) Inventors: Tatiana Nikolskaya, Portage, IN (US); Andrej Bugrim, St. Joseph, MI (US); Yuri Nikolsky, Portage, IN (US)

(73) Assignee: Genego, Inc., Saint Joseph, MI (US)

( * ) Notice: Subject to any disclaimer, the term of this patent is extended or adjusted under 35 U.S.C. 154(b) by 1266 days.

This patent is subject to a terminal disclaimer.

(21) Appl. No.: 11/499,437

(22) Filed: Aug. 4, 2006

(65) Prior Publication Data

US 2007/0038385 A1 Feb. 15, 2007

Related U.S. Application Data

(63) Continuation-in-part of application No. 10/518,103, filed on Oct. 14, 2005, which is a continuation-in-part of application No. 10/174,762, filed on Jun. 18, 2002.

(60) Provisional application No. 60/299,040, filed on Jun. 18, 2001.

(51) Int. Cl.
G06G 7/48 (2006.01)
(52) U.S. Cl. .......................................... 703/11
(58) Field of Classification Search ........................ None
See application file for complete search history.

(56) References Cited

U.S. PATENT DOCUMENTS

| 2002/0159625 | A1 | 10/2002 | Elling |
| 2003/0224363 | A1 | 12/2003 | Park et al. |
| 2003/0233218 | A1* | 12/2003 | Schilling ........................ 703/11 |
| 2006/0235624 | A1 | 10/2006 | Nikolskaya et al. |

FOREIGN PATENT DOCUMENTS

| WO | WO-00/50889 | 8/2000 |
| WO | WO 01/13105 | * 2/2001 |

OTHER PUBLICATIONS

Forst et al. (Journal of Computational Biology vol. 6, Nos. 3/4, 1999, pp. 343-360).*
Takai-Igarashi et al. (In Silico Biology, vol. 1, p. 129-146, 1999).*
Ishizuka et al.(Information processing society of Japan, vol. 91, p. 73-80, Sep. 27, 2000).*
Boot et al., Arterioscler Thromb Vasc Biol. (1999) 19(3):687-694.
Chajara et al., Atherosclerosis (1996) 125(2):193-207.
ERGO System Database, website retrieval online at <http://igweb.integratedgenomics.com/IGwit/.
Haase and Bartold, J. Periodontol. (2001) 72(3):341-348.
Hovingh and Linker, J. Biol. Chem. (1970) 245:6170-6175 (EC No. 4.2.2.7).
Johansen et al., Exp Opin Ther Targets (2007) 11(2):219-234.
Karp et al., Trends in Biotechnology (1999) 17:275-281.
KEGG table of contents as of Feb. 1999, retrieved online at <http://web.archive.org/web/19990203053246/www.genome.ad.jp/kegg/kegg2.html>.
Khan et al., Electrophoresis (1999) 20(2):223-229.
Kirkpatrick et al., Gene (1995) 153(2):147-154.
Kuffner et al., Bioinformatics (2000) 16(9):825-836.
Kupsch et al., Nervenarzt (1991) 62:80-91.
Kuroda et al., J. Dermatol. Sci. (2001) 26(2):156-160.
Lindvall, Europ. Neurol. (1991) 31(Suppl. 1):17-27.
Lark et al., Fed Proc. (1985) 44(2):394-403.
Luke and Prehm, Biochem. J. (1999) 343(Pt. 1):71-75.
Mookerjea, Can J. Biochem. (1978) 56(7):746-752.
Nakao et al., Genome Informatics (1999) 10:94-103.
NCBI Online Database, Accesion Nos. AAE10146-AAE10153.
NCBI Online Database, Accession Nos. AAE13758-AAE13770.
NCBI Online Database, Accession Nos. AAE67749-AAE67785.
Neuger et al., Atherosclerosis (2001) 157(1):13-21.
Okubo et al., Nature Genetics (1992) 2:173-179.
Osawa et al., Cells Tissues Organs (2000) 167(1):9-17.
Papakonstantinou et al., Atherosclerosis (1998) 138(1):79-89.
Papakonstantinou et al., PNAS USA (1995) 92(21):9881-9885.
Permyakov and Savel'Ev, Zh Nevrol Psikhiatr Im S S Korsakova (1998) 98(2):59-61.
Recklies et al., Biochem. J. (2001) 354(Pt. 1):17-24.
Saveliev et al., Int J. Biol. (1997) 41(6):801-808.
Schaefer et al., J. Cell Sci. (1996) 109(Pt. 2):479-488.
Scharnagl et al., Lab Invest. (1999) 79(10):1271-1286.
Selkov et al., Gene (1997) 197:GC11-26.
Selkov et al., PNAS USA (2000) 97(7):3509-3514.
Semino et al., PNAS USA (1996) 93(10):4548-4553.
Shackelton et al., J. Biol. Chem. (1995) 270(22):13076-13083.
Shyjan et al., J. Biol. Chem. (1996) 271(38):23395-23399.
Stanley et al., J. Biol. Chem. (1995) 270(10):5077-5083.
Tile D4 of the Boerhinger Biochemical pathways map, Roche Applied Science, 1993, retrieved online at <http://www.expasy.org/cgi-bin/show_image?D4&up>.
U.S. Appl. No. 60/299,040, filed Jun. 18, 2001.
Vellacott and Balfour, Br. Med J. (1978) 2(6138):699.
Volker et al., J. Histochem. Cytochem. (1991) 39(10):1385-1394.
Watanabe and Yamaguchi, J. Biol. Chem. (1996) 271(38):22945-22948.
Zimmermann et al., (Biochim. Biophys. Acta (2000) 1484(2-3):316-324.
Covert, Trends in Biochemical Sciences (2001) 26(3):179-186.
Notice of Rejection for Japanese Patent Application No. 2004-514229, mailed on Jun. 23, 2009, 3 pages.
GOLD Database, retrieved online at http://wit.integratedgenomics.com/GOLD/, date retrieved on May 23, 2008.

* cited by examiner

*Primary Examiner* — Karlheinz R Skowronek
(74) *Attorney, Agent, or Firm* — Morrison & Foerster LLP

(57) ABSTRACT

The process of System Reconstruction is used to integrate sequence data, clinical data, experimental data, and literature into functional models of disease pathways. System Reconstruction models serve as informational skeletons for integrating various types of high-throughput data. The present invention provides the first metabolic reconstruction study of a eukaryotic organism based solely on expressed sequence tag (EST) data. System Reconstruction also provides a method for the identification of novel therapeutic targets and biomarkers using network analysis. The initial seed networks are built from the lists of novel targets for diseases with the high-throughput experimental data being superimposed on the seed networks to identify specific targets.

9 Claims, 75 Drawing Sheets

Figure 12A

Example of an enzyme page: Methionine adenosyltransferase
EC 2.5.1.6 Methionine adenosyltransferase

| Names |
|---|
| Adenosylmethionine synthetase |
| Adenosyltransferase, methionine |
| AdoMet synthetase |
| ATP:L-methionine S-adenosyltransferase |
| ATP:L-methionine-S-adenosyltransferase |
| ATP-methionine adenosyltransferase |
| EC 2.4.2.13 (formerly) |
| Methionine adenosyltransferase |
| Methionine S-adenosyltransferase |
| Methionine-activating enzyme |
| S-Adenosyl-L-methionine synthetase |
| S-Adenosylmethionine synthase |
| S-Adenosylmethionine synthetase |

Human genes assigned:

| Symbol | Name | SwissProt | UniGene |
|---|---|---|---|
| MAT1A | methionine adenosyltransferase I, alpha | Q00266 | Hs.323715 |
| MAT2A | methionine adenosyltransferase II, alpha (catalytic) | P31153 | Hs.77502 |
| MAT2B | methionine adenosyltransferase II, beta (non-catalytic) | | Hs.54842 |

NEXT >

Figure 12B

Methionine adenosyltransferase page, continued
EC 2.5.1.6 Methionine adenosyltransferase

| Names |
|---|
| Adenosylmethionine synthetase |
| Adenosyltransferase, methionine |

Human genes assigned:

| Symbol | Name | SwissProt | UniGene |
|---|---|---|---|
| MAT1A | methionine adenosyltransferase I, alpha | Q00266 | Hs.323715 |
| MAT2A | methionine adenosyltransferase II, alpha (catalytic) | P31153 | Hs.77502 |
| MAT2B | methionine adenosyltransferase II, beta (non-catalytic) | | Hs.54642 |

Click on gene symbols to view gene pages

Pathways & Reactions

| Reactions |
|---|
| (Cytosol) L-methionine + H₂O + ATP = 'S' adenosyl-L-methionine + phosphate + pyrophosphate |

| Pathways |
|---|
| L-methionine/L-serine/pyrophosphate/2-oxobutanoate/adenosine/L-cysteine/cyt |

Click here to view reaction page

Annotations
1

| Diseases: | hypermethioninemia (methionine adenosyltransferase deficiency), cancer, carcinoma |
|---|---|
| Note | |
| PMID | 11145114, 2345265, 8871179, 10921051, 10955733, 10677294 |
| Tissue/Cells | Plasma, Kidney, Erythrocytes, Chronic lymphocytic leukemia cells, Liver, Breast cancer cell lines, Colon, N/A |

NEXT >

Figure 13

Reaction page

(Cytosol) L-methionine + H₂O + ATP = 'S' adenosyl-L-methionine + phosphate + pyrophosphate

| Location | Cytosol |
|---|---|
| Catalyst | 2.5.1.6 |
| Cofs | |
| Revers | No |

| Chem | Src | CoenzType |
|---|---|---|
| pyrophosphate | -1 | |
| ATP | 1 | |
| H(,2)O | -1 | |
| L-methionine | -1 | donor |
| phosphate | 1 | |
| 'S'-adenosyl-L-methionine | 1 | |

Annotations

1

| Diseases | hypermethioninemia (methionine adenosyltransferase deficiency) |
|---|---|
| Note | |
| PMID | 6871179,11145114,2345265 |
| Tissue/Cells | Erythrocytes, Kidney |

2

| Diseases | cirrhosis |
|---|---|
| Note | Catalytically active human and rat liver S-adenosylmethionine synthetase exists mainly in tetramer and dim form. In liver biopsy samples from cirrhotic patients a marked reduction in total S-adenosylmethionine synthetase activity and a specific loss of the tetrameric form of the enzyme exist. Because treatment of S-adenosylmethionine synthetase with N-ethylmaleimide resembles the situation of this enzyme in cirrhotic patients, it is proposed that impaired protection of the enzyme from oxidizing agents caused by a decreased synthesis of glutathione can explain the diminished synthesis of S-adenosylmethionine in liver cirrhosis. |
| PMID | 2307400 |
| Tissue/Cells | Liver |

Figure 14

Gene page
Gene MAT2A

| Symbols | MAT2A SAMS2 MAT II |
|---|---|
| Location | 02 p11.2 |
| Names | methionine adenosyltransferase II, alpha (catalytic) |
| OMIM | 601468 |
| Enzyme | 2.5.1.6 |
| GDB | 136213 |
| SwissProt | P31153 |
| UniGene | Hs.77502 |
| Sequences | BC001686 BC001854 X68836 |

Expressed in
adrenal_gland; amnion_normal; b-cells; bladder; blood; bone; bone marrow; brain; breast; breast_normal; cervix; cns; colon; colon_ins; colon_normal; connective tissue; dermis; drash; ear; epid_tumor; esophagus; eye; foreskin; germ cell; head_neck; head_normal; heart; kidney; islamics; liver; fung; lymph; marrow; muscle; nervous_normal; nervous_tumor; ovary; pancreas; parathyroid; placenta; pool; prostate; prostate_normal; prostate_tumor; skin; skin, normal; 4 pooled samples; small intestine; stomach; stomach_normal; testis; cell line; tonsil; uterus; uterus_tumor; whole embryo

Amino Acid Sequence
INGQLNGFHEAFIEEGTFLFTSESVGEGHPDKICDQISDAVLDAHLQQDPDAKVACETVAKTGMILLAGEITSRAAVDYQKVVREAV Number of ESTs from different organs/tissues (fetal ESTs and those without explicit organ/tissue data are excluded)

| Liver | Brain | Kidney | Heart | Lung | Total |
|---|---|---|---|---|---|
| 2 | 35 | 30 | 14 | 52 | 445 |
| 0% | 7% | 6% | 3% | 11% | 100% |

Figure 15

| Compound page | |
|---|---|
| S-adenosyl-L-methionine | |
| | Annotations |
| | 1 |
| Diseases | |
| Diseases note | |
| Note | S-adenosyl-L-methionine (SAMe): a molecule naturally present in several body tissues and fluids, is produced, by SAMe synthetase, from ATP and methionine. SAMe has a fundamental role, as methyl group donor, in transmethylation reactions in which the synthesis of membrane phospholipids is mandatory for the maintenance of membrane fluidity. Another metabolic pathway involving SAMe, transsulphuration, is initiated with the release of -CH3 from the molecule and the formation of S-Adenosyl-homocysteine and then homocysteine and cysteine, a precursor of glutathione the main cellular antioxidant, responsible of detoxification of various compounds and xenobiotics. |
| PMID | 1299337 |
| Tissue/Cells | liver |

Figure 17

Disease page: atherosclerosis
DISEASE : atherosclerosis

Pathways

L-histidine/histamine//cyt
L-methionine/L-serine/pyrophosphate/2-oxobutanoate/adenosine/L-cysteine//cyt

Enzymes

4.1.1.22
4.2.1.22

Reactions

(Cytosol) L-homocysteine + L-serine = L-cystathionine + H₂O
(Cytosol) L-histidine = histamine + CO₂

Annotations

1

Diseases atherosclerosis
Homocystinuria due to cystathionine beta-synthase (CS) deficiency is the most common inborn error of Click on links to view pathways, enzymes and reactions associated with a disease

Figure 20

Parkinson disease page

Annotations

| | | |
|---|---|---|
| 1 | | |
| Diseases | Parkinson disease, Parkinson disease, association with, idiopathic parkinsonism. | |
| Note | | |
| PMID | 1683212, 8989461, 10619718, 3099860, 11058194, 8825899, 34555, 35409926, 8965384, 10843794, 6441736, 1041; | |
| 2 | | |
| Diseases | Parkinson disease | |
| Note | The increase in platelet MAO-B activity and decrease in plasma PEA concentrations in patients with Parkinson's disease may be involved in the pathophysiological processes of the disease, and these changes are reversed by treatment with selegiline. | |
| PMID | 11160474 | |
| 3 | | |
| Diseases | Parkinson disease | |
| Note | AAAD is the second enzyme in the sequence leading to the synthesis of the catecholamines and serotonin, and it is the rate-limiting enzyme for the synthesis of the trace amines. In the striatum AAAD activity is increased by neuronal firing and diminished or enhanced by activation or blocking dopamine (DA) D1 or D2 receptors, respectively. A1 least two biochemical mechanisms appear responsible for modulation, short-term involving second messengers and possible phosphorylation, and long-term involving protein synthesis. In Parkinson's disease AAAD is the rate-controlling enzyme for the synthesis of DA when L-DOPA is administered and any change of AAAD activity could have clinical consequences. | |
| PMID | 8584878 | |

Figure 25A

3-phospho-D-glycerate/L-glutamate//2-oxoglutarate/L-serine//c)
View > scheme

Reactions
1.1.1.95 (Cytosol) 3-phospho-D-glycerate + NAD+ = 3-phosphohydroxypyruvate + NADH
2.6.1.52 (Cytosol) 3-phosphohydroxypyruvate + L-glutamate = 'O'-phospho-L-serine + 2-oxoglutarate
3.1.3.3 (Cytosol) 'O'-phospho-L-serine + H$_2$O = L-serine + phosphate

Enzymes

| EC number | Genes | Expressed in | ESTs |
|---|---|---|---|
| 1.1.1.95 | PHGDH | adrenal gland; aorta; b-cells; bladder; blood; bodo_tumor; bone; bone marrow; brain; breast; breast_normal; cervix; cns; colon; colon_est; colon_ins; colon_normal; esophagus; eye; fetal brain; foreskin; germ cell; head_neck; heart; kidney; kidney_tumor; liver; lung; lung_tumor; lymph; marrow; muscle; muscle (skeletal); nervous_normal; nervous_tumor; nose; ovary; pancreas; parathyroid; placenta; placenta_normal; pnet; pool; pooled; pooled colon, kidney, stomach; pooled pancreas and spleen; prostate; prostate_normal; skin; small intestine; synovial membrane; testis; testis, cell line; thymus, pooled; tissue culture; tonsil; uterus; uterus_tumor; whole embryo | AA021612 AA046094 AA08-AA093706 AA093721 AA10 AA101580 AA113268 AA11: AA114165 AA114201 AA12i AA128452 AA134085 AA13> AA137039 AA143014 AA14; AA146617 AA147630...(tots 1145) |
| 2.6.1.52 | PSA | adrenal gland; aorta; blood; bone; bone marrow; brain; breast; cervix; cns; colon; colon_est; colon_ins; colon_normal; denis_drash; ear; eye; fetal brain; foreskin; genitourinary tract; germ cell; head_neck; heart; kidney; leiomios; lung; tung, cell line; lymph; muscle; nervous_tumor; normal head/neck tissue; ovary; pancreas; placenta; placenta_normal; pool; pooled; prostate; skin; spleen; stomach; testis; testis, cell line; testis_normal; thymus, pooled; tonsil; uterus; whole embryo | AA025924 AA057399 AA07i AA094923 AA085029 AA12· AA134792 AA137152 AA173 AA173916 AA176173 AA16· AA192412 AA192463 AA18i AA224436 AA224501 AA25; AA307911 AA316484 ...(tots 467) |
| 3.1.3.3 | PSPH | adrenal gland; aorta; bone; bone marrow; brain; cervix; colon; colon_est; eye; kidney; liver; lung; muscle (skeletal); nervous_tumor; pancreas; placenta; pool; pooled lung and spleen; prostate; stomach; thyroid; whole embryo | AA488432 AA488571 AA621 AI370863 AI479788 AL5251J AL526979 AL527020 AL528( AL529170 AL562450 AL5631 AL563371 AU118817 AU124 AU143636 AU148622 AU160327 AU160599 AW029526 ...(total 86) |

Annotations
1
Diseases: carcinoma, Fanconi anemia, Williams-Beuren syndrome (WS; WBS; MIM:194050), Alzheimer disease (MIM:104300)
Note
PMID

Diseases 3-phosphoglycerate dehydrogenase deficiency

Note 3-Phosphoglycerate dehydrogenase (3-PGDH) deficiency is an inborn error of serine biosynthesis. Patients are affected with congenital microcephaly, psychomotor retardation, and intractable seizures effects of oral treatment with amino acids were investigated in 2 siblings. L-Serine up to 500 mg/kg/ was not sufficient for seizure control. Addition of glycine 200 mg/kg/day resulted in complete disappearance of seizures. Electroencephalographic abnormalities gradually resolved after 6 months. conclude that 3-PGDH can be treated effectively by a combination of L-serine and glycine.

PMID 8758134,9708551

3

Diseases

Note In particular in tissues with a high rate of cell turnover, phosphoserine aminotransferase and serine hydroxymethyltransferase activities were coordinately increased (6089514).

PMID 6089514

4

Diseases cancer susceptibility, prostate and brain,carcinoma,leukemia,lymphoma

Note The nucleotide sequence of Hs 3-PGDH gene, encoding human 3-phosphoglycerate dehydrogenase th catalyzes the initiating step in the phosphorylated pathway of serine biosynthesis, has been determine The 3-PGDH gene has a predicted 533 amino acid open reading frame, encoding a 56.8kDa protein th shares 94.0% similarity with rat-liver 3-PGDH. Two different transcripts corresponding to 3-PGDH mRNA were detected in human normal tissues. A dominant 2.1kb transcript was expressed at high le\ in prostate, testis, ovary, brain, liver, kidney, and pancreas, and weakly expressed in thymus, colon, an heart. A 710bp transcript also appeared as a weaker band where the 2.1kb mRNA was expressed, and was more significant than the 2.1kb mRNA in heart and skeletal muscle. The TPA-induced monocytic differentiation of U937, which also resulted in growth arrest, abruptly downregulated the expression o PGDH. Removal of TPA restored cell growth through the retrodifferentiation process and subsequent expression of 3-PGDH. The 3-PGDH mRNA was markedly expressed in human leukemias, lymphom: Sup-T1, colon adenocarcinoma COLO 320DM, epithelioid carcinoma HeLa S3, and murine lymphoma BW5147.G.1.4, but not in human leukemia K562. This report demonstrates that the human 3-PGDH g is regulated at the transcriptional level depending on tissue specificity and cellular proliferative status, i its transcriptional regulation mechanism may be a useful target for diagnosis and therapy of cancer (10713460).

PMID 10713460

Tissue/Cells

| | | | |
|---|---|---|---|
| Brain | Cerebrospinal fluid | Colon | Endometrium |
| Fibroblasts | Kidney | Liver | Lymphoblasts |
| Lymphocytes | Ovary | Pancreas | Prostate |
| Testis | | | |

Figure 26

(Cytosol) 3-phospho-D-glycerate + NAD$^+$ = 3-phosphohydroxypyruvate + NADH

Location Cytosol
Catalyst 1.1.1.95
Cofs
Revers No

| Chem | StC | | CoenzType |
|---|---|---|---|
| 3-phospho-D-glycerate | 1 | | |
| NADH | -1 | | donor |
| NAD(+) | 1 | | acceptor |
| 3-phosphohydroxypyruvate | -1 | | |

Annotations

Figure 27A

EC 1.1.1.95 Phosphoglycerate dehydrogenase

Names

3-Phosphoglycerate dehydrogenase
3-Phosphoglycerate:NAD+ 2-oxidoreductase
3-Phosphoglyceric acid dehydrogenase
alpha-Phosphoglycerate dehydrogenase
D-3-Phosphoglycerate dehydrogenase
D-3-Phosphoglycerate:NAD oxidoreductase
Dehydrogenase, phosphoglycerate
Glycerate 3-phosphate dehydrogenase
Glycerate-1,3-phosphate dehydrogenase
Phosphoglycerate dehydrogenase
Phosphoglycerate oxidoreductase
Phosphoglyceric acid dehydrogenase

Human genes assigned:

| Symbol | Name | SwissProt | UniGene |
|---|---|---|---|
| PHGDH | 3-phosphoglycerate dehydrogenase | O43175 | Hs.3343 |

Pathways & Reactions

Reactions

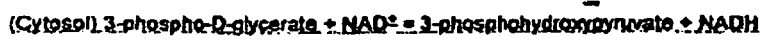
(Cytosol) 3-phospho-D-glycerate + NAD⁺ = 3-phosphohydroxypyruvate + NADH

Pathways
3-phospho-D-glycerate/L-glutamate//2-oxoglutarate/L-serine//cyt

Annotations

1
Diseases  3-phosphoglycerate dehydrogenase deficiency, carcinoma
Note
PMID  3126791
Tissue/Cells Colon

Figure 27B

EC 1.1.1.95 Phosphoglycerate dehydrogenase    Pag

Diseases  3-phosphoglycerate dehydrogenase deficiency

Note  3-Phosphoglycerate dehydrogenase (3-PGDH) deficiency is an inborn error of serine biosynthesis. Patients affected with congenital microcephaly, psychomotor retardation, and intractable seizures. The effects of oral treatment with amino acids were investigated in 2 siblings. L-Serine up to 500 mg/kg/day was not sufficient seizure control. Addition of glycine 200 mg/kg/day resulted in complete disappearance of seizures. Electroencephalographic abnormalities gradually resolved after 6 months. We conclude that 3-PGDH can b treated effectively by a combination of L-serine and glycine.

PMID  8758134,9708551

Tissue/Cells N/A

3

Diseases  cancer susceptibility, prostate and brain, carcinoma, leukemia, lymphoma

Note  The nucleotide sequence of Hs 3-PGDH gene, encoding human 3-phosphoglycerate dehydrogenase that catalyzes the initiating step in the phosphorylated pathway of serine biosynthesis, has been determined. The PGDH gene has a predicted 533 amino acid open reading frame, encoding a 56.8kDa protein that shares 9« similarity with rat-liver 3-PGDH. Two different transcripts corresponding to 3-PGDH mRNA were detected in human normal tissues. A dominant 2.1kb transcript was expressed at high levels in prostate, testis, ovary, b liver, kidney, and pancreas, and weakly expressed in thymus, colon, and heart. A 710bp transcript also appe as a weaker band where the 2.1kb mRNA was expressed, and it was more significant than the 2.1kb mRNA heart and skeletal muscle. The TPA-induced monocytic differentiation of U937, which also resulted in growth arrest, abruptly downregulated the expression of 3-PGDH. Removal of TPA restored cell growth through the retrodifferentiation process and subsequent expression of 3-PGDH. The 3-PGDH mRNA was markedly expressed in human leukemias, lymphoma Süp-T1, colon adenocarcinoma COLO 320DM, epithelioid carcinc HeLa S3, and murine lymphoma BW5147.G.1.4, but not in human leukemia K562. This report demonstrates the human 3-PGDH gene is regulated at the transcriptional level depending on tissue specificity and cellular proliferative status, and its transcriptional regulation mechanism may be a useful target for diagnosis and the of cancer (10713460).

PMID  10713460

Tissue/Cells Prostate, Testis, Liver, Ovary, Brain, Pancreas, Kidney

Figure 28

(Cytosol) 3-phosphohydroxypyruvate + L-glutamate = 'O'-phospho-L-serine + 2-oxoglutarate Location Cytosol
Catalyst 2.6.1.52
Cofa
Revers No

| Chem | SIC | CoenzType |
|---|---|---|
| 'O'-phospho-L-serine | -1 | |
| 2-oxoglutarate | -1 | |
| L-glutamate | 1 | |
| 3-phosphohydroxypyruvate | 1 | |

Annotations

EC 2.6.1.52 Phosphoserine transaminase

Names

3-Phosphoserine aminotransferase
Aminotransferase, phosphoserine
Hydroxypyruvic phosphate-glutamic transaminase
L-Phosphoserine aminotransferase
O-Phospho-L-serine:2-oxoglutarate aminotransferase
Phosphohydroxypyruvate transaminase
Phosphohydroxypyruvic-glutamic transaminase
Phosphoserine aminotransferase
Phosphoserine transaminase
PSAT

Human genes assigned:

| Symbol | Name | SwissProt | UniGene |
|---|---|---|---|
| PSA | phosphoserine aminotransferase | Q9Y617 | Hs.286049 |

Pathways & Reactions

Reactions

(Cytosol) 3-phosphohydroxypyruvate + L-glutamate ⇌ O-phospho-L-serine + 2-oxoglutarate

Pathways

3-phospho-D-glycerate/L-glutamate//2-oxoglutarate/L-serine//cyt

Annotations

1
Diseases
Note
PMID 6089514,2682527
Tissue/Cells Lymphocytes,Endometrium

2
Diseases
Note   In particular in tissues with a high rate of cell turnover, phosphoserine aminotransferase and serine hydroxymethyltransferase activities were coordinately increased (6089514).
PMID 6089514
Tissue/Cells N/A

Figure 30

(Cytosol) 'O'-phospho-L-serine + $H_2O$ = L-serine + phosphate

Location Cytosol
Catalyst 3.1.3.3
Cofe
Revers No

| Chem | StC | CoenzType |
|---|---|---|
| H(,2)O | 1 | |
| 'O'-phospho-L-serine | 1 | |
| L-serine | -1 | |
| phosphate | -1 | |

Annotations

EC 3.1.3.3 phosphoserine phosphatase

Names

3-phosphoserine phosphatase
O-phosphoserine phosphohydrolase
phosphatase, phosphoserine
phosphoserine phosphatase
PSP
PSPase

Human genes assigned:

| Symbol | Name | SwissProt | UniGene |
|---|---|---|---|
| PSPH | phosphoserine phosphatase | P78330 | Hs.56407 |

Pathways & Reactions

Reactions

(Cytosol) 'O'-phospho-L-serine + $H_2O$ = L-serine + phosphate

Pathways

3-phospho-D-glycerate/L-glutamate//2-oxoglutarate/L-serine//cyt

Figure 32

Gene PSPH

Symbols PSPH PSP
Location 07 p21-15
Names phosphoserine phosphatase
OMIM 172480
Enzyme 3.1.3.3
GDB 120322
SwissProt P78330
UniGene Hs.56407
Sequences Y10275

Expressed in adrenal gland; aorta; bone; bone marrow; brain; cervix; colon; colon_est; eye; kidney; liver; lung; muscle (skeletal); nervous_tumor; pancreas; placenta; pool; pooled lung and spleen; prostate; stomach; thyroid; whole embryo

Amino Acid Sequence

MISHSELRKLFYSADAVCFDVDSTVIREEGIDELAKICGVEDAVSEMTRRAMGGAVPFKAALTERLALIQPSREQVQRLIAEQP

Number of ESTs from different organs/tissues (fetal ESTs and those without explicit organ/tissue data are exclude

| Liver | Brain | Kidney | Heart | Lung | Total |
|-------|-------|--------|-------|------|-------|
| 2     | 24    | 2      | 0     | 4    | 61    |
| 3%    | 39%   | 3%     | 0%    | 6%   | 100%  |

Expressed sequence tags (ESTs)

(20 out of 90) ... view full list
AA488432  AA468571  AA621925  AI370893  AI479788  AL525152  AL528979  AL527020  AL528007  AL52917
AL562450  AL583029  AL583371  AU118817  AU124836  AU143638  AU148822  AU160327  AU160699  AW0295

Figure 33A

SWISS-PROT: P78330

| ExPASy Home page | Site Map | Search ExPASy | Contact us | SWISS-PRC |

| Hosted by NCSC US | Mirror sites: | Australia | Canada | China | Korea | Switzerland | Taiwan |

SWISS-PROT: P78330

*NiceProt - a user-friendly view of this SWISS-PROT entry*

```
ID   SERB_HUMAN      STANDARD;      PRT;   225 AA.
AC   P78330;
DT   30-MAY-2000 (Rel. 39, Created)
DT   30-MAY-2000 (Rel. 39, Last sequence update)
DT   16-OCT-2001 (Rel. 40, Last annotation update)
DE   L-3-phosphoserine phosphatase (EC 3.1.3.3) (PSP) (O-phosphoserine
DE   phosphohydrolase) (PSPase).
GN   PSPH.
OS   Homo sapiens (Human).
OC   Eukaryota; Metazoa; Chordata; Craniata; Vertebrata; Euteleostomi;
OC   Mammalia; Eutheria; Primates; Catarrhini; Hominidae; Homo.
OX   NCBI_TaxID=9606;
RN   [1]
RP   SEQUENCE FROM N.A.
RX   MEDLINE=97332542; PubMed=9168776; [NCBI, ExPASy, EBI, Israel, Japan]
RA   Collet J.-F., Gerin I., Rider M.H., Veiga-Da-Cunha M.,
RA   Van Schaftingen E.;
RT   "Human L-3-phosphoserine phosphatase: sequence, expression and
RT   evidence for a phosphoenzyme intermediate.";
RL   FEBS Lett. 408:281-284(1997).
CC   -!- FUNCTION: CATALYZES THE LAST STEP IN THE BIOSYNTHESIS OF SERINE
CC       FROM CARBOHYDRATES. THE REACTION MECHANISM PROCEEDS VIA THE
CC       FORMATION OF A PHOSPHORYL-ENZYME INTERMEDIATES.
CC   -!- CATALYTIC ACTIVITY: Phosphoserine + H(2)O = serine + phosphate.
CC   -!- COFACTOR: MAGNESIUM.
CC   -!- SUBUNIT: HOMODIMER.
CC   -!- SIMILARITY: BELONGS TO THE SERB FAMILY.
CC   ----------------------------------------------------------------
CC   This SWISS-PROT entry is copyright. It is produced through a collaboration
CC   between the Swiss Institute of Bioinformatics and the EMBL outstation -
CC   the European Bioinformatics Institute. There are no restrictions on its
CC   use by non-profit institutions as long as its content is in no way
CC   modified and this statement is not removed. Usage by and for commercial
CC   entities requires a license agreement (See http://www.isb-sib.ch/announce/
CC   or send an email to license@isb-sib.ch).
CC   ----------------------------------------------------------------
DR   EMBL; Y10275; CAA71318.1; -. [EMBL / GenBank / DDBJ] [CodingSequence]
DR   MIM; 172480; -. [NCBI / EBI]
DR   GeneCards; PSPH.
DR   GeneLynx; PSPH.
DR   Ensembl; P78330.
DR   SOURCE; PSPH.
DR   InterPro; IPR001454; Hignase/hydrlase.
DR   InterPro; IPR004469; SerB.
DR   InterPro; Graphical view of domain structure.
DR   Pfam; PF00702; Hydrolase; 1.
DR   TIGRFAMs; TIGR00338; serB; 1.
DR   ProDom [Domain structure / List of seq. sharing at least 1 domain]
DR   BLOCKS; P78330.
DR   ProtoMap; P78330.
DR   PRESAGE; P78330.
```

Figure 33B

SWISS-PROT: P78330

```
OR   OIP; P78330.
OR   HodBase; P78330.
DR   SWISS-2DPAGE; GET REGION ON 2D PAGE.
KW   Hydrolase; Serine biosynthesis; Magnesium; Phosphorylation.
SQ   SEQUENCE   225 AA;   25022 MW;   ECE5C34255F5D115 CRC64;
     HISHSELRKL FYSADAVCFD VDSFVIREEG IDELAKICGV EOAVEEMTRR AMGGAVPFKA
     ALTERLALIQ PSREQVQRLI AEQPPHLTPG IRELVSRLQE RNVQVFLISG GFRSIVERVA
     SKLNIPATNV FANRLKFYFN GEYAGFDETQ PTAESGGKGK VIKLLKEKFH FKRIINIGOG
     ATOMEACPPR OAFIGFGGHV IROGVKDHAK WYITDFVELL GELEE
//
```

*P78330 in FASTA format*
*NiceProt - a user-friendly view of this SWISS-PROT entry*
*View entry in raw text format (no links)*
*Report form for errors/updates in this SWISS-PROT entry*

 Direct BLAST submission at EMBnet-CH/SIB (Switzerland)     Direct BLAST submission at NCBI (Bethesda, USA)

 ScanProsite, MotifScan     Sequence analysis tools: ProtParam, ProtScale, Compute pI/Mw, PeptideMass, PeptideCutter, Dotlet (Java)

 Feature table viewer (Java)     Search the SWISS-MODEL Repository

| ExPASy Home page | Site Map | Search ExPASy | Contact us | SWISS-PROT |
| Hosted by NCSC US | Mirror sites: | Australia | Canada | China | Korea | Switzerland | Taiwan |

Figure 34B

NCBI-UniGene

Rattus norvegicus

Xenopus laevis

UniGene Plants

Arabidopsis thaliana

Hordeum vulgare

Oryza sativa

Triticum aestivum

Zea mays

Related Resources

Human Genome Guide

LocusLink

HomoloGene dbEST-Database of Expressed Sequence Tags

Cancer Genome Anatomy Project

I.M.A.G.E. Quality Control cell carcinoma, undifferentiated;lung;lung focal fibrosis;lymph;lymphoma, cell line;melanotic melanoma;mucoepidermoid carcinoma;muscle (skeletal);nervous_tumor;neuroblastoma cells;osteosarcoma, cell line;placenta;pool;pooled colon, kidney, stomach;pooled lung and spleen;primitive neuroectoderm;retinoblastoma;stomach;thyroid;whole embryo;whole embryo, mainly head SAGE : Gene to Tag mapping mRNA SEQUENCES (2)

| | | | |
|---|---|---|---|
| NM_004577 | Homo sapiens phosphoserine phosphatase (PSPH), mRNA | | P A |
| Y10275 | H.sapiens mRNA for L-3-phosphoserine phosphatase | | P A |

EST SEQUENCES (10 of 101)[Show all ESTs]

| | | | |
|---|---|---|---|
| BF698598 cDNA clone IMAGE:4282223 | primitive neuroectoderm | 5' read | P M |
| BF699126 cDNA clone IMAGE:4283628 | primitive neuroectoderm | 5' read | P M |
| BF669381 cDNA clone IMAGE:4277859 | primitive neuroectoderm | 5' read | P M |
| BF700423 cDNA clone IMAGE:4287566 | primitive neuroectoderm | 5' read | P M |
| BF669233 cDNA clone IMAGE:4277012 | primitive neuroectoderm | 5' read | P M |
| BE543892 cDNA clone IMAGE:3457797 | cervical carcinoma cell line | 5' read | P M |
| BF699165 cDNA clone IMAGE:4283568 | primitive neuroectoderm | 5' read | P M |
| BE257645 cDNA clone IMAGE:3353678 | retinoblastoma | 5' read | P M |
| BI223114 cDNA clone IMAGE:5104424 | cervical carcinoma cell line | 5' read | P M |
| BE251421 cDNA clone IMAGE:3356814 | retinoblastoma | 5' read | P M |

Key to Symbols

P Has similarity to known Proteins (after translation)
A Contains a poly-Adenylation signal
M Clone is putatively CDS-complete by MGC criteria

DOWNLOAD SEQUENCES

There will be a pause of up to one minute before your computer receives any data. The default filename will be "download" if your operating system responds to filename suffixes, remember to choose a

Figure 34C

NCBI-UniGene suffix compatible with plain text or fasta formats.

Unix [ Download sequences ]

switch to text mode

NLM|NIH|UniGene   Privacy Statement   [Disclaimer]   NCBI Help

Figure 50B

| # | Process | % | p-Value |
|---|---|---|---|
| 1 | regulation of cell cycle | 21.62 | 2.243e-09 |
| 2 | organogenesis | 13.51 | 5.218e-06 |
| 3 | development | 17.57 | 7.860e-06 |
| 4 | inflammatory response | 13.51 | 8.117e-06 |
| 5 | proteolysis and peptidolysis | 13.51 | 1.446e-05 |
| 6 | induction of apoptosis | 9.46 | 1.981e-05 |
| 7 | DNA damage induced protein phosphorylation | 4.05 | 3.154e-05 |
| 8 | lymph gland development | 5.41 | 3.694e-05 |
| 9 | collagen catabolism | 5.41 | 6.118e-05 |
| 10 | myoblast differentiation | 4.05 | 9.123e-05 |

METHODS FOR IDENTIFICATION OF NOVEL PROTEIN DRUG TARGETS AND BIOMARKERS UTILIZING FUNCTIONAL NETWORKS

CROSS-REFERENCE TO RELATED APPLICATIONS

This application is a continuation-in-part of, and claims priority under 35 U.S.C. §120 to, U.S. application Ser. No. 10/518,103, entitled "Methods for Identifying Compounds for Treating Disease States," filed on Oct. 14, 2005; which claims priority under 35 U.S.C. §120 as a continuation-in-part to U.S. patent application Ser. No. 10/174,762 filed on Jun. 18, 2002, entitled "Competitive Analysis of EST Data and Functional Reconstruction Technology"; which claims priority under U.S.C. §119(e) to U.S. Provisional Patent Application No. 60/299,040 filed on Jun. 18, 2001, by Nikolskaya et al., entitled "Competitive Analysis of EST Data and Functional Reconstruction Technology." All of these applications are herein incorporated by reference in their entirety.

STATEMENT REGARDING FEDERALLY SPONSORED RESEARCH OR DEVELOPMENT

Not Applicable

INCORPORATION-BY-REFERENCE OF MATERIAL SUBMITTED ON A COMPACT DISC

Not Applicable

BACKGROUND OF THE INVENTION

1. Field of the Invention

The present invention relates to bioinformatics technologies. More specifically, the present invention relates to the technology of System Reconstruction. The present invention further relates to methods for elucidating metabolic pathways for the identification of novel therapeutic targets and biomarkers using network analysis. The initial seed networks are built from the lists of novel targets for diseases with the high-throughput experimental data being superimposed on the seed networks to identify specific targets.

2. Description of Related Art

The past few years have seen dramatic advances in genomics and other areas of high-throughput biology. The fruits of these accelerated technologies culminated in last-years publication of the human genome. The availability of the DNA sequence of the human genome promises to alleviate much of human suffering from life-threatening diseases. Knowledge of an entire genome may lead to the discovery of new drug targets. Access to the DNA sequence of an individual promises to reduce drug side effects and to allow tailoring medicine to the individual's genetic makeup. Both government agencies and drug companies have invested heavily in these technologies. In return, they expected to vastly reduce the cost and time of drug development, a process costing on average over $500 million in the 1990s and usually spanning over a decade from the initial discovery of drug targets and leads, through validation, optimization, and finally clinical trials.

Currently, these expectations are far from reality because human biology is complex, and there has been no systematic approach to capture this biological complexity. A new field of computational biology has been forged to make sense out of the inordinate amount of genomics data including DNA sequence data, gene expression data, proteomics, metabolomics, and cellomic data. It is believed by many in the industry that the integration of these data alone would quickly lead to the correlation of phenotype (clinical manifestations) with genotype (variations in gene sequence). That goal is still far off, however, as the majority of these data are examined out of context. The basis of a disease cannot be understood without understanding, for example, the alternative splicing forms of the related genes, the proteins for which they code, the complex networks of protein interactions involved, the multiple levels of gene regulation and expression, the correlations between healthy and diseased tissue, the significance of clinical data, and the like. The complexity of human biology requires a systemic understanding of genomic data rather than a shotgun understanding. As a result, the field of systems biology arose and is rapidly becoming a leading approach to understanding human biology.

Recent progress in sequencing technology has generated a vast amount of genomic data. According to the GOLD database, there are more than 300 genomic projects currently completed or under development (wit.integratedgenomics.com/GOLD/). Seventy-nine complete or partially complete genomes are available through the public ERGO system (igweb.integratedgenomics.com/IGwit/). In order to handle this wealth of information, several powerful bioinformatics systems have been developed. The WIT Project was instituted to develop a framework for the comparative analysis of genomic sequence data, focusing largely on the development of metabolic models for sequenced organisms. The analysis of the genomes involves several distinct, but complementary efforts. The first is a determination of open reading frames (ORFs). The second, often called annotation, is the assignment of functions to genes. The third is the creation of functional models for metabolic and regulatory networks of the sequenced genomes, referred to as reconstruction.

Metabolic reconstruction for bacterial and archaeobacterial genomes has been carried out. In contrast, metabolic reconstruction for eukaryotic organisms remains a much more complicated problem. Despite significant progress in genome sequencing, the annotation of eukaryotic genomes remains a complicated problem. Even finding the ORFs, a key component of gene identification, is still a very difficult task. A comprehensive understanding of the complicated structure of eukaryotic genomes will require the integration of sequencing information with genetic, biochemical, structural, and evolutionary data. It will require developing new bioinformatics tools and discovering new algorithms, and, most likely, it will take years of research in both dry and wet labs.

Traditionally, it has not been considered feasible to study metabolism based on expressed sequence tag (EST) data. Such an approach, however, would be very useful for comparative analyses of complex eukaryotic genomes. First, generation of a complete set of ESTs is at least an order of magnitude less expensive than whole genome sequencing. Second, there is a great deal of processed EST data freely available to the scientific community. Currently, there are only a few complete eukaryotic genomes available to the public, but there are sufficient EST data for several dozens of species. Third, and most important, ESTs represent genes that are expressed at specific times in specific tissues. In the present invention, expressed sequence tag data, rather than genomic sequences, were used to reconstruct various aspects of human metabolism.

Several databases exist for collecting EST sequence and expression patterns for eukaryotic genes (for example Unigene EST, dbEST, STACK, SAGE, DOTS, trEST, XREFdb, in addition to a number of tissue-specific databases, such as PEDB). A significant amount of human EST data has already been carefully analyzed, classified, annotated, and mapped to chromosomes. Currently, there are over 1,000,000 human ESTs available in public databases representing 50-90% of all human genes. It is generally believed, however, that EST sequences are inferior to genomic DNA sequences in terms of their quality and degree of representativeness.

Additionally, numerous public and commercial efforts that have focused on characterizing various aspects of general biochemistry and metabolism. Some of these databases include KEGG, BRENDA, SWISS-PROT, EcoCyc, and EMP/MPW. None of these databases, however, focus specifically on humans, or on a single species.

The technology known as Metabolic Reconstruction was developed by Dr. Evgeni Selkov and co-workers at the Argonne National laboratory. Metabolic Reconstruction was developed to study an organism's metabolism by using its genome sequence. A reconstruction of the metabolism of *Methanococcus jannaschii* from sequence data can be found in *Gene,* 197, GC11-26.

Cellular life can be represented and studied as the interactome the dynamic network of biochemical reactions and signaling interactions between active proteins. Systemic networks analysis is optimal for integration and functional interpretation of high-throughput experimental data which are abundant in drug discovery yet poorly understood. Composition and topology of complex networks are closely associated with vital cellular functions, which have important implications for life science research. Network theory advances has, in recent years, quickly advanced; and reliable databases of protein interactions for human and model organisms and comprehensive analytical tools have become available. In this application, we present a specific application of networks analysis: identification of novel drug targets by reverse engineering the networks which connect the existing targets for specific disease, followed by superposition of experimental molecular data such as microarray gene expression, proteomics and metabolomics.

Over the last several years known as the post-genomics era, we have seen a paradigm shift in life science research due to the unprecedented scale-up of several laboratory techniques such as automated DNA sequencing, global gene expression measurements, and proteomics and metabolomics techniques. The high throughput (HT) data collectively referred to as OMICs are ubiquitous throughout the drug discovery pipeline from target identification and validation to the development and testing of drug candidates to clinical trials. However, OMICs data is poorly utilized due to the lack of the adequate methods for interpretation in the context of disease and biological function. Although bioinformatics has developed robust statistical solutions for evaluation of the significance and clustering the data points, statistics alone do not explain the underlying biology.

The complexity of human biology requires a system-wide approach to data analysis, which can be defined as the integration of OMICs data using computational methods. The field states that the identification of the parts list of all the genes and proteins is insufficient to understand the whole. Rather, it is the assembly of these parts (the general schema, the modules and elements) and the dynamics of changes in response to stimuli that is truly the key to understanding life, form and function. The assembly of cellular machinery is to be most properly presented as the interactome, the network of interconnected signaling, regulatory and biochemical networks with proteins as the nodes and physical protein-protein interactions as edges. Across many fields of science, technology and social life, the topology and dynamics of complex networks are studied by graph theory. The information about protein interactions has being collected from the vast published experimental data, which is annotated and assembled in the interactions databases. The network data analysis that are now commercially available are robust enough for simultaneous processing of dozens of multi-thousand featured strong data files such as whole-genome expression microarrays. Just recently, researchers in systems biology announced the interpretation of experimental OMICs datasets in the context of accumulated knowledge on human functional networks as the first step in studying complex systems. With this development, the building of the basic framework of databases and logistics can be considered completed. Networks-centered data analysis is now well underway at the major pharmaceutical companies.

BRIEF SUMMARY OF THE INVENTION

The process of the present invention, referred to as System Reconstruction, integrates data on organism- and tissue-specific biochemical pathways, genome sequences, conditional gene expression, and genetic polymorphisms with clinical manifestations of diseases and other clinical traits. As a result, a network of interconnected functional pathways (a Functional or System Model) is constructed in which elements are linked to appropriate molecular data (ORFs, ESTs, SNPs, etc.) and annotated with relevant clinical information.

Generally, the first step in creating a System Reconstruction model is the determination of a network of relevant biochemical pathways, specific for certain human tissues at certain developmental stages (Metabolic Reconstruction). Next, the collection of pathways is extended by computational reconstruction of relevant metabolic networks. Third, the expression data is integrated into the resulting metabolic map to generate a snapshot for any specific cell, organ, or tissue. Comparison of such snapshots constructed for the same tissue in normal and disease states (or in different developmental stages), provides valuable information about regulatory mechanisms of the disease or of development. Finally, the System Reconstruction model is completed by integrating the developmental pathways and mapping them onto the metabolic network. This step verifies the regulatory pathways and completes the functional overview of the network.

In one aspect, the present invention ascertains necessary functions involved in a particular metabolic pathway.

In another aspect, the present invention provides a visual overview of I expressed genes associated with a particular pathway specific for normal and abnormal human tissues.

In another aspect, the present invention provides a method for I determining and identifying the ORFs involved in those pathways.

In another aspect, the present invention provides a method for comparing System Reconstructions made for normal and diseased organs or tissues, thus providing important information about possible regulatory mechanisms and potential drug targets. In another aspect, the present invention provides a method for comparing the reconstructions made for the same tissue at different developmental stages, thus providing information about the developmental timing of gene expression and revealing possible targets for gene therapy.

In another aspect, the present invention provides a method for I mapping single nucleotide polymorphism (SNP) sites to corresponding metabolic genes and/or predicted ORFs, thus providing physiological insights into associations of SNPs with unknown phenotypes.

The present invention relates to a method for determining necessary functions involved in a particular metabolic pathway. In one aspect, the present invention provides a visual overview of expressed genes associated with a particular pathway specific for normal and abnormal human tissues. The present invention can also provide a method for determining and identifying the ORFs involved in those pathways. The present invention further provides a method for comparing System Reconstructions made for normal and diseased organs or tissues, thus providing important information about possible regulatory mechanisms and potential drug targets.

In another aspect, the present invention provides a method for comparing the reconstructions made for the same tissues at different developmental stages, thus providing information about the developmental timing of gene expression and revealing possible targets for gene therapy.

In another aspect, the present invention provides a method for mapping single nucleotide polymorphism (SNP) sites to corresponding metabolic genes and/or predicted ORFs, thus providing physiological insights into associations of SNPs with unknown phenotypes.

The present invention also relates to the determination of complicated cellular networks using abundant gene expression data (such as EST and micro-array data) as well as genomic sequence data; the identification of relationships between different human genes, pathways and parts of metabolism the identification and grouping according to function of over- and under-expressed genes specific for given tissue or condition; the generation of interactive, integrated functional outlines for all parts of human metabolism.

Identification of novel therapeutic targets using network analysis. The initial seed networks are built from the lists of novel targets for diseases. The high-throughput experimental data is superimposed on the seed networks to identify specific targets.

BRIEF DESCRIPTION OF THE SEVERAL VIEWS OF THE DRAWINGS

The accompanying drawings are not intended to be drawn to scale. For purposes of clarity, not every component may be labeled in every drawing. In the drawings.

FIG. 12A is an example of an enzyme page for methionine adenosyltransferase.

FIG. 12B is an example of an enzyme page for methionine adenosyltransferase (continued from FIG. 12A).

FIG. 13 is an example of a reaction page.

FIG. 14 is an example of a gene page.

FIG. 15 is an example of a compound page.

FIG. 17 is an example of a disease page for atherosclerosis.

FIG. 20 shows a Parkinson disease page.

FIG. 25A shows notes associated with the serine biosynthesis scheme (3-phospho-D-glycerate/L-glutamate//2-oxoglutarate/L-serine/cyt).

FIG. 25B shows notes associated with the serine biosynthesis scheme (3-phospho-D-glycerate/L-glutamate//2-oxoglutarate/L-serine/cyt) continued from FIG. 25A.

FIG. 26 illustrates reaction 1 from the serine biosynthesis scheme [(Cytosol) 3-phospho-D-glycerate+NAD+=3-phosphohydroxypyruvate+NADH].

FIG. 27A is an enzyme page for EC 1.1.1.95, phosphoglycerate dehydrogenase.

FIG. 27B is an enzyme page for EC 1.1.1.95, phosphoglycerate dehydrogenase continued from FIG. 27A.

FIG. 28 illustrates reaction 2 from the serine biosynthesis scheme [(Cytosol) 3-phosphohydroxypyruvate+L-glutamate='O'-phospho-L-serine+2-oxoglutarate].

FIG. 29 is an enzyme page for EC 2.6.1.52, phosphoserine transaminase.

FIG. 30 illustrates reaction 3 from the serine biosynthesis scheme [(Cytosol) 'O'-phospho-L-serine+H2O=L-serine+phosphate].

FIG. 31 is an enzyme page for EC 3.1.3.3, phosphoserine phosphatase.

FIG. 32 is the Gene PSPH page for EC 3.1.3.3, phosphoserine phosphatase.

FIG. 33A is the SWISS-PROT: P78330 page for EC 3.1.3.3, phosphoserine phosphatase.

FIG. 33B is the SWISS-PROT: P78330 page for EC 3.1.3.3, phosphoserine phosphatase continued from FIG. 33A.

FIG. 34B is the UniGene Cluster Hs.56407 page for EC 3.1.3.3, phosphoserine phosphatase continued from FIG. 34A.

FIG. 34C is the UniGene Cluster Hs.56407 page for EC 3.1.3.3, phosphoserine phosphatase continued from FIGS. 34A and 34B.

FIG. 50B is a representation showing cellular processes as defined by Gene Ontology (GO) affected in the final network.

DETAILED DESCRIPTION OF THE INVENTION

A bioinformatics approach called System Reconstruction is used to integrate clinical information with high-throughput molecular data. In the core of this approach, a collection of human tissue-specific and condition-specific biochemical pathways are linked by common intermediates into maps or models. These models serve as a framework to integrate complementary types of high-throughput data and to establish mechanisms underlying clinical manifestations of diseases.

Figure 1:
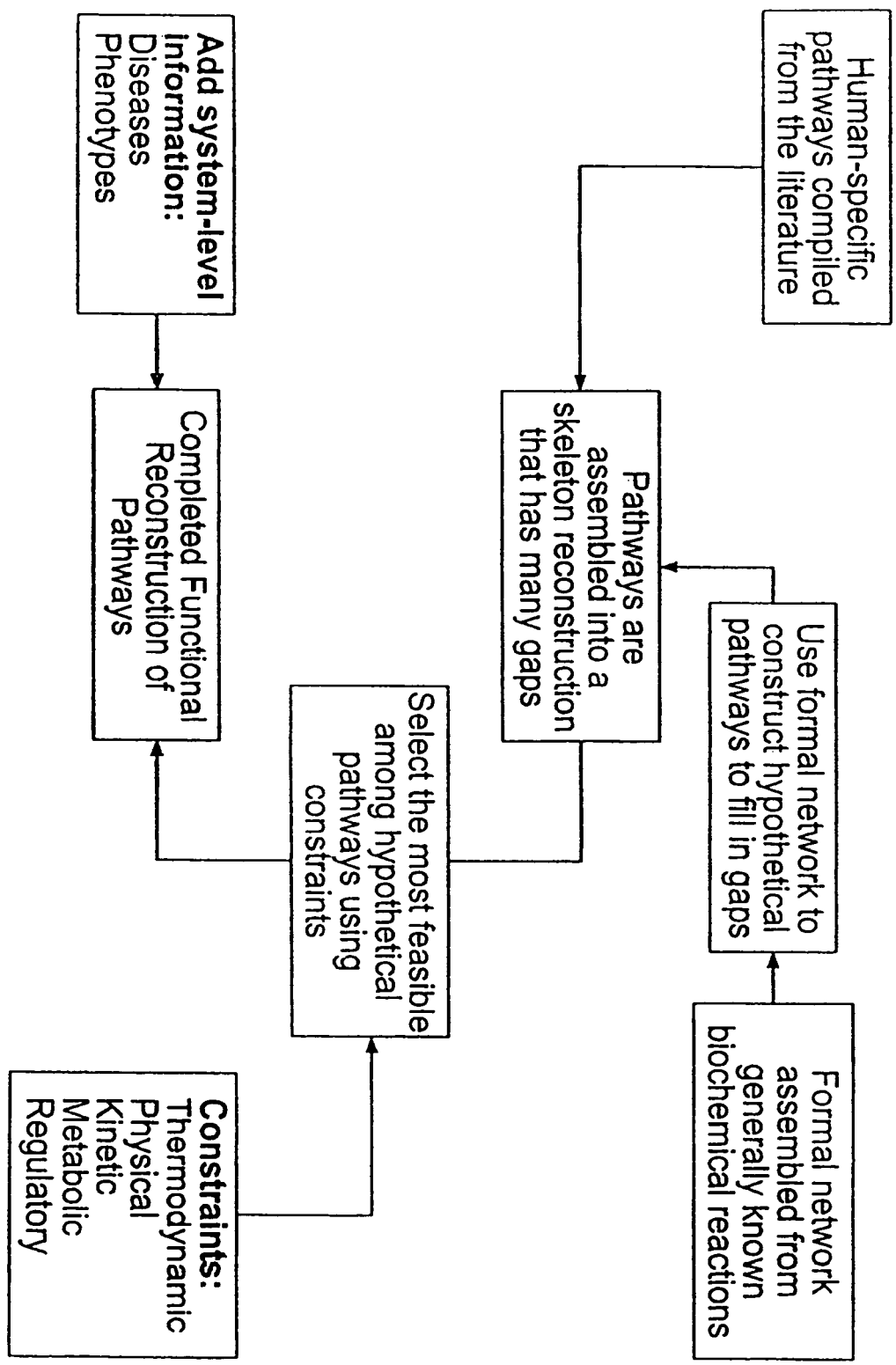
FIG. 1 is a schematic overview of the process of System Reconstruction.

The present invention creates a system that allows building human-specific system-level models of biochemistry. In summary, information regarding human-specific pathways is collected. The pathways are linked to functional information, disease manifestations, and high-throughput data. Finally, pathways are connected to each other and linked to relevant; information to form a functional model. These models can be used, for example, as skeletons for further integration of high-throughput data, for deciphering mechanisms of diseases, for predicting drug metabolism and toxicity, and the like. System Reconstruction is a complex multi-step process that involves assembling a collection of human-specific pathways and results in fully annotated interactive maps of specific metabolic systems (see FIG. 1).

The process of System Reconstruction generally starts with the creation of a collection of metabolic pathways. Pathways that are human specific and in the form in which they occur in humans are included. Building such a collection is achieved through a multi-level annotation process. Starting with a collection of identified metabolic pathways from mammals and non-mammals, the pathways are divided into categories based on relevance. For example, pathways are ranked according to the probability of their relevance in human metabolism. The most relevant pathways include multi-step mammalian pathways in which all of the reactions are catalyzed by identified human enzymes or at least enzymes that have ORE candidates in the human genome. Less relevant pathways include, for example pathways in which the necessary enzymes have not been identified in humans, and single step pathways. Information such as clinical data and scientific literature is reviewed to confirm which pathways are, in fact, present in humans.

In order to organize the information collected in the process of reconstruction, a relational database has been developed using Oracle RDBMS. Unlike many biomedical databases which are centered around a certain theme (e.g. sequences, proteins, biochemical reactions, etc.), the database developed in the present invention is a polythematic database that is built around several central data entities and relations among them. These entities are enzymes; compounds; reactions; pathways; genes; and diseases. This core architecture provides multiple linking portals for including other often heterogeneous data such as gene expression, protein interactions, metabolite profiles, etc. Once linked, these data become a part of a large system-level picture.

Currently, the database contains about 3300 pathways described in various species of mammals and about 2060 non-mammalian pathways. Of the mammalian pathways about 920 are multi-step pathways and the rest are single-step pathways. The pathways are divided into several categories according to the probability of their relevance to human metabolism. The most relevant category includes multi-step mammalian pathways for which all reactions are catalyzed by either identified human enzymes or enzymes that have ORF candidates in the human genome (about 710 pathways). The next category includes multi-step mammalian pathways that have human enzymes at the beginning and at the end of the pathway (about 40 pathways). In the next category, there are mammalian and non-mammalian multi-step pathways that contain human enzymes in the middle of the pathway (about 800 pathways). Finally, there are pathways with no identified human enzymes (about 1500 pathways).

In addition to these categories, there is a collection of single step reactions that can be catalyzed by human enzymes (about 2300 pathways) or by mammalian enzymes (over 5000 pathways). It should be noted, however, that not every such reaction, which can be catalyzed by a human enzyme, is in fact a functional human pathway. Many enzymes possess a broad spectrum of specificity in vitro, while in vivo there are many additional constraints that limit their functionality such as, e.g., compartmentalization, absence of precursors, and kinetic competition.

The process of ranking, as described above, creates a working collection of pathways that are then annotated. The initial collection of pathways may contain many pathways that are similar to human pathways but still have essential differences. Some of the differences may be in cofactors or sub-cellular localization of enzymes and metabolites. Also, human versions of pathways may be truncated or contain additional steps when compared to pathways from other species. Since many enzymes show a range of specificity, they may substitute for each other in similar pathways from different species. Therefore, during the annotation process, the available literature for every pathway is reviewed to determine the human specific form of the pathway. Pathways from the two most relevant categories are usually easy to verify through biomedical literature and generally require few, if any, modifications. The third category of pathways, as well as single step reactions with human enzymes, generally require a thorough literature search to be confirmed or rejected as human-specific pathways and usually undergo substantial changes. Finally, pathways with no human enzymes are left until the later stages when metabolic maps are built. At that point, some of those pathways are selected as candidate human pathways if they fit well into gaps in the map that cannot be easily filled by pathways from higher-ranking categories.

In addition to creating a collection of human specific pathways, the process of annotation yields important functional data about each pathway and its elements. In order to structure this information, a pathway is described as a hierarchy of biochemical units. These units comprise the pathway itself, individual steps that make up the pathway, chemical compounds, reactions, and enzymatic functions that are involved in each step. Enzymatic functions are related, in turn, to molecular species-specific proteins and genes.

In a process called structured annotation, explicit and implicit links are established between particular biochemical units and specific categories and instances in other data fields, discussed in greater detail below. Practically, this is achieved by filling in annotation tables associated with each biochemical unit. Examples of fields in these tables include: organ and tissue localization of the unit; intracellular localization and/or compartmentalization; existence and sub-cellular localization of the unit in other organisms; connection of the unit with inherited and common diseases and other functional disorders; type of relationship between the unit and a disease (e.g., cause, manifestation, etc.); references on the information source; and the like. The individual data fields can be linked in numerous ways including finding compounds, enzymes, reactions, and pathways that are directly linked in a particular unit; automatically interconnecting pathways and reactions into networks based on shared intermediates or other links; establishing constraints on pathway interactions based on sub-cellular localization of their components; finding pathways, reactions compounds, and enzymes related to a disease, its causes or manifestations, and interconnecting such elements into a disease network; finding diseases related by common pathways, reactions, or compounds; and finding alternative pathways for degradation or biosynthesis of specific compounds, to circumvent certain enzymes.

Thus, in the architecture of the database, functions can have a role as space-holders (FIG. 7) to which additional molecular data are linked as they are discovered. Functions therefore are linking portals for heterogeneous data, such as gene expression, protein interactions, metabolite profiles, and the like. Once linked, these data become a part of a large system-level picture in which functional relations among the data can be elucidated.

Figure 7:
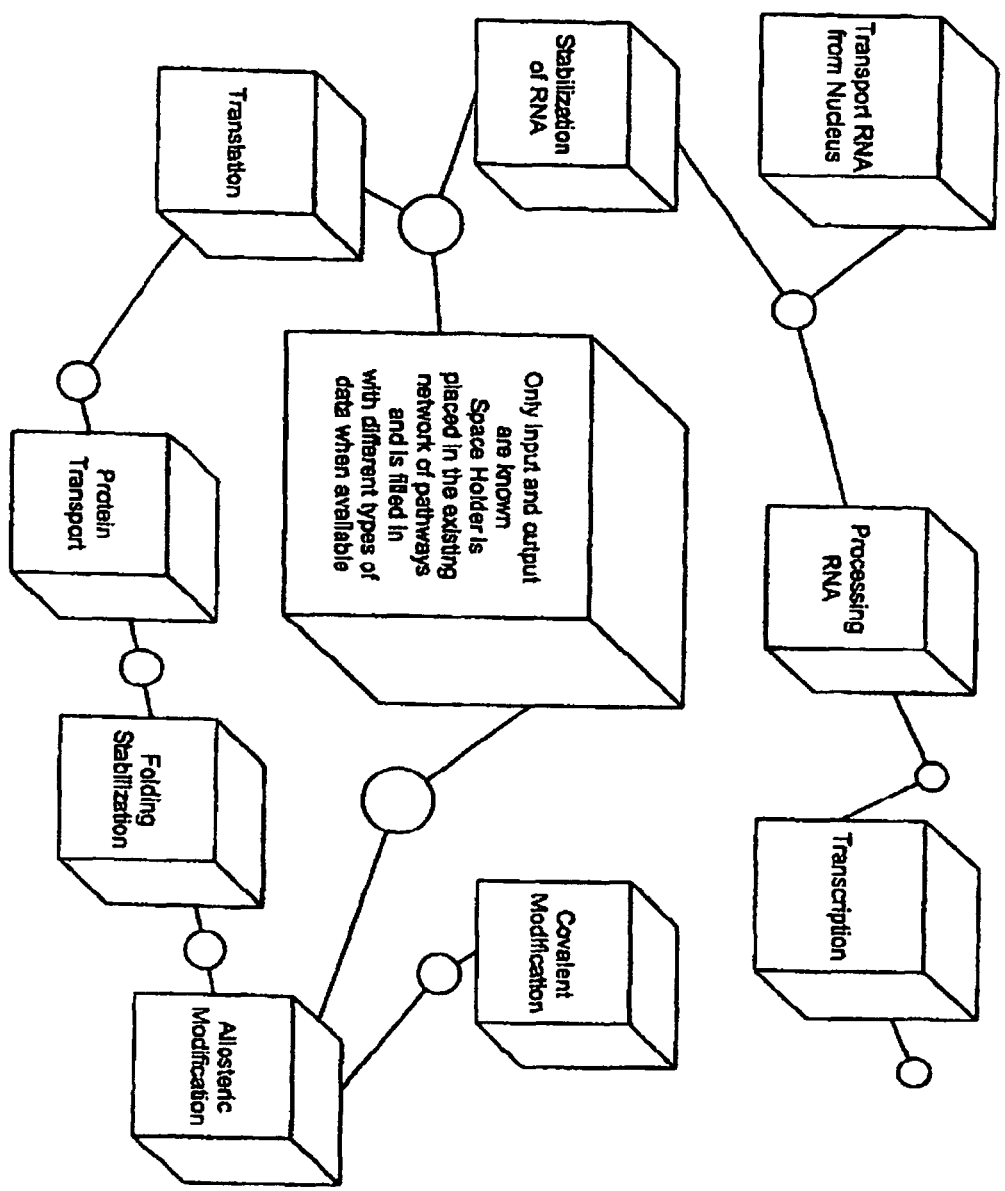
FIG. 7 is a chart illustrating the function of space holders in a System Reconstruction database.

As illustrated in FIG. 7, processes or functions act as space-holders for any molecular, mechanistic, dynamic, or other type of data that may be discovered later. Often, biological phenomena are initially described as set of inputs and outputs, or actions and responses, with little or no knowledge of the underlying mechanism or the molecular entities involved. In a database according to the present invention, it is possible to place such phenomena into the context of other processes by matching inputs and outputs. The resulting network links processes together based on these inputs and outputs, even when little detailed knowledge is available. As additional data become available, they are linked to the corresponding processes. Thus, the use of such space-holders allows heterogeneous data that have little overlap to be integrated into the self-consistent system-level picture.

Preferably, the database architecture accounts for various complexities of metabolism. For example, most enzymes can catalyze a range of reactions, and many reactions can be catalyzed by more than one enzyme. This multiplicity is preferably represented in a System Reconstruction database. As another example, there is usually more than one gene that corresponds to an enzyme or enzymatic function. There are currently about 2000 human genes assigned to enzymes corresponding to about 800 EC numbers. This type of multiplicity can also be represented in a database according to the present invention.

The next step is the building of functional models of specific categories of human metabolism, diseases, and other system-level reconstructions. Two important steps are (1) selecting a subset of the relevant pathways, and (2) linking them into metabolic networks. The selection of pathways is done by a set of "SELECT . . . FROM . . . WHERE . . . " type queries, relying on the information collected in the structured annotation tables discussed above. The information on links among pathways is implicitly contained in the database. For example, whenever two pathway records share a common intermediate, or when an intermediate in one pathway occurs as a regulatory factor in a record for an enzyme from another pathway, a link is generated between the two pathways. Further computations are facilitated when such links are translated into explicit relations among pathways. To this end, stoichiometric matrices that represent the participation of compounds in the reactions are assembled. Using these matrices, it is possible to find links among reactions and, since reactions are already related to pathways in the database, a network of interconnected pathways can be generated.

At this stage, such networks are considered crude skeletons and are likely to contain substantial gaps as well as many nonfunctional links among pathways. A careful review and modification is undertaken to develop approved functional models. To fill in gaps, a set of candidate pathways is chosen from pathways of closely related organisms as well as from hypothetical pathways, and constructed by formally linking reactions. Then genomic DNA and ESTs are used as additional evidence to validate the proposed pathways.

It should be noted that the quality of stand-alone eukaryotic ESTs is often not sufficient for unambiguous functional assignments. However, if functional assignments are done with additional constraints imposed by a skeletal functional model, the ambiguity generally can be eliminated. In other words, an initial functional model provides insight into the work plan of a specific biochemical system, thereby allowing other data to be analyzed within the context of this work plan.

At this stage, sets of enzymatic functions that participate in the hypothesized pathways are identified and a determination is made as to which ones can be verified by sequence and expression data. Those that are supported by this evidence are added to the model as proposed pathways. It is also possible to consider other types of high-throughput data including metabolic profiles, two-hybrid assays, and other types of data to further validate these pathways. The proposed pathways can become primary targets for further experimental research. For the resulting network, the information on diseases associated with pathways, enzymes, and compounds is extracted from structured annotations and explicitly related to corresponding elements. The reconstruction is represented as an interactive map from which other information can be accessed, as described below.

The database developed according to the present invention can address various problems that often result from the traditional view of metabolism. The database can provide a representation of a wide spectrum of enzyme activity. Current enzyme nomenclature is built on the assumption that there is a single enzyme for each enzymatic reaction. This assumption is not always true in practice. Many enzymes can catalyze a range of reactions, and many reactions can be catalyzed by more than one enzyme. The database developed according to the present invention can represent this multiplicity by introducing many-to-many relations between enzymes and reactions.

The database can reflect the relationships between enzymatic function and molecular species. The term "enzyme" is somewhat ambiguous. While some biologists apply it to a particular protein—a molecule of certain chemical composition (or a complex of a few proteins)—, others refer to the function itself—an ability to catalyze a certain type of reaction. In the data model according to the present invention, this ambiguity is avoided by establishing several entities that are related to the term "enzyme". One such entity is enzymatic function which is an ability to catalyze a certain reaction or class of reactions. Enzyme nomenclature and EC numbers are used to classify functions. Relating to any given function, there are specific molecular entries, such as proteins and genes. This system avoids the ambiguity that can occur when a single protein may possess a spectrum of catalytic activities, or when there may be more than one protein capable of catalyzing a certain reaction. In addition to avoiding ambiguity, such a data model is extremely useful in the process of functional annotation. For example, a disease that is linked to an enzymatic deficiency could have many potential causes, such as a mutation in the gene coding for the enzyme, problems at the gene expression level, or protein mis-folding, to name a few. This expanded data model allows the association of a clinical trait with the appropriate specific data entity.

The database also addresses the compartmentalization and localization of enzymes and metabolites. In living cells, reactions take place in certain compartments and intracellular localizations. This is one of the major mechanisms that cells use to regulate intracellular processes. Many enzymes have a fairly broad spectrum of substrates. Specificity is often determined by co-localization of an enzyme and one of its substrates. In some cases, incorrect protein localization is implicated in a disease. This type of information is included in the database by developing a representation of cellular anatomy. Preferably, compartments and organelles found in different cell types and their mutual arrangement are reflected in the database. Spatial organization of metabolic processes is represented by establishing relationships between anatomical data and data on pathways, reactions, enzymes, and compounds.

Figure 2:
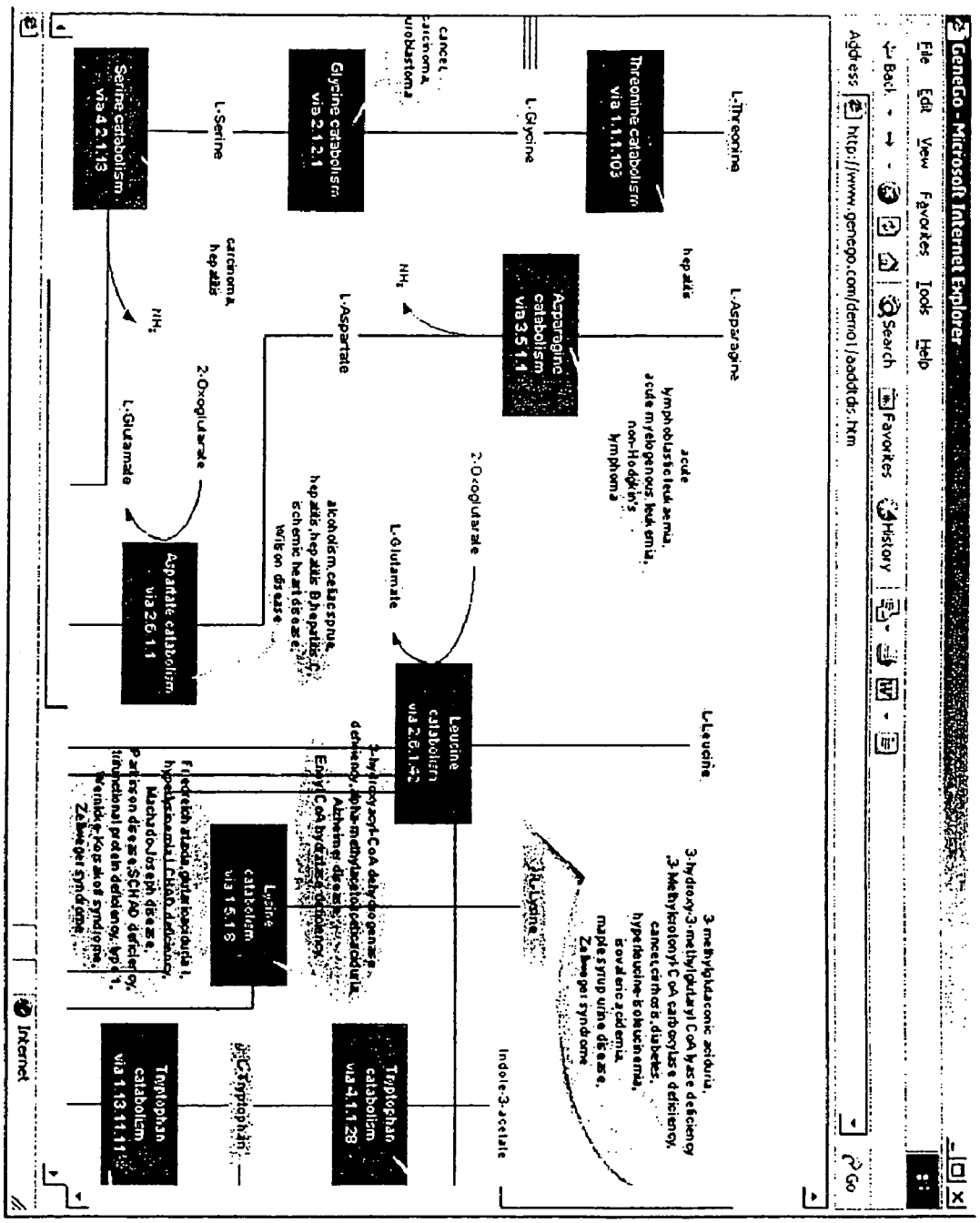
FIG. 2 illustrates a portion the reconstruction of human amino acid metabolism.
Figure 8:
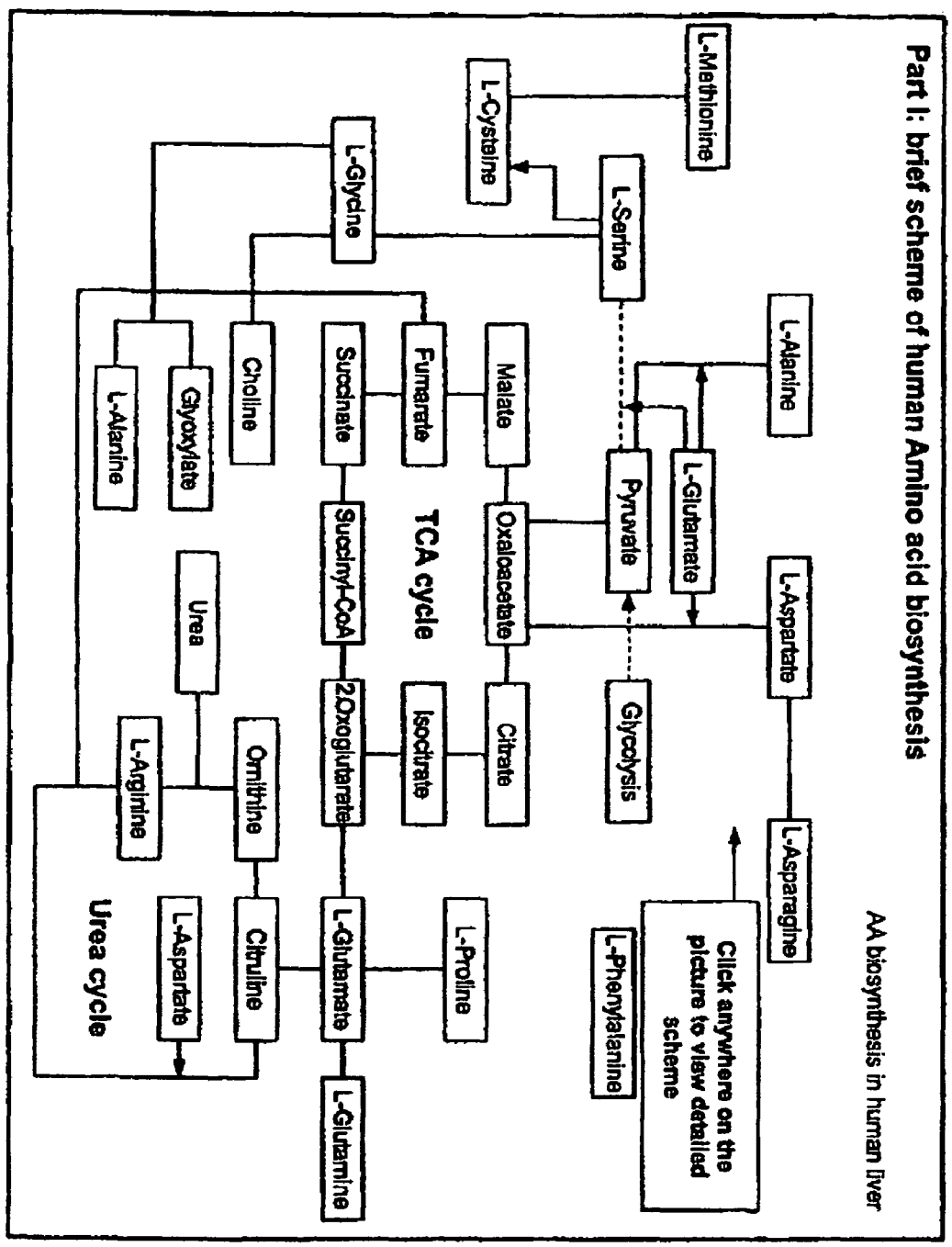
FIG. 8 illustrates a brief scheme of human amino acid biosynthesis.
Figure 9:
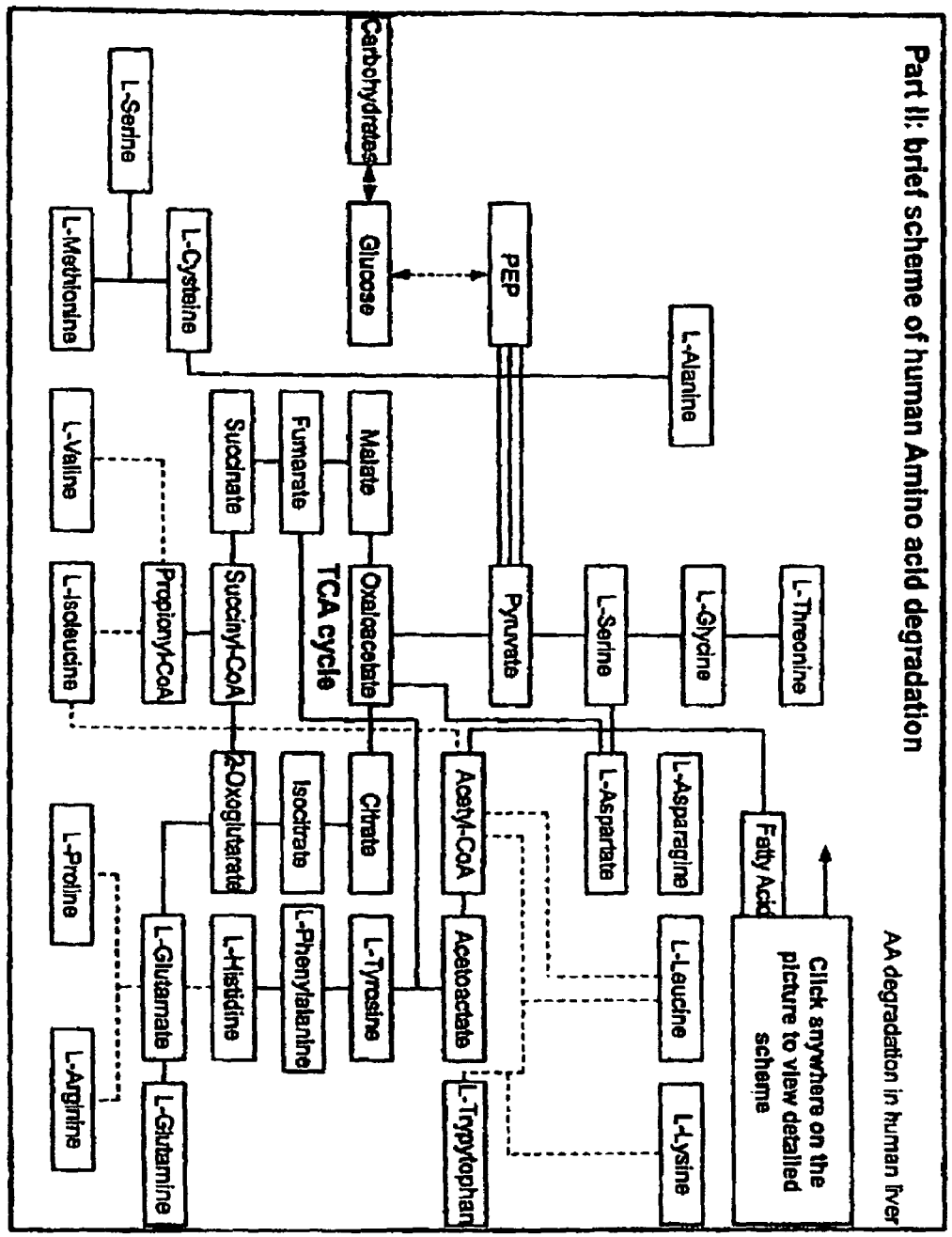
FIG. 9 illustrates a brief scheme of human amino acid degradation.

The technology of the present invention was used to build the System Reconstruction of amino acid metabolism in human, a portion of which is illustrated in FIGS. 2, 8 and 9 (and discussed in greater detail in Example 2). The reconstruction consists of two major parts: amino acid biodegradation (FIG. 9) and amino acid biosynthesis (FIG. 8). The user interface of the reconstruction is an interactive map showing pathways involved in amino acid metabolism. This annotated map of interconnected pathways is a front end to the underlying database containing entries into pathways, enzymes, metabolites, genes, and information about human diseases. The entities in the database are preferably linked through the core functional network, enabling a user to identify data linked by functional relationships.

A user can also retrieve information about the involvement of a particular pathway, reaction, or enzyme for a specific disease. Preferably, structured annotations are accessible for the elements of the network (e.g., for pathways, reactions, enzymes, and the like) that specify whether the element is the cause of the disease or a manifestation of the disease (part of the disease fingerprint). In addition, a user is able to cross-link among the biochemical fingerprints of different diseases. The information is accessible by clicking on from the corresponding objects on the graphical map.

Figure 10:
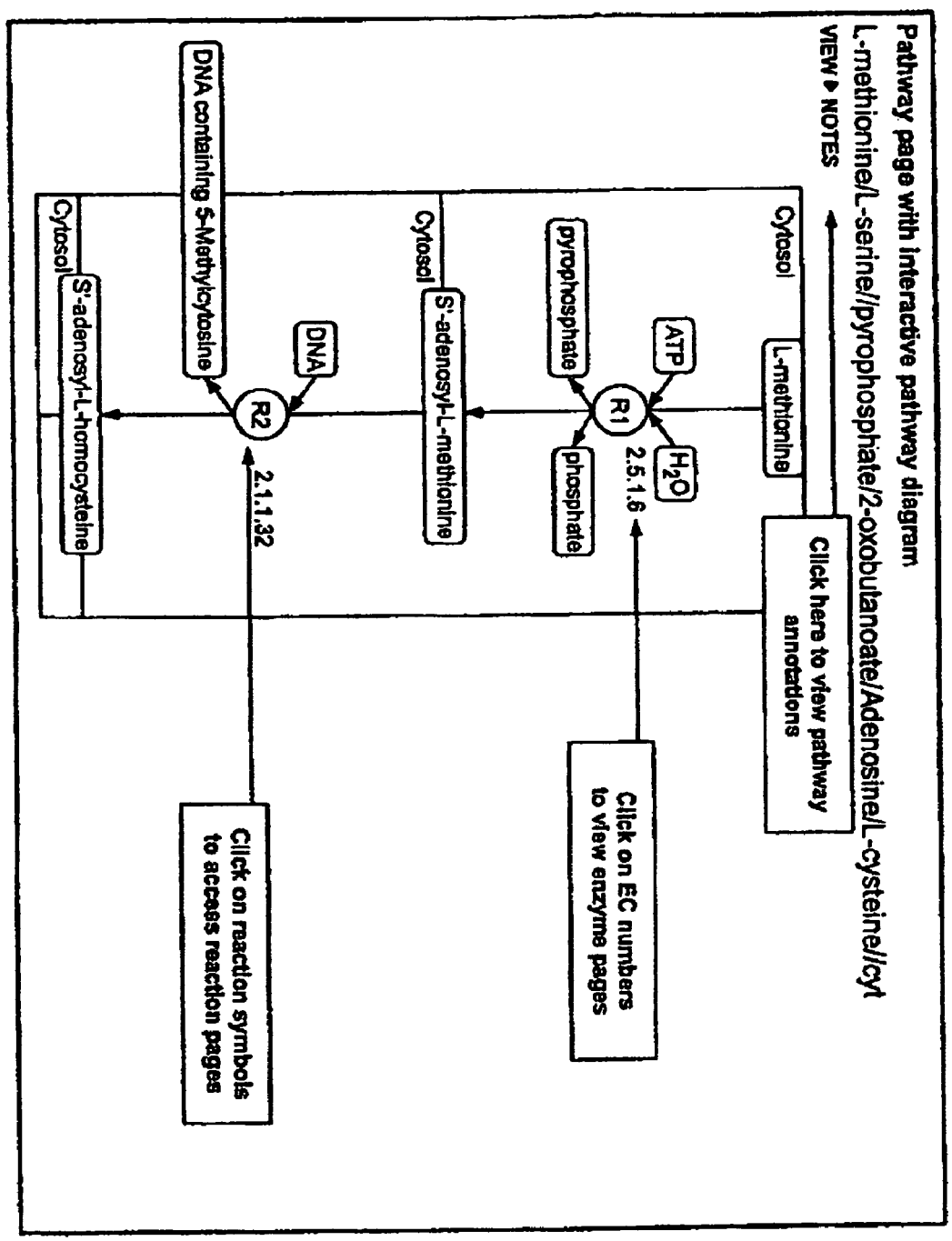
FIG. 10 is an example of a pathway page with an interactive pathway diagram.
Figure 11:
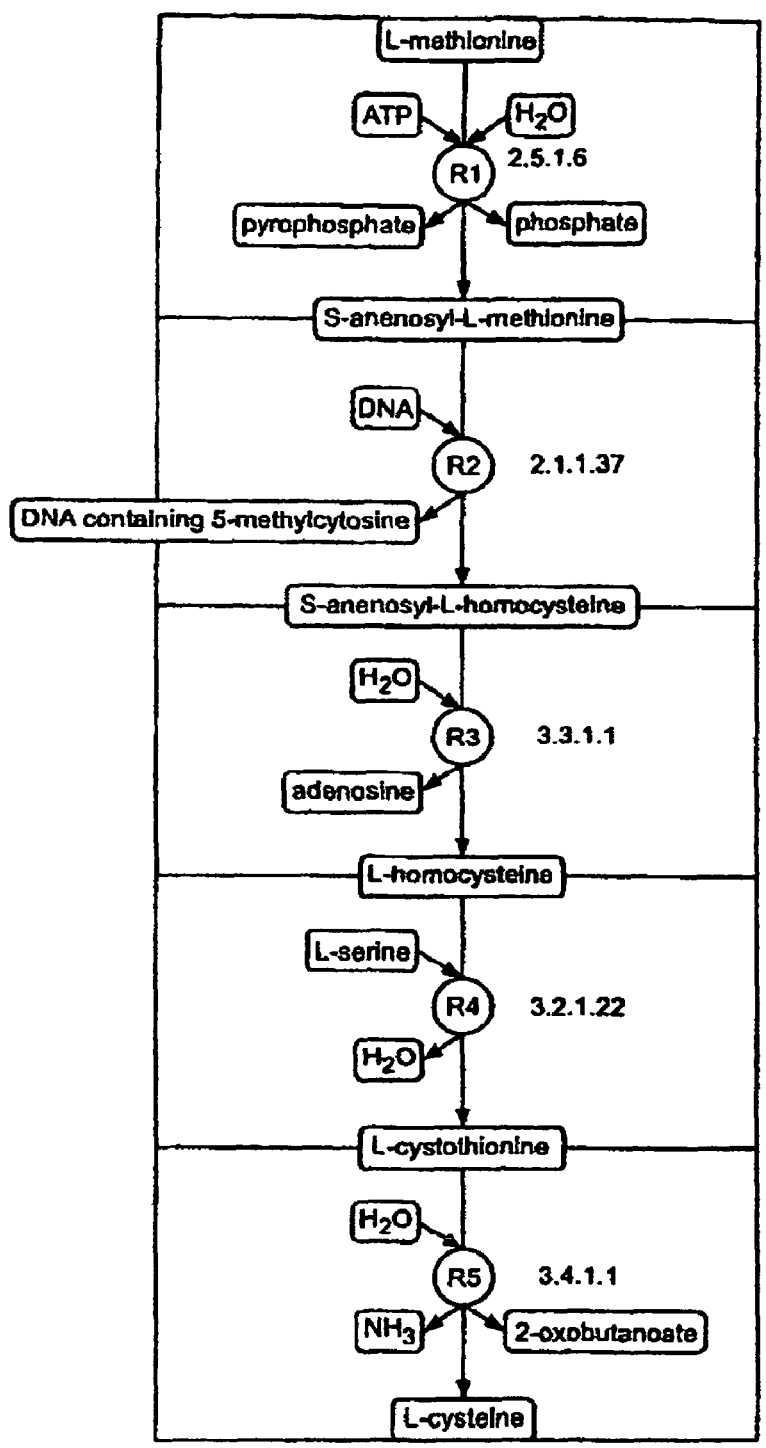
FIG. 11 is an example of a full view of a pathway diagram.

Pathways are interconnected into a network by shared metabolites. By clicking the mouse on a pathway or a component of a pathway, a user can access the pathway page (FIGS. 10 and 11) showing detailed diagrams with all reactions and enzymes. From this page, related pages for enzymes (FIGS. 12A and 12B), reactions (FIG. 13), and genes (FIG. 14) can also be accessed. In addition, pathway notes that describe diseases (FIG. 16) linked to the pathway are accessible from this page. An enzyme page (FIGS. 12A and 12B) contains the enzyme name and its synonyms, links to gene pages for genes related to the enzyme, a list of reactions and pathways in which the enzyme is involved, and notes on the involvement of the enzyme in human diseases.

Figure 16:
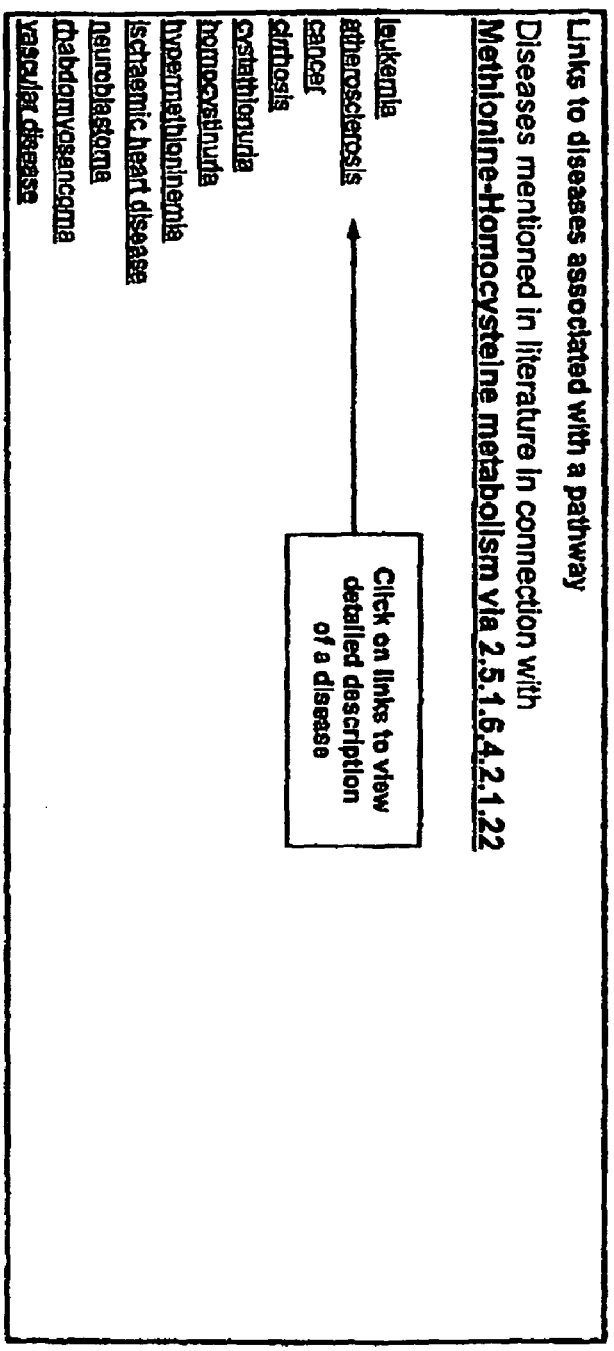
FIG. 16 is an example of a diagram showing links to diseases associated with a pathway.

One feature of the reconstruction is the incorporation of human diseases. By activating a link to diseases, a user can see lists of diseases associated with the pathway (FIG. 16). From these lists, pages for individual diseases (FIG. 17) can also be accessed. These pages contain lists of enzymes, reactions, and pathways that have been linked to a disease. In addition, one can view notes describing various aspects of a disease mechanism, its metabolic causes, and/or its manifestations (FIGS. 18-22).

One aspect of the System Reconstruction technology of the present invention is that it uses organism specific pathways to build maps. This allows the imposition of a condition of self-consistency on the resulting networks. This means that each metabolite should either be essential for the organism (e.g., consumed through food) or there should be a pathway that produces it. In other words, if there is a gap between two nonessential compounds, this implies a lack of knowledge and serves to direct further research. This allows the prediction of the existence of an enzyme function in an organism even if organism-specific genes or proteins have not been identified. For example, when there is a clear gap between two metabolites in the reconstruction that cannot be filled in by any of the described enzymes, it is predicted that there is at least one undescribed enzyme that bridges this gap. In the present reconstruction of amino acid metabolism in humans, several human enzymes were identified that had not been previously identified in the human genome. These enzymes, including amino carboxymuconate-semialdehyde decarboxylase (EC 4.1.1.45) and imidazolone-5-propionate hydrolase (EC 3.5.2.7), were identified because their functions were required by the logic of the metabolic map. Consequently, human genes for these enzymes were proposed through thorough similarity searches of the human genome and by studying human ESTs.

The self-consistency condition also helps eliminate pathways that might be incorrectly assigned merely on the basis of human enzymes having been identified. One example can be illustrated with phenylalanine biosynthesis. It is well known that humans cannot synthesize this essential amino acid. However, there is a human enzyme, aspartate transaminase (EC 2.6.1.1), that could potentially synthesize phenylalanine from phenyl pyruvate. Simply superimposing the human enzyme onto a general metabolic map would lead to the incorrect conclusion that there is a human pathway for phenylalanine biosynthesis. In contrast, the self-consistent reconstruction of the present invention shows that the absence of phenyl pyruvate, the substrate for aspartate transaminase, makes biosynthesis of phenylalanine improbable in humans.

Examples 1 through 4 illustrate pathways in which chitinase is involved. These pathways have been elucidated through the use of the System Reconstruction technology.

Another important feature of the System Reconstruction technology is its potential to predict novel human pathways that have not yet been discovered. Indeed, only a fraction of human functional pathways have been described experimentally. There are still many unknown regulatory, signaling, and even metabolic pathways. At present, there are about 2,000 identified human enzymes. According to both Celera and the Public Human Genome Project Consortium, about 10% of human genes are involved in metabolism. Therefore, humans may have 3,000 metabolic enzymes in total. Thus, approximately half of the human metabolic enzymes may still need to be identified. System Reconstruction technology enables the proposal of many of these undiscovered human enzymes in the course of creating functional tissue-specific maps. The architecture of the map, including identified pathways, compounds that have been synthesized by these pathways, as well as additional evidence from literature and biological high-throughput data can point to enzymatic functions that are required for the self-consistency of the model, thus identifying undiscovered enzymes.

Figure 39:
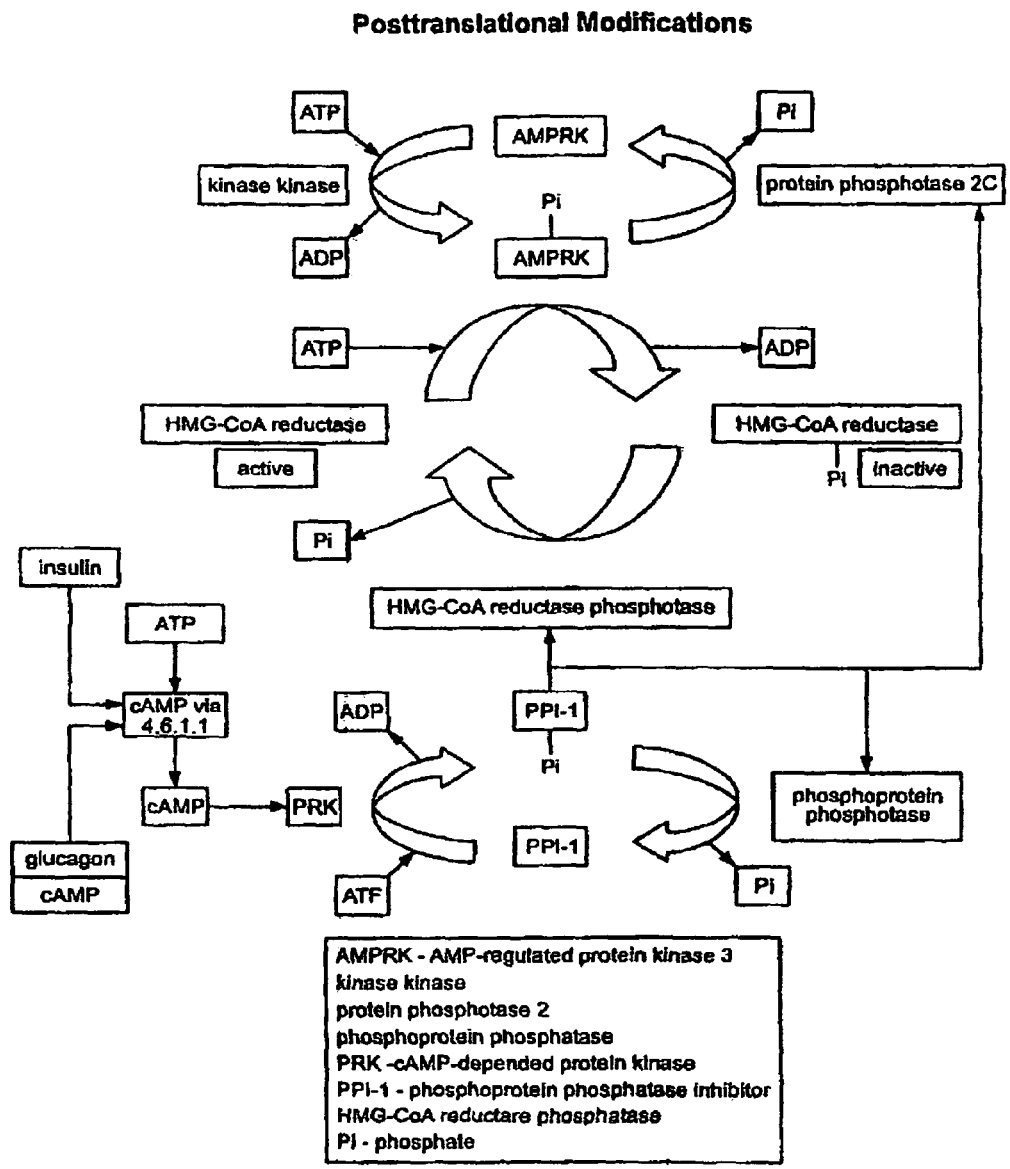
FIG. 39 is a schematic diagram of Post-Translational Modifications.
Figure 40:
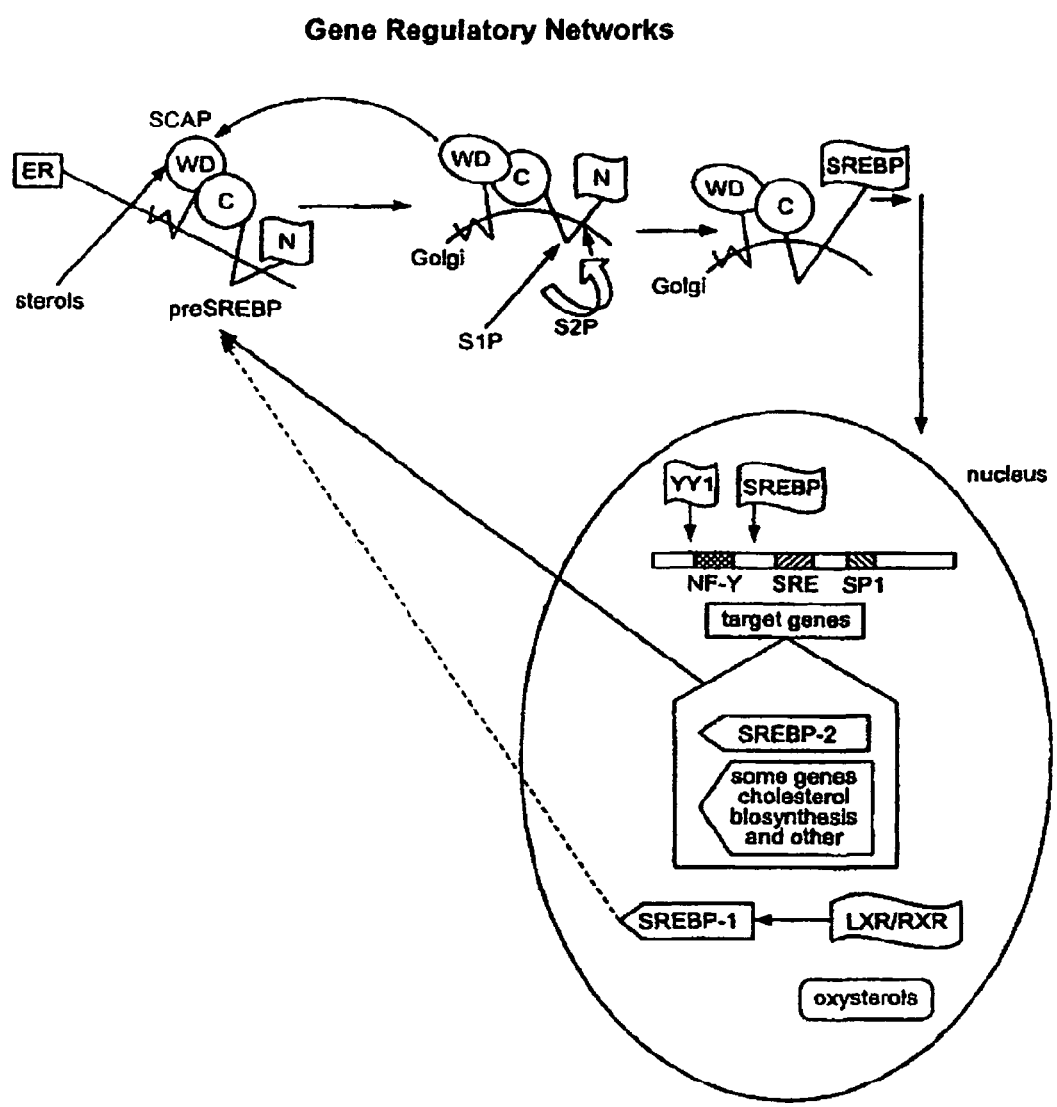
FIG. 40 is a schematic diagram of Gene Regulatory Networks.
Figure 41A:
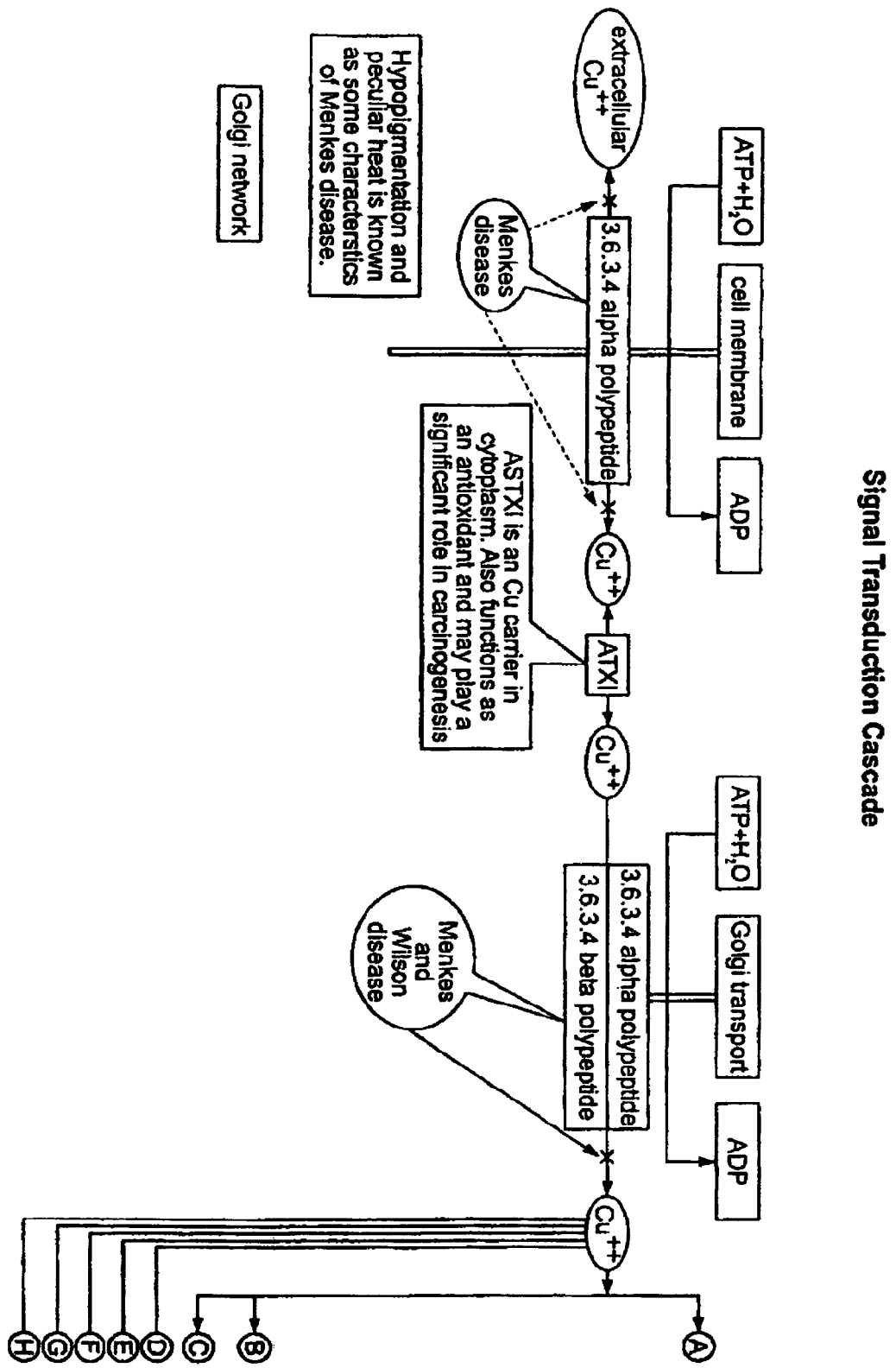
FIG. 41A is a schematic diagram of Signal Transduction Cascades.
Figure 41B:
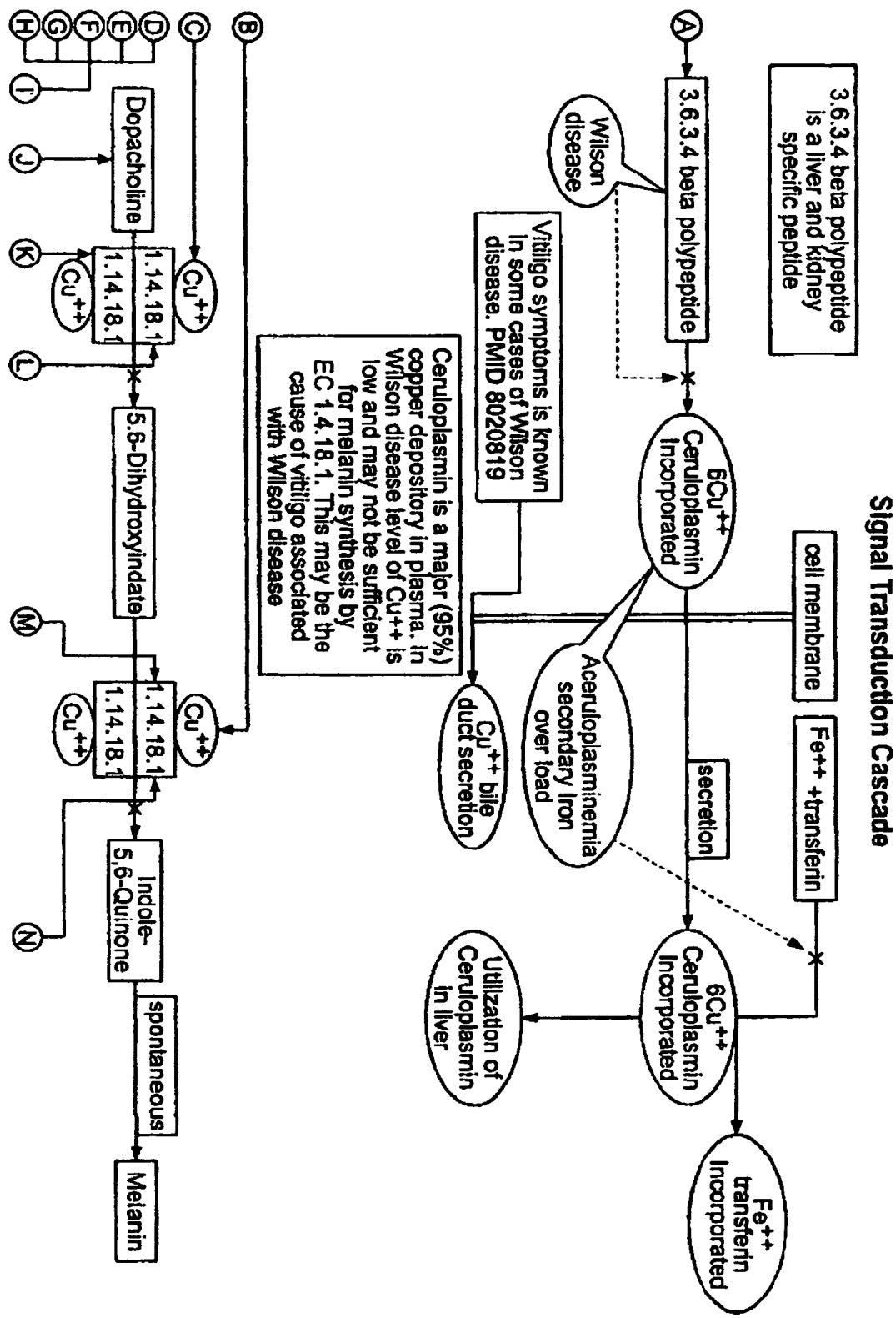
FIG. 41B is a schematic diagram of Signal Transduction Cascades continued from FIG. 41A.
Figure 41C:
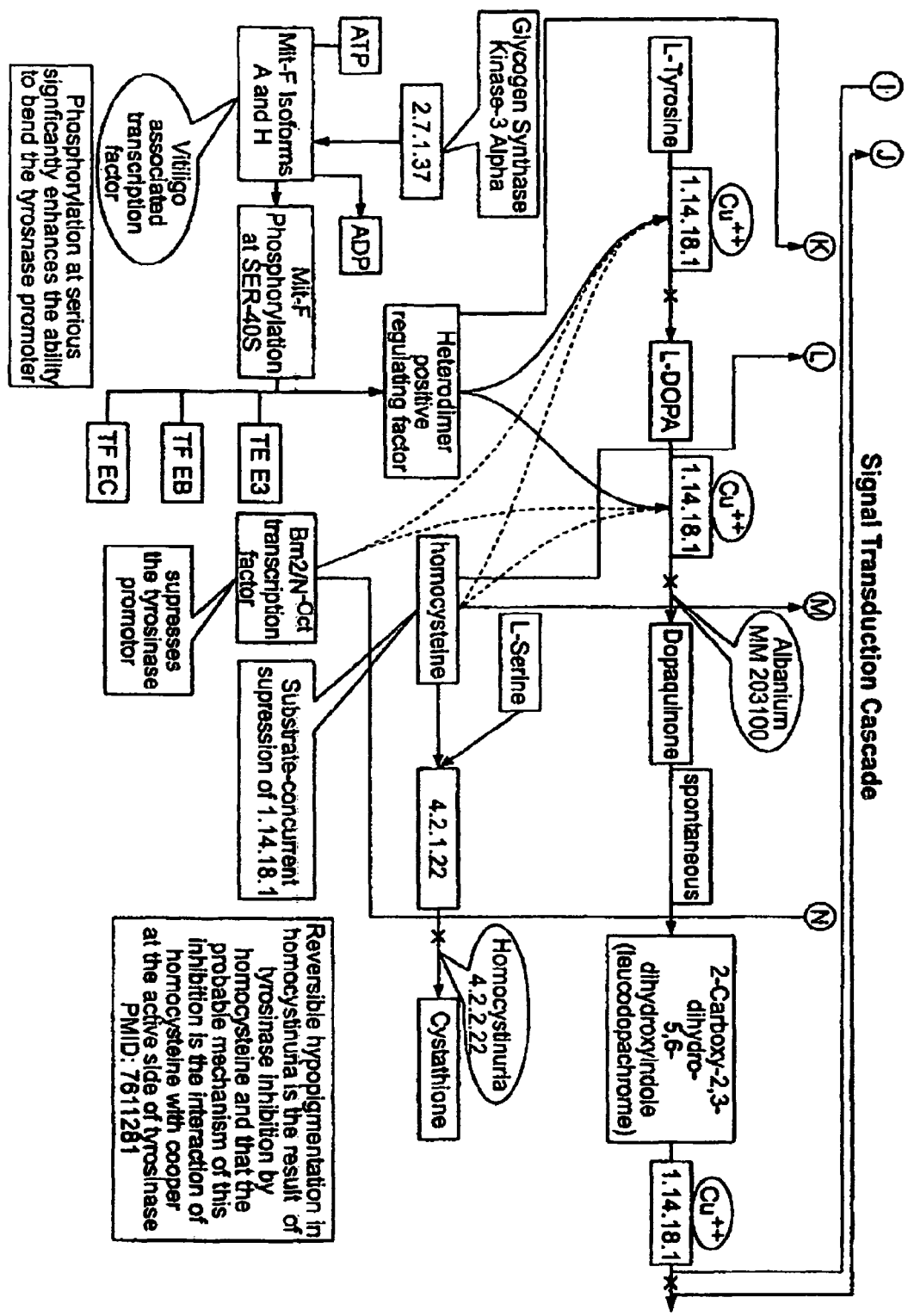
FIG. 41C is a schematic diagram of Signal Transduction Cascades continued from FIGS. 41A and 41B.
Figure 42A:
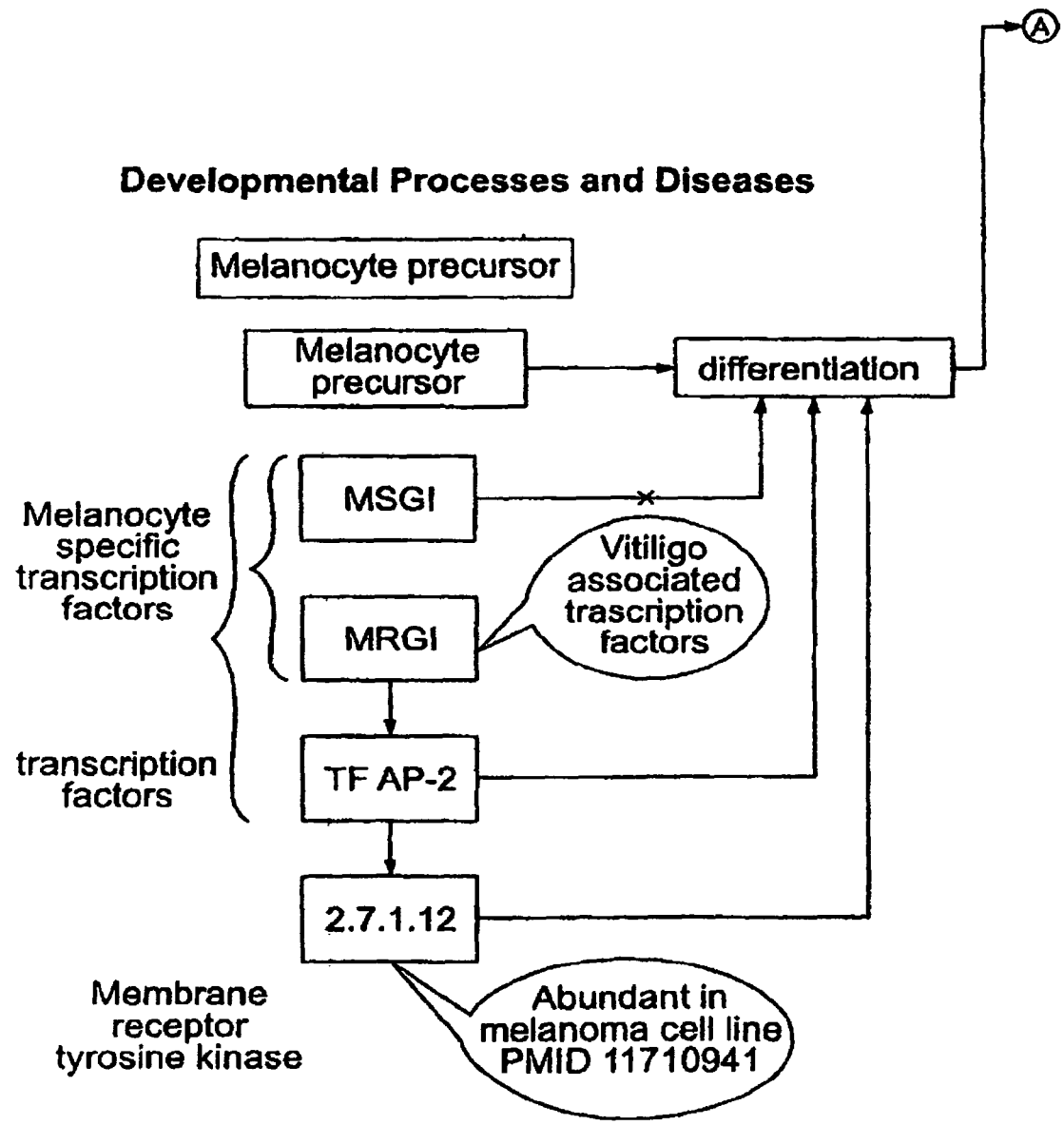
FIG. 42A is a schematic diagram of Developmental Processes and Diseases.
Figure 42B:
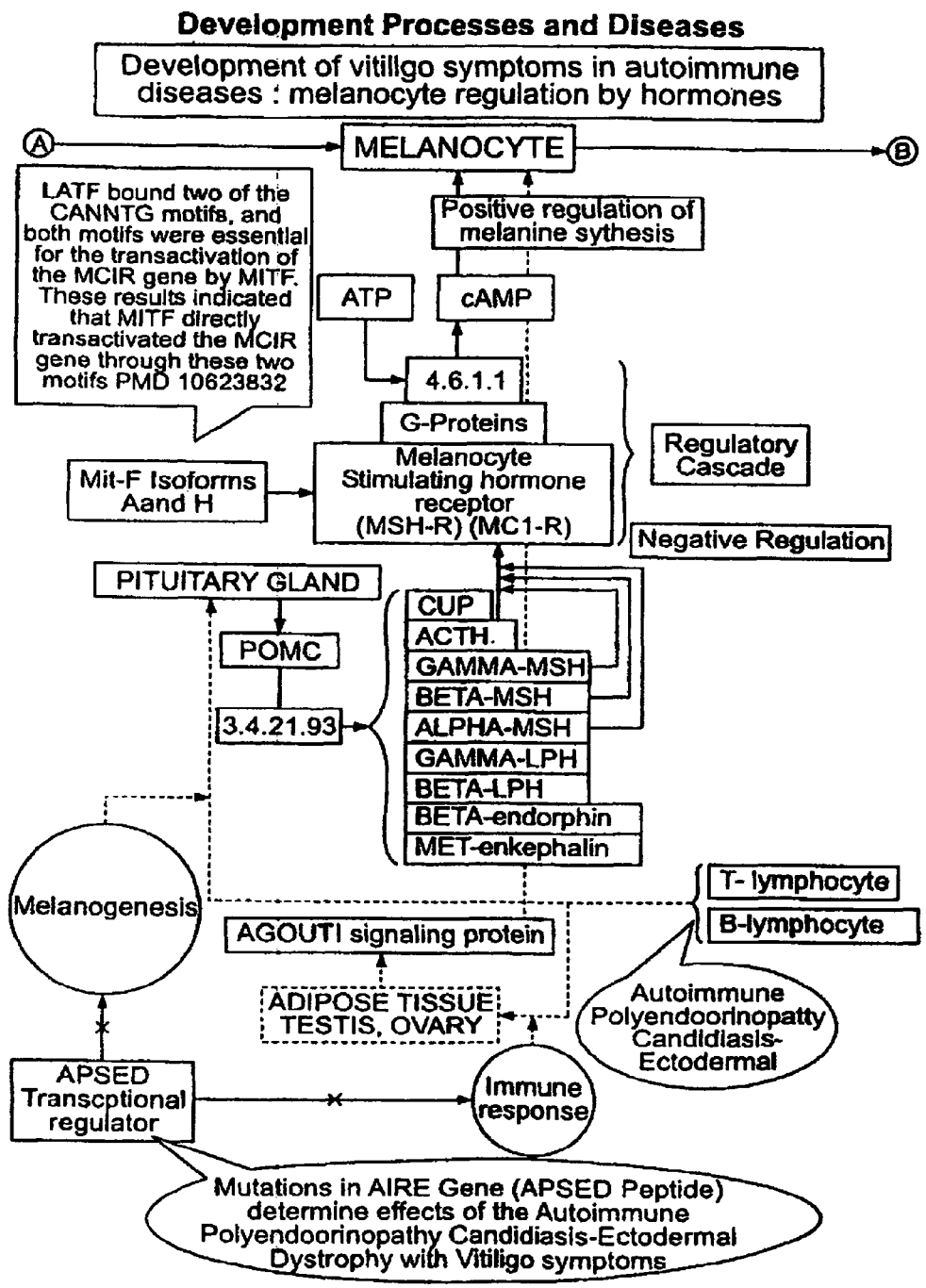
FIG. 42B is a schematic diagram of Developmental Processes and Diseases continued from FIG. 42A.
Figure 42C:
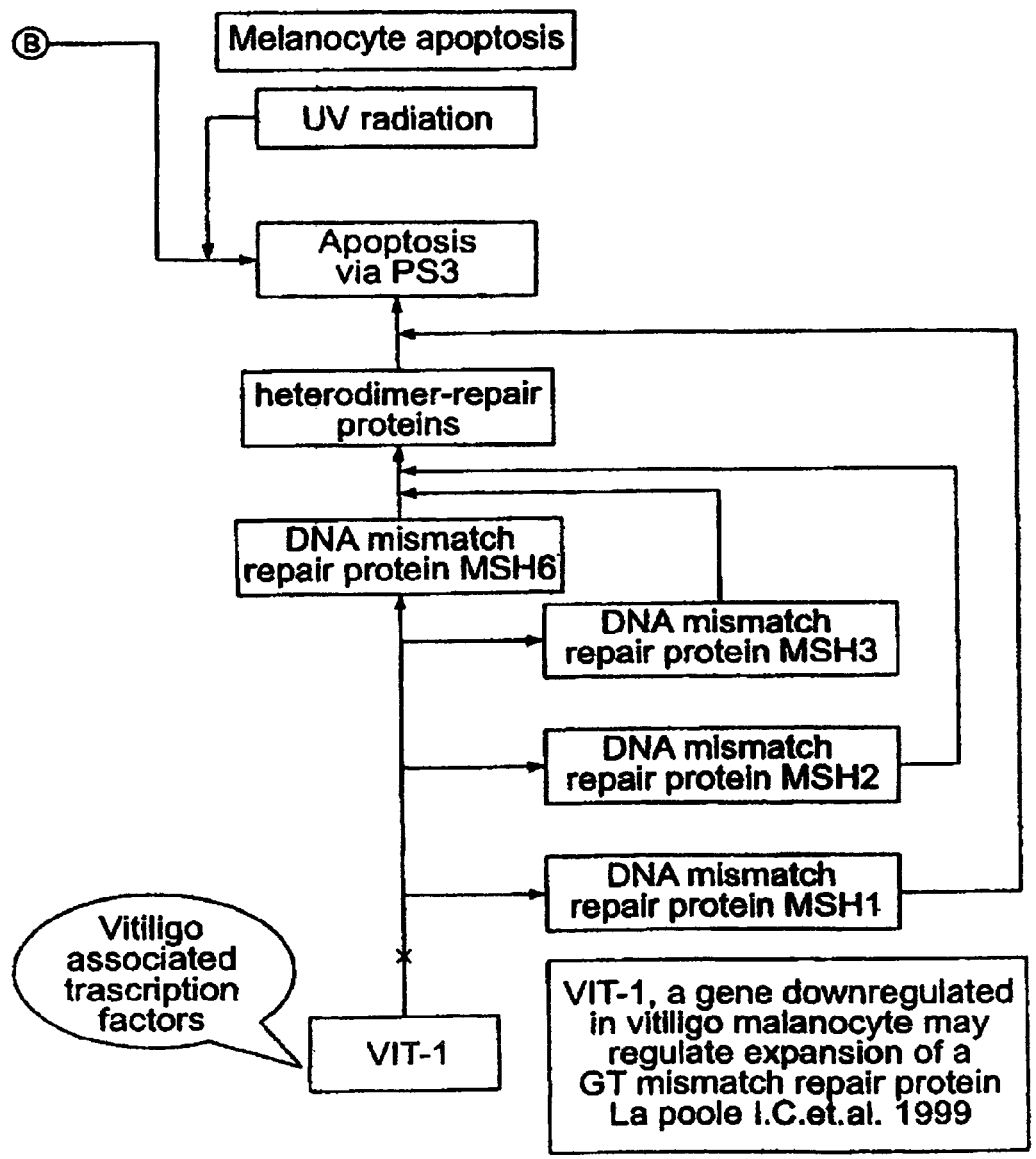
FIG. 42C is a schematic diagram of Developmental Processes and Diseases continued from FIGS. 42A and 42B.
Figure 43:
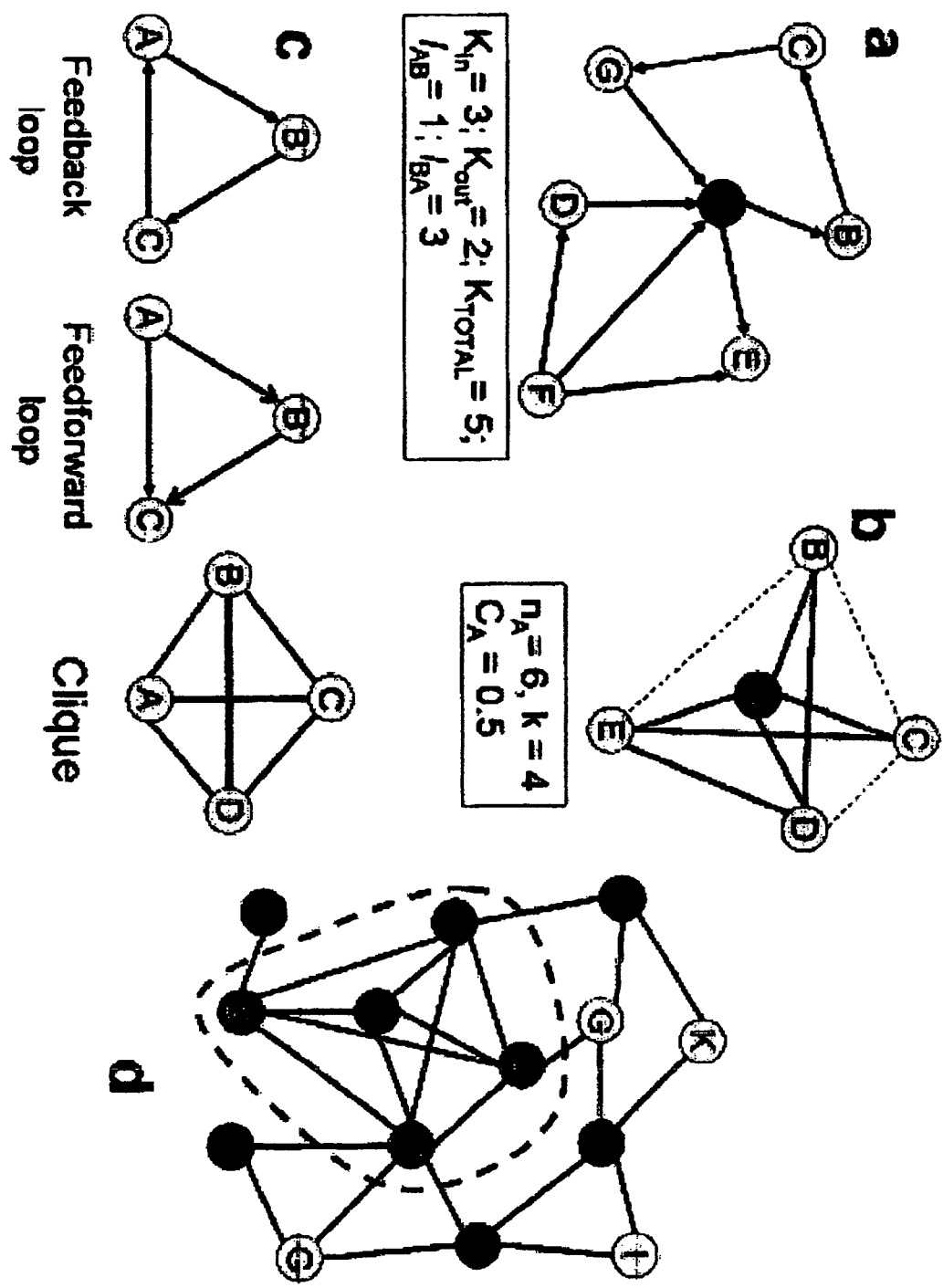
FIG. 43 is a representation of various network architectures and analyses according to various embodiments of the invention.

In one preferred embodiment of the present invention, the subject of System Reconstruction is human metabolism. System Reconstruction can be used to study diverse processes including, but not limited to, amino acid metabolism; carbohydrate metabolism; lipid metabolism; hormones; DNA, RNA, and nucleotide metabolism (see, FIG. 40); aromatic compound metabolism; porphyrin metabolism; coenzyme and prosthetic group metabolism; regulation of metabolism (see FIGS. 36A-C, 37, and 38), posttranslational modifications (see FIG. 39); signal transduction (see FIG. 41A-C); developmental processes (see FIG. 42A-C); and the like. In addition to studying diverse processes, System Reconstruction is useful for integrating these diverse processes and identifying the relationships and interconnections between them (see FIGS. 36-43).

Generally, a formal network would contain reactions that are linked by shared metabolites. In System Reconstruction, pathways are also confirmed through a process of annotation. System Reconstruction allows building of both formal networks, which may contain putative pathways, as well as reconstructed pathways that have been confirmed through a process of annotation.

Figure 6:
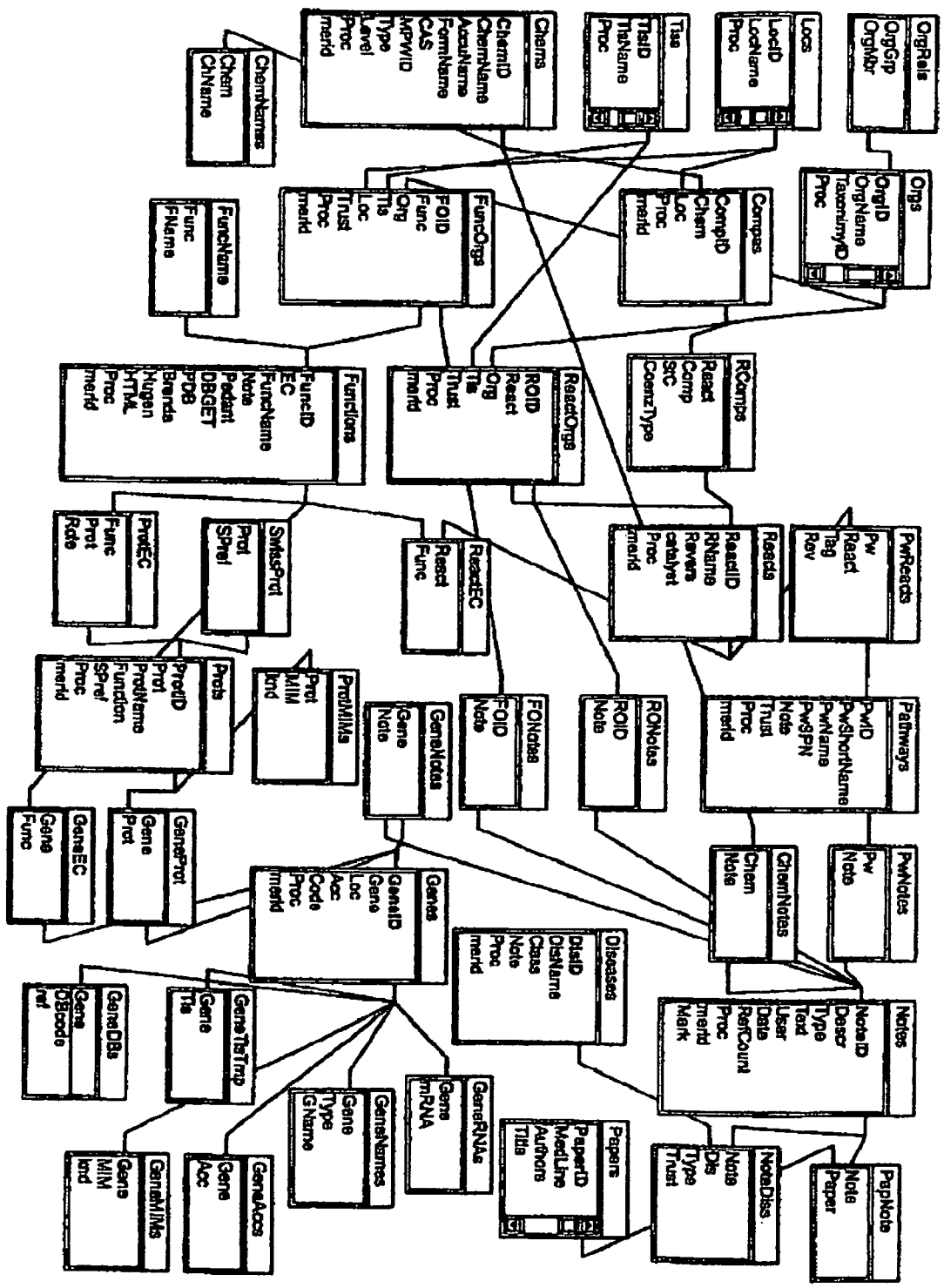
FIG. 6 is a chart illustrating a preferred structure of a System Reconstruction database according to the present invention.

One example of a database architecture according to the present invention is illustrated in FIG. 6. FIG. 6 is a chart showing the some of the types of information that can be made available in a System Reconstruction database as well as some of the interconnections between the various types of information. Example 2 shows how this type of database architecture is reflected in the used interface. The categories of information shown in FIG. 6 relate to an entity in the database and are described briefly as follows:

Orgs, and OrgRels includes information about the organism and its taxonomic classification;

Locs includes information about the sub-cellular localization;

Tiss includes information about the tissues and organs in which the entity is present;

Chems, and ChemNames includes information about chemical compounds, their names, and synonyms;

Compas includes information about unique combinations such as a chemical and its sub-cellular localization (for example, glucose in cytoplasm);

Reacts includes information about reactions;

Rcomps includes information about links between the Reacts and Compas categories (for example, a chemical formula or reaction and its sub-cellular localization);

ReactOrgs includes information about organisms and tissues in which a reaction occurs;

Functions, and FuncNames includes information about enzymes, their EC numbers, their names, and their synonyms;

FuncOrgs includes information about organisms, tissues in which an enzyme is present as well as information about sub-cellular localizations;

ReactEC includes information about links between enzymes and reactions, showing which enzyme(s) catalyze a given reaction;

Pathways includes information about pathways, or sequences of several reactions;

PwReacts includes information about the reaction composition of a pathway;

Prots includes information about proteins, including the name and function of the protein;

ProtEC includes information about which human proteins correspond to a given function (EC number);

SwissProt, and ProtMIMs provide links to external protein databases;

Genes, and GeneNames include information about genes, their names, and their functions;

GeneProts, and GeneEC includes information about links between genes, proteins and EC numbers;

GeneRNAs, GeneDBs, GeneMIMs, and GeneAccs provide links to external genetic databases;

GeneTisTmp includes information about tissues and EST sources for a gene;

PwNotes, ChemNotes, RONotes, FONotes, and GeneNotes provide links between notes (annotations), pathways, Chems, ReactOrgs, FuncOrgs, and Genes;

Notes includes information about notes and annotations;

PapNote, and Papers provide references for each note;

NoteDiss, and Diseases include information about how diseases are linked to a note, for example, whether a certain entity is thought to be a cause or manifestation of a disease, or is hypothesized to be involved in a disease.

There are multiple ways for elucidation of protein-protein interactions. One approach is to apply text-mining algorithms for screening experimental literature for co-occurrence (therefore, association) of gene/protein symbols and names in the same text. Typically, Natural Language Processing algorithm (NLP) is used for automated mining abstracts and titles of PubMed articles. The reliability of NLP-derived associations can be enhanced by compilation of field-specific synonym dictionaries, using longer word strings for search and full-text articles to query against. In a recent study, the NLP engine MedScan was used to extract 2976 interactions between human proteins from full text articles with a precision of 91% for 361 randomly extracted protein interactions. However, the comparative studies show that, in general, only 30-50% of NLP associations corresponded to experimentally verified protein interactions.

Protein-protein interactions can also be derived from high-throughput experimentation. For example, the yeast 2-hybrid (Y2H) screen test identifies protein pairs capable of dimerization in yeast cells. A widely used wet lab technique, Y2H was scaled-up for global mapping of protein interactions in yeast, fly *D. melanogaster* and worm *C. elegans*. Y2H became the technology base for several tools and discovery companies such as Curagen (www.curagen.com) and Hybrigenics (www.hybrigenics.fr). However, Y2H-derived interactions are known for high (over 50%) level of false positives and false negative interactions. The interactions can also be deduced from condition-specific co-occurrence of gene expression based on the assumption that interacting proteins must be expressed in, especially when encoded by the homologous genes. Abundant and readily obtainable even from small cell populations, co-expression-based clustering is thought to become the major source of tissue-, disease- and treatment-specific interactions. However, the overall confidence in co-expression-derived interactions in yeast is about 50% (47% anti-correlation for novel interactions). Another method, co-immunoprecipitation (Co-IP) consists of affine precipitation of protein complexes in mild conditions using antibodies to one of the complex's subunits, followed by mass-spectrometry or Western blot analysis. A true proteomics method, Co-IP was used in back-to-back studies of yeast interactome. The other, less often used experimental and computational methods include protein arrays, fusion proteins, neighbor genes in operons (for prokaryotic proteins), paralogous verification method (PVM), co-localization, synthetic lethality screens and phage display; each method has its merits and biases. The overall confidence in interactions defined as the intersection between interacting pairs obtained with different methods remains dismal. For instance, over 80,000 protein-protein interactions were detected in yeast *S. cerevisiae* by six high-throughput experimental methods, but only 2,400 of these interactions were supported by more than one method. Such low overlap limits the applicability of direct comparison between HT interactions datasets of different experimental origin. Recently, statistical methods were developed for enhancing the confidence of interactions derived from low confidence data and analyzing the general parameters of interaction datasets. Y2H and Co-IP yeast protein interaction data applied in yeast were extensively compared for experimental biases and correlation. Although only 6% of Y2H interactions were confirmed by Co-IP method, the authors managed to develop a statistical regression model for prediction of biological relevance and confidence of HT interactions based on sub-network analysis. In another study, graph-theoretical statistics were used for comparative analysis of the interaction datasets in yeast. The parameters and algorithms were realized in the publicly available tool TopNet for comparison of biological sub-networks of different origin (networks.gersteinlab.org/genome/interactions/networks/core.html). In general, it is believed that only manually curated physical protein interactions extracted from original small-scale experimental literature can be used with sufficient confidence.

Dozens of the original and compilation academic protein-protein and protein-DNA interaction databases are available, covering high-throughput and small-scale experimental interactions as well as other experimentally and computed interactions. The most relevant and original database projects, pathways database and analytical tools are outlined in Table 5.

Biological networks are presented as nodes (proteins, genes and compounds) connected by edges (protein-protein, protein-gene, protein-compound interactions and metabolic reactions). Depending on the type of underlying data and the interaction mechanism, the edges are either directed or undirected. For instance, protein binding interactions derived from Y2H assays are undirected, while most of the physical interactions extracted from full text articles have one direction (e.g., protein A activates protein B, but not vice versa). There are several major parameters by which networks can be described and compared (FIG. 43a) including the following.

1) Average degree (K): the average number of edges per node. In directed networks one can distinguish incoming degree ($K_{in}$), outgoing degree ($K_{out}$) and total degree.
2) Average clustering coefficient (43c): the average ratio of the actual number of links between the node's neighbors and the maximum possible number of links between them. Clustering coefficient for the node i can be calculated as $Ci=2n_i/k(k-1)$, where $n_i$ is the actual number of links connecting k neighbors of the node to each other FIG. 43b.
3) Shortest path $l_{AB}$ for the pair of nodes is the minimum number of network edges that need to be passed to travel from A to B. On a directed graph the shortest path from A to B may be different from the path from B to A as shown on FIG. 43a. Characteristic path length (L): the average length of shortest paths for all pairs of nodes on the graph.
4) Diameter (D) is the longest distance between a pair of nodes on the graph.

The default random network theory states that pairs of nodes are connected with equal probability and the degrees follow a Poisson distribution. This implies that it is very unlikely for any node to have significantly more edges than average.

The analysis of yeast interactome (the best studied organism in terms of interactions) revealed that the networks are remarkably non-random and the distribution of edges is very heterogeneous, with few highly connected nodes (hubs) and the majority of nodes with very few edges. Such topology is defined as scale-free, meaning that the node connectivity obeys power law: $P(k) \sim k^{-\gamma}$, where and P(k) is the fraction of nodes in the network with exactly k links. Interestingly, the hubs are predominantly connected to low-degree nodes, a feature that gives biological networks the property of robustness. A removal of even substantial fraction of nodes still leaves the network connected. At the level of global architecture, networks of different origin (e.g. metabolic, regulatory, protein interactions, networks for different organisms) share the same properties. Taken together, the metabolic reactions and signaling interactions form a large cluster linked via molecular nodes shared among many cellular processes. This runs contrary to a traditional model of small and relatively independent linear pathways.

The key property of biological networks is their modular nature. According to modular theory, various types of cellular functionality are provided by relatively small, transient but tightly connected networks of molecules (5-25 nodes) that are engaged in performing specific functions. Identification of such modules is a non-trivial problem as complex networks can be parsed into subsets in many different ways, potentially generating billions of combinations. For example, our analysis of the network of a subset of 35,000 experimentally proven human signaling interactions in the MetaCore™ database revealed about 2 billion linear 5-step network paths, all physically possible. It is clear that only few of these paths are realized in any cell and time as active pathways.

Different approaches have been offered for automated parsing of large networks into modules. One set of methods identifies the modules using various clustering algorithms. These include Monte Carlo optimization methods for finding tightly connected clusters of nodes; clustering based on shortest paths length distribution, and other graph clustering algorithms. It has been shown that some clusters identified in this way do in fact correspond to either known protein complexes or metabolic pathways. Another approach implies analysis of motifs; fairly simple sub-graphs that share certain structural and functional features, such as a feedback or feed-forward loops. The number of different motifs in a given network is calculated and then compared with the number of the same motifs in a randomly connected network. Those motifs in which the network is enriched when compared to the random network may represent potential functional modules. The motifs were identified in regulatory networks of E. coli and yeast. It should be noted that performance of these algorithms is usually judged by how well they can recall the known functional units or processes. On this account, all of these algorithms are prone to a high level of false-positives: the modules not corresponding to any of known pathways.

Conditionally active functional modules can also be elucidated by the analysis of high-throughput molecular data (e.g., gene expression, protein abundance, metabolic profiles) in the context of networks. One straightforward approach relies on statistical clustering of gene expression data followed by mapping the resulting clusters onto the networks obtained from independent sources. The advantage of this approach is the prioritization of gene clusters base on the number of links to the network. The drawback is that the statistics-derived clusters are inherently artificial and can be connected to multiple networks and cellular processes. In another method, the network clustering algorithms such as super-paramagnetic clustering are used to identify tightly connected sets of nodes. The expression data helps to assign weights to the edges and nodes; the combined distance is then computed based on both expression profiles and the network distance between gene products. Other methods include simulated annealing and probabilistic graphical models. Essentially, analysis of molecular data within the context of interaction networks reveals genes/proteins that share a similar pattern of expression and at the same time are closely connected on the network (FIG. 43d). Another important way of finding putative functional pathways is by comparison of networks derived from different data sources. For example, a heuristic graph comparison algorithm was developed for finding functionally related enzymes clusters (FRECS) across bacterial species and between protein and gene expression networks. Another algorithm allows one to identify common interaction pathways by inter-species alignment of protein interaction networks, e.g., between yeast S. cerevisiae and bacterium H. pylori.

The non-random nature of biological networks is associated with biological functions of nodes and edges. Recently, several studies in yeast revealed correlations between the network topology and composition with important biological properties of nodes' proteins. The well-connected hubs (defined here as the top quartile of all nodes in terms of the number of edges) are largely presented by evolutionary conserved proteins as the interactions impose certain structural constrains on sequence evolution. In both yeast S. cerevisiae and worm C. elegans, a significant negative correlation was shown between the number of interactions and the relative evolutionary rate. Recently, it was revealed that the number of interactions positively correlates with essentiality in yeast. Essential and marginally essential (relative importance of a non-essential gene to a cell) genes tend to be hubs with short characteristic path length to the neighbors. Essential proteins tend to be more closely connected to each other. Furthermore, essential proteins tend to be the more promiscuous transcription factors, and the target genes regulated by fewer transcription factors, tend to be essential. Many of these targets are housekeeping genes with high expression levels and less expression fluctuation. It was also noted that soluble proteins feature more interactions than membrane proteins. As mentioned above, the links between highly connected and low-connected pairs of proteins define the specific topology of the networks, characteristic for the condition. In yeast, the direct links between highly connected hubs are suppressed and the hub—low connected node pairs are favored. Such topology probably prevents crosstalk between the functional modules and sub-networks. The findings may have substantial implications for the practice of drug discovery in terms of target prioritization and identification of multi-gene/multi-proteins biomarkers.

Figure 44:
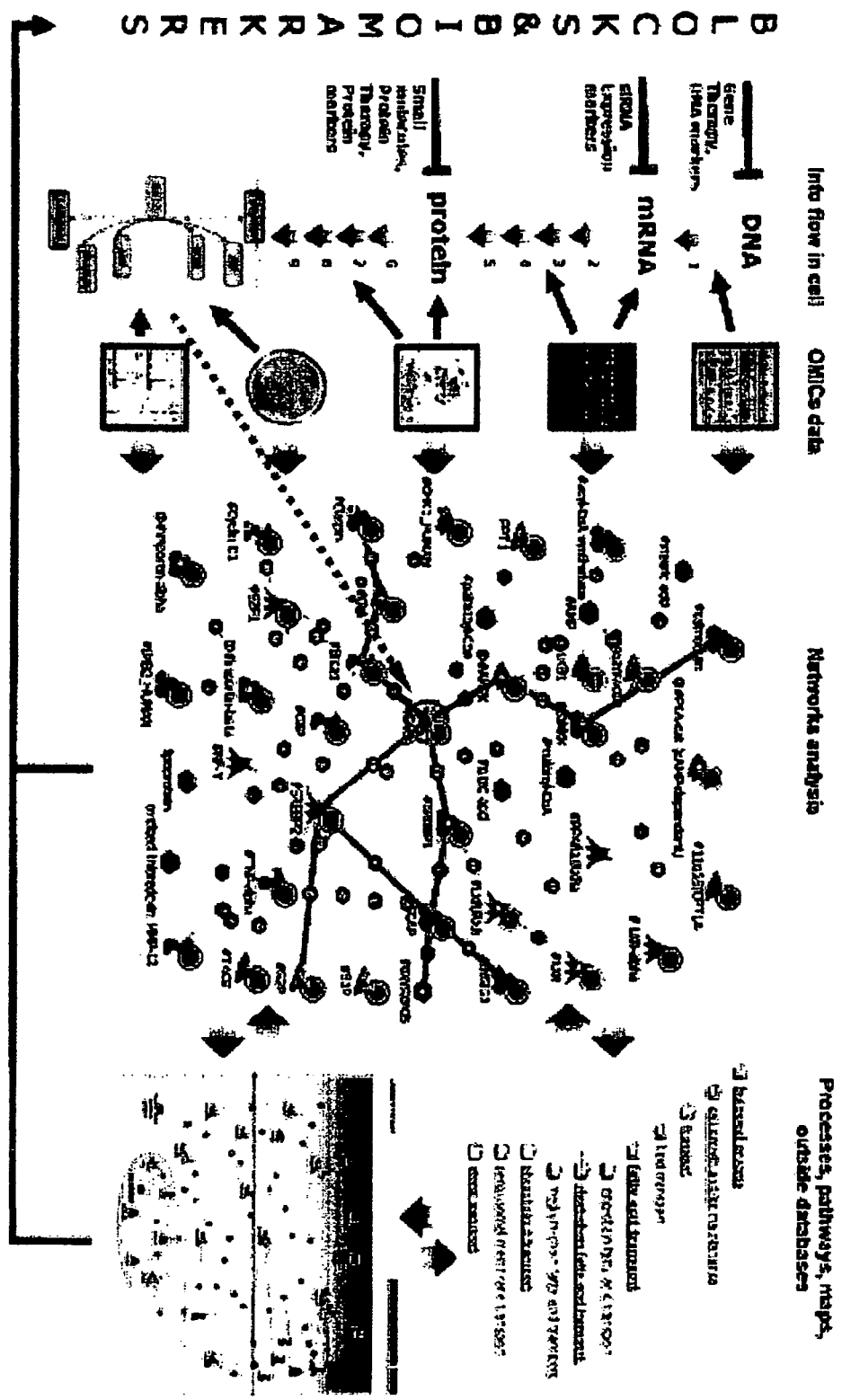
FIG. 44 is a general schema of network analysis of HT data according to one embodiment of the invention.

Biological networks are the most suitable tool for functional mining of large, inherently noisy experimental datasets such as microarray and SAGE expression patterns, proteomics and metabolomic profiles. There is an important distinction between networks and the other methods available for HT data analysis (such as statistical clustering, linking to pathway databases, process ontology, pathway maps, cross-species comparisons etc.). Unlike other methods, networks' edges provide primary information about physical connectivity between proteins, their subunits, DNA sequences and compounds. The complete set of interactions which assembles into networks on-the-fly, defines the potential of a cell to form multi-step pathways, signaling cascades and protein complexes representing the core machinery of cellular life in health and disease. Obviously, only a fraction of all possible interactions is activated at any given condition as only some of the genes are expressed in tissues at a time and only a fraction of the cellular protein pool is active. The subset of activated (or repressed) genes and proteins are captured by OMICs experiments, such as global gene expression profiles, proteomics or metabolomics profiles—the functional snapshots of cellular response. Analyzed separately, these datasets cannot explain the whole picture. There are many levels of information flow between a gene and an active protein it encodes, including gene expression, mRNA processing, protein trafficking, posttranslational modifications, folding and assembly into active complexes (FIG. 44). Eventually, active proteins perform certain cellular functions (such as a metabolic transformation of malonyl into acetyl-CoA in this example), which can be presented as one-step interactions in the space of thousands of metabolic transformations regulated at multiple levels from the cell membrane receptors to transcription factors. The intersection of the experimental data with the interactions content on the networks (derived from experimental literature) provides the closest possible view of the activated cellular machinery in a cell—either signaling or metabolism. As all objects on the networks are annotated, they can be associated with one or more cellular functions, such as apoptosis, DNA repair, cell cycle checkpoints or fatty acid metabolism. The networks can be interpreted in terms of these higher level processes, and the mechanism of an effect can be unraveled. This is achieved by linking the network objects to GO (The Gene Ontology Consortium) and other process ontologies, metabolic and signaling maps (FIG. 44 and Table 5). The networks can be scored based on statistical relevance to the functional processes and maps or relative saturation with the uploaded data. Experimental adjustment can be done by choosing tissue, disease, experiment specific interactions, removing and adding specific interactions mechanisms, linking orthologous genes from other species, etc. The networks can also be connected to outside databases and HT data analyzing software. The outcome of such systemic analysis can be new hypotheses on the critical bottlenecks in the disease pathways (potential drug targets) or conservative interactions modules supported by HT data (possible biomarkers) (FIG. 44).

Figure 45:
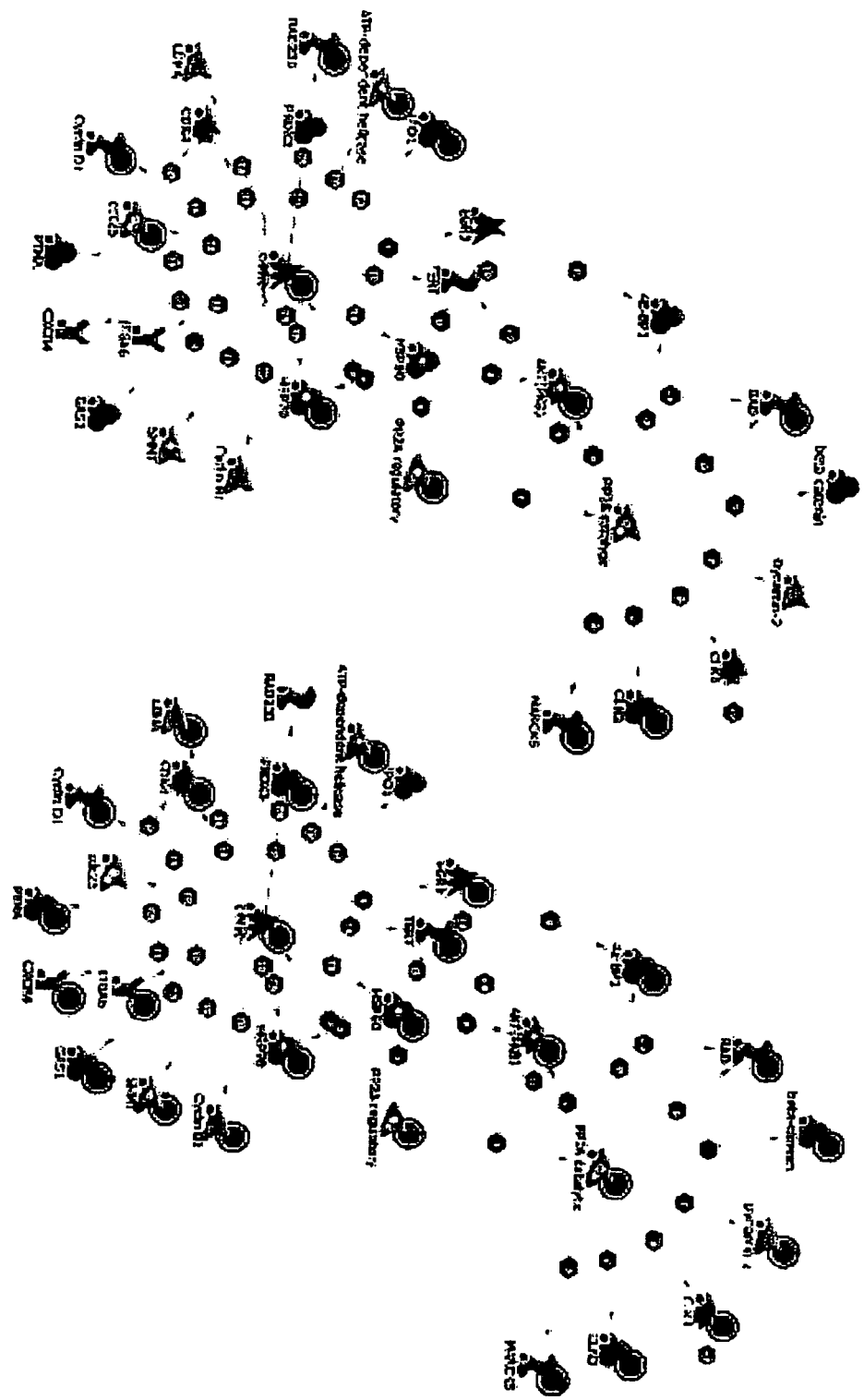
FIG. 45 is a representation of gene expression in mammary gland epithelium on the same network as measured by the SAGE method.

Networks represent a flexible and powerful analytical tool for comparison and cross-validation of different types of datasets associated with a condition (disease, drug treatment etc.). In fact, any experimental or literature-derived dataset with recognizable gene or protein IDs (such as LocusLink, Unigene, SwissProt, RefSeq, OMIM) can be visualized, mapped and compared against each other on the same network. For example, one can directly compare the list of genes known from genetics analysis with the gene expression arrays from a patient in clinical trials and a knockout mouse. When the same data type and experimental platform is used, the conditional networks can be compared in great detail for common and different sub-networks and patterns. Such fine mapping can be performed in order to compare the tissue and cell type specific response, different time points, drug dosage; different patients from the same cohort, etc. For instance, we have compared gene expression patterns from mammary gland duct epithelium of two breast cancer patients, one from pre-invasive DSIC stage, another with invasive cancer. Both data sets were used for building the initial networks, and then visualized separately. One of the top-scoring networks included the major cell proliferation activator oncogene c-Myc (FIG. 45). One can see that the expression pattern for invasive cancer (B) features many more up-regulated genes in immediate vicinity of c-Myc. The leading integrated network analytical suites are well equipped with a range of tools and algorithms for such analyses (Table 5).

Figure 46A:
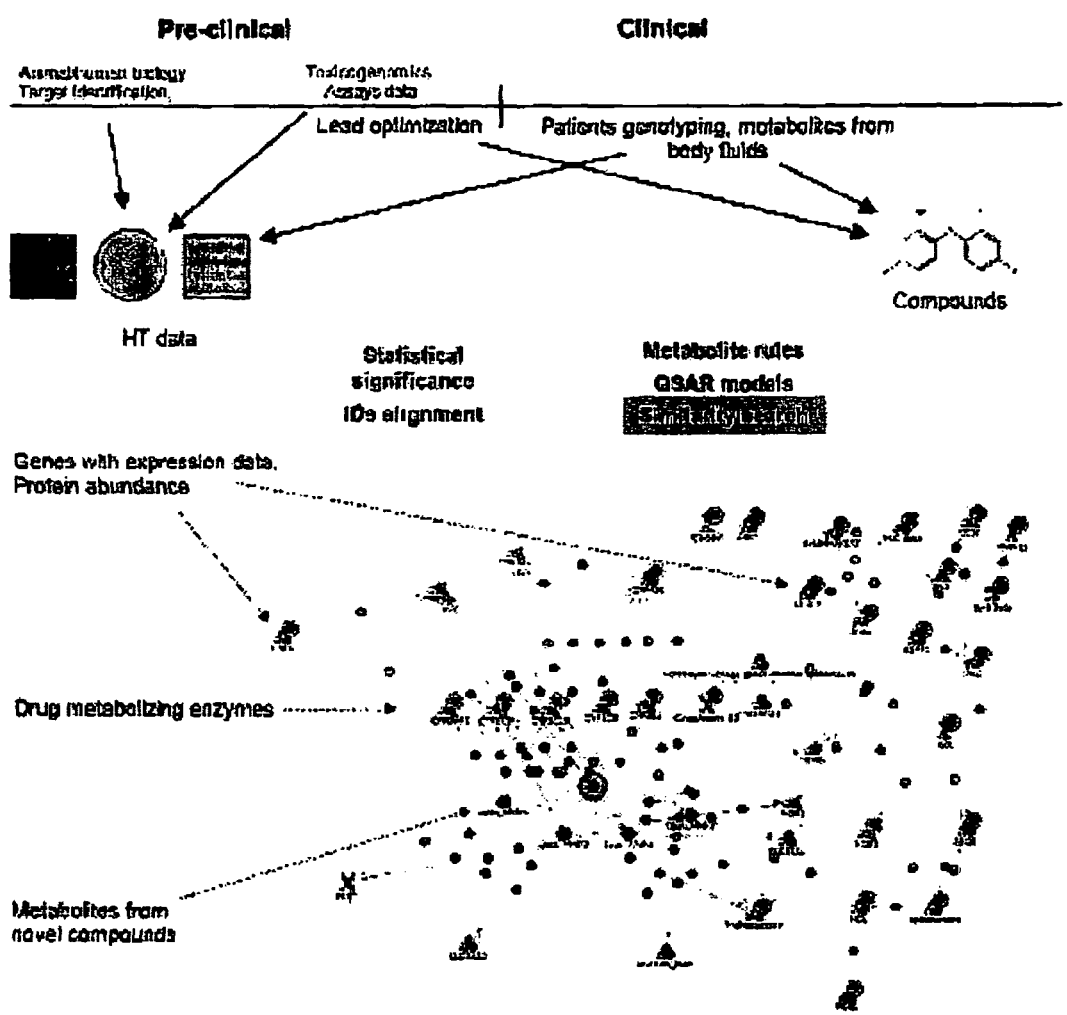
FIG. 46 is representations of applications of network analysis in drug development according to one embodiment of the invention.
Figure 46B:
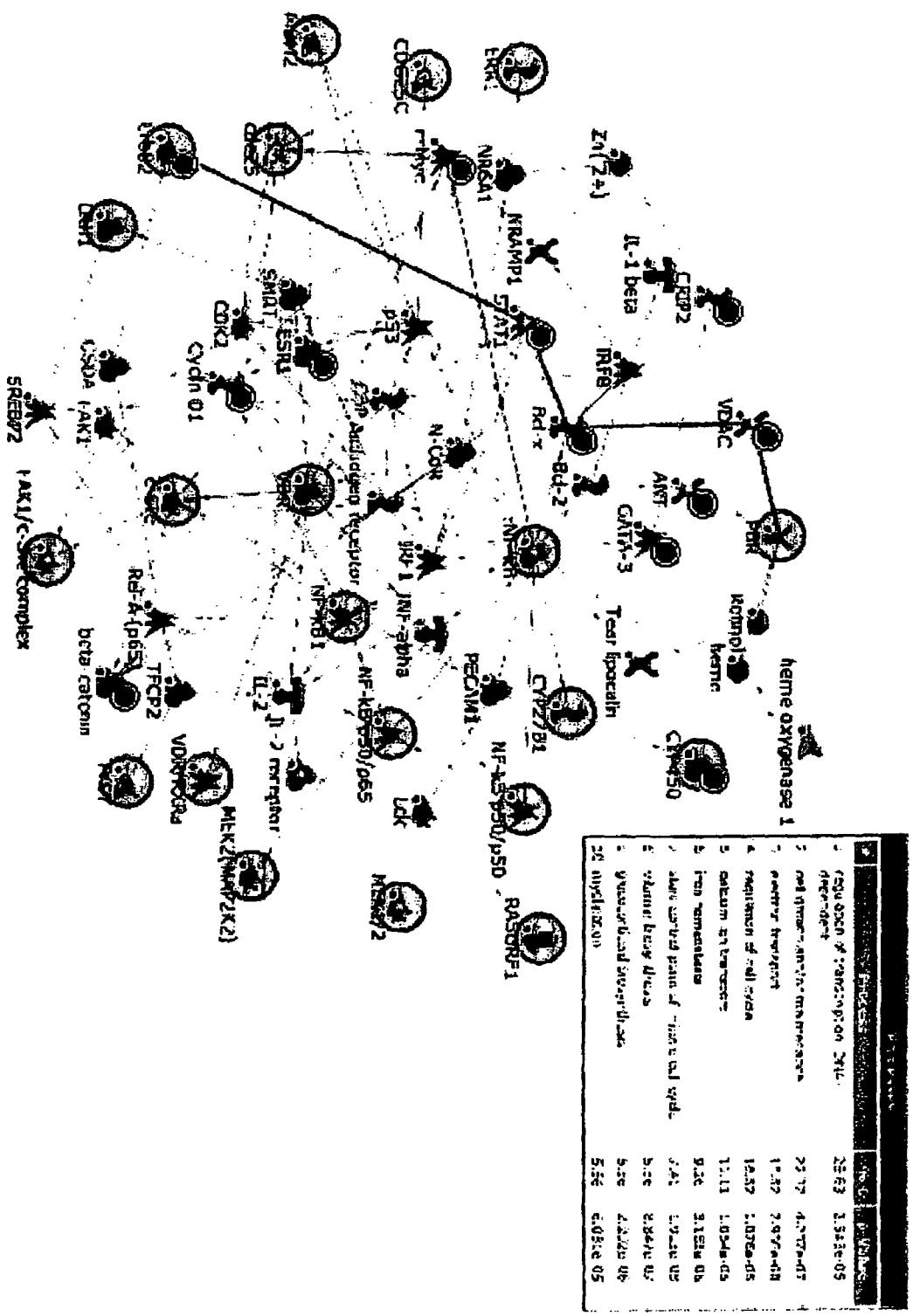

Networks analysis is broadly applicable throughout the drug discovery and development pipeline, both on the biology and the chemistry side. Basically, any type of data which can be linked to a gene, a protein or a compound, can be recognized by input parsers, and subsequently visualized and analyzed on the networks. It makes eligible almost any pre-clinical HT experiment as well as patient DNA or metabolic tests from clinical trials (FIG. 46A). Most importantly, all these different datasets (as distant as apples and oranges) can be processed on the same network backbone. Therefore, networks represent the universal platform for data integration and analysis, which has always been the Holy Grail of bioinformatics technology. Network analysis of complex human diseases is a very young area. In one recent study, generic networks automatically generated from literature interactions were applied for elucidation of specific modules around the genes involved in Alzheimer disease, and the scoring procedure for disease-relevant protein nodes was developed. Here we list some of the network analysis applications in drug discovery.

Target identification: Experimental data from model organisms, cell lines and human tissues can be uploaded and mapped on networks. New hypotheses can be made on the pathways connecting the proteins of interest.

Target validation and prioritization: Data cross-referencing on the same networks, maps and pathways.

Disease biomarkers: The biomarkers can be identified as signature networks—condition-specific conserved sets of nodes supported by differential gene expression and protein abundance data.

Toxicity biomarkers: Same as above, with signature networks derived from toxicogenomics data—typically a rat or mouse liver arrays from drug-treated animals.

Pharmacogenomics/haplotyping: The networks modules can be used as a mean for haplotyping SNPs associated with the condition.

Lead optimization and selection of drug candidates: The biology side of small compounds development deals with prioritization of primary indications, possible side effects and ADME/Tox evaluation of novel compounds. New compounds and their metabolites from pre-clinical studies can be mapped on tissue, disease specific metabolic and regulatory networks via structure similarity search with metabolites and ligands included in the database. This functionality is realized in MetaDrug.

Clinical studies: The patients data (specific DNA sequences, expression microarrays, metabolites from body fluids) can be mapped on networks and compared with pre-clinical data and published experiments.

New indications for marketed drugs: Secondary indications is an important part of follow-up development for bioactive compounds. New therapeutic areas can be suggested by analysis of tissue-specific, disease-specific networks from animals and humans treated with the drug.

Post-market monitoring: The patients' data (usually metabolites from body fluids) can be stored in the database and monitored on the networks built during clinical and pre-clinical studies.

Now, we will consider identification of novel therapeutic targets by reverse engineering the network created around existing drug targets. In this case, we used the software suite MetaCore™ previously developed by GeneGo, Inc. In this example, we have uploaded a list of about 40 proteins known as breast cancer therapeutic targets and used this list to build networks with different algorithms applied at MetaCore (shortest path algorithm is presented here). Most proteins have connected into highly concise networks closely associated with cell proliferation and cell cycle progression. Next, we used these networks for mapping published microarray gene expression data from invasive breast cancer patients (the nodes with red circles). The putative novel targets must satisfy the following conditions: 1) connectivity in one step with the known targets, 2) be upstream of known targets in signaling, and 3) condition-specific overexpression.

Figure 46C:
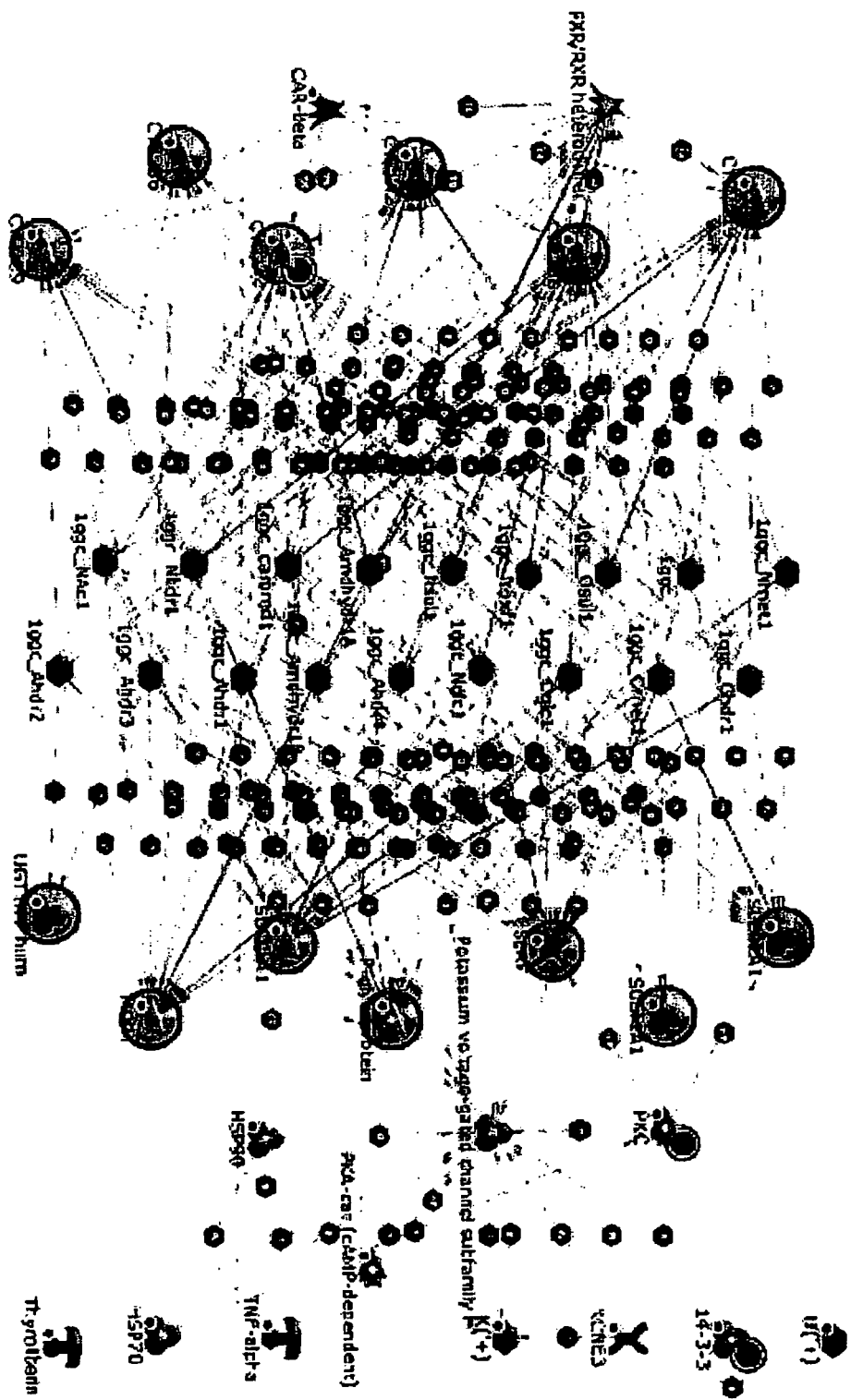

The networks can be used in a similar way for identification of biomarkers. In Example 10 (FIG. 46C), we used networks for evaluation of toxicity and human metabolism of acetaminophen (APAP). The structure was processed in MetaDrug using metabolic cleavage rules and models, and the resulted metabolites were displayed on the networks connected with the metabolizing enzymes. On the same network, we displayed microarray gene expression data from livers of rats intoxicated with high dose of APAP. The resulting networks can be used as a tool for elucidation of the effected signaling and metabolic pathways.

EXAMPLES

Example 1

Stabilization of Heparin for Treatment of Arteriosclerosis

HC gp-39, a protein of the chitinase family, can be used in combination with heparin to treat arteriosclerosis. Addition of HC gp-39 may stabilize heparin and increase its effectiveness.

Heparin appears to play a role in arteriosclerosis. Data shows that patients suffering from arteriosclerosis have decreased heparin levels. ☐ Therapeutic treatment with heparin is used to reduce the risk of infarction and stroke. Heparin is also used as an anti-coagulant. It activates antithrombin-III. Additionally, low molecular weight heparin is used for the treatment of lipid metabolism disorders as an agent that activates lipoprotein lipase.

Under normal conditions, lipoprotein lipase is localized on the cell surface, including the surface of endothelial cells in blood vessels. The binding of heparan sulfate to lipoprotein lipase is responsible for the retention of lipoprotein lipase on the cell surface. While bound to the cell surface, lipoprotein lipase is not enzymatically active, but serves as a receptor, binding low density and very low density lipoproteins (LDL and VLDL). This binding leads to the cellular uptake of lipoproteins (PMID 10532590). Development of arteriosclerosis is characterized by the emergence of so-called foam cells that form due to an excess of lipoproteins being absorbed into the cell through pinocytosis.

Heparin has a higher affinity for lipoprotein lipase than does heparan sulfate. With the exchange of heparin for heparan sulfate binding to lipoprotein lipase, the lipoprotein lipase is activated and released from the cell surface and into the intercellular space and to the blood (PMID 11427199). While the binding of heparin activates lipoprotein lipase, in the absence of heparin, even if lipoprotein lipase is released from the cell surface, it remains inactive (PMID 10760480).

The binding of heparin to lipoprotein lipase results in several positive therapeutic effects. First, the uptake of lipoproteins by cells is decreased and, therefore, further formation of foam cells is prevented. Second, heparin-bound lipoprotein lipase regains its catalytic activity (PMID 210908, 698674) and starts to degrade LDL and VLDL in the intercellular space and in the blood. An excess of LDL and VLDL in the blood leads to the formation of atherosclerotic plaques. In contrast, degradation of LDL and VLDL by lipoprotein lipase leads to the formation of fatty acids that are eventually processed in the liver. Therefore, the degradation of LDL and VLDL by lipoprotein lipase helps prevent the development of arteriosclerosis.

As mentioned above, patients with arteriosclerosis are often treated with heparin. Free heparin is thought to be degraded by heparinase. A full length human heparinase enzyme has not been isolated. Human heparinase is known only by fragments of its sequences (NCBI protein # AAE10146-10153, ME13758-13770, AAE67749-67785). While the enzymatic activity of human heparinase has not been directly studied, other known heparinases belong to the class of enzymes known as lyases. Based on similarities to known heparinases, it is likely that human heparinase interacts with heparin through binding to its non-reducing end and degrades heparin.

Figure 3:
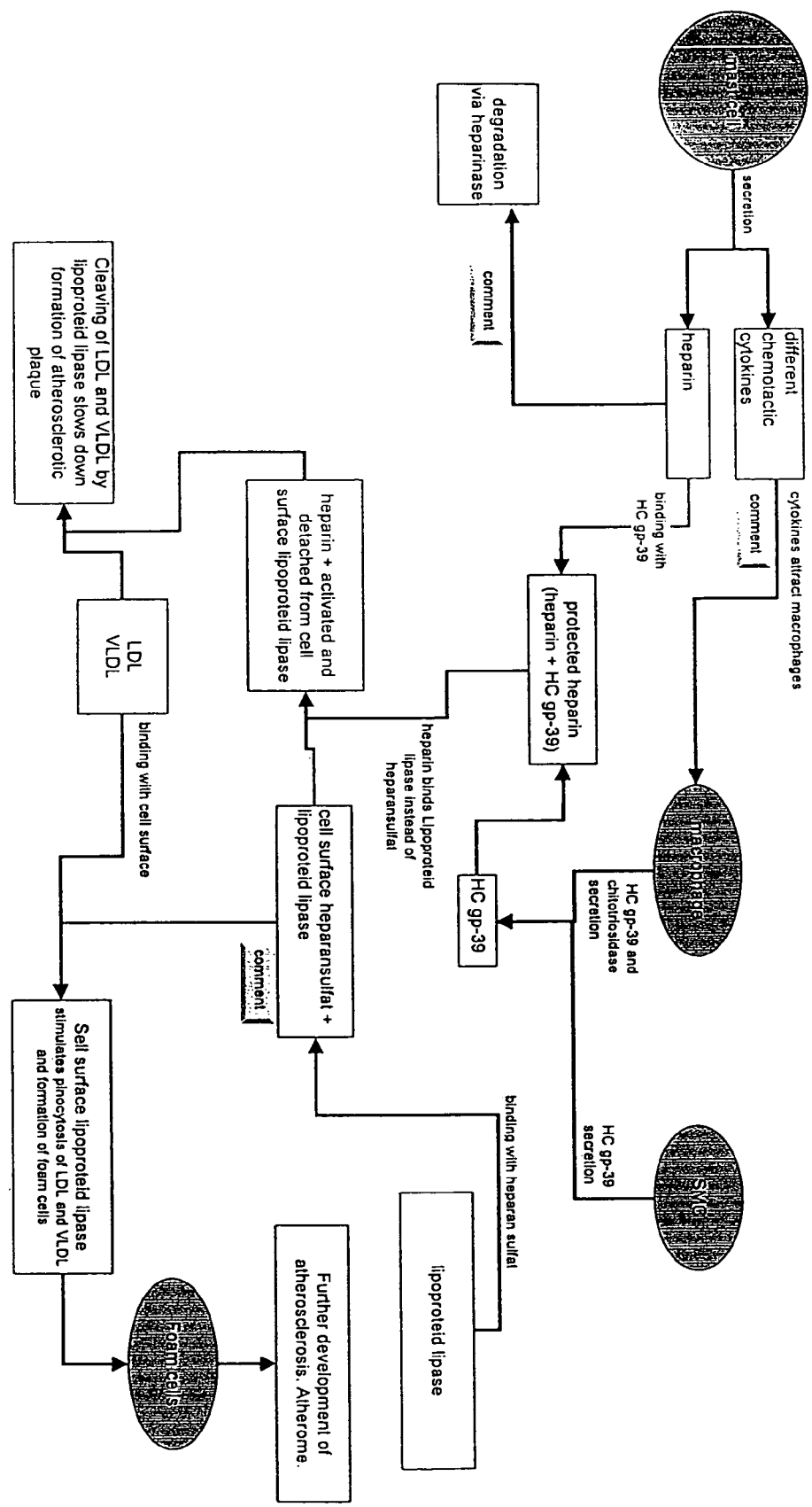
FIG. 3 is a flow diagram illustrating the relationship between pathways involved in atherosclerosis.

HC gp-39, a protein of chitinase family, can also bind to heparin (Medline 96325055). The binding of heparin (or heparin analogs) to HC gp-39 may protect heparin from degradation by heparinase (FIG. 3). By protecting heparin from degradation, the period of time for which heparin is active is extended. The use of HC gp-39 in combination with heparin (or its therapeutic analogs) may enhance the effectiveness of heparin in the treatment of arteriosclerosis.

Currently, there is no direct evidence regarding the way in which HC gp-39 binds to heparin. It is known, however, that some hydrolases, which are close to chitinases, bind their substrates at the non-reducing end of the substrate. HC gp-39, therefore, may similarly bind to the non-reducing end of heparin. This binding would protect heparin from degradation by heparinase. The HC gp-39 homolog from pig smooth muscle culture (porcine gp38k) has been studied in greater detail. HC gp-39 shows 84.6% homology with gp38k (DNAstar). The site of heparin binding on gp38k (residues 144-149, RRDKRH) is similar to a putative heparin binding site on HC gp-39 (RRDKQH) in which glutamine is substituted for arginine in the human protein.

Example 2

Tissue Remodeling

Figure 5:
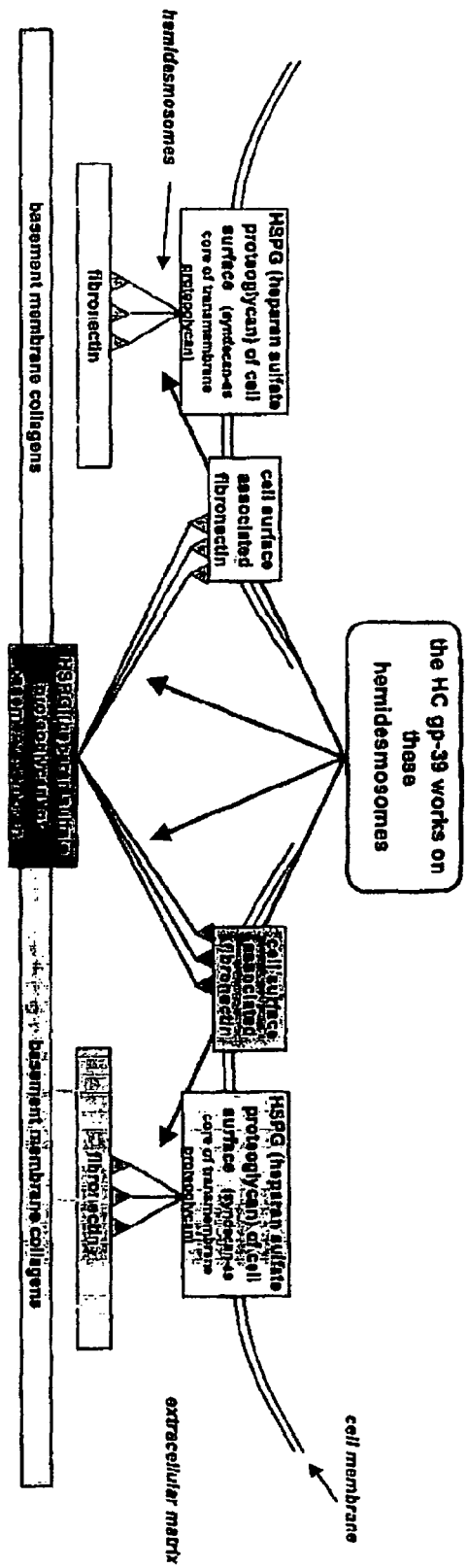
FIG. 5 is a schematic view of various interactions between the cell surface and the extra-cellular matrix.

In most tissues, cells are connected through a membrane-based complex of polysaccharides and through membrane-linked proteins known as the glycocalix and the extra-cellular matrix. Heparan sulphate is one of the most important components of both the glycocalix and the extra-cellular matrix. Heparan sulphate binds to fibronectin and other structural proteins; this binding is required for the fixation of cells within tissues and determines tissue structure (FIG. 5). The mechanisms of binding between heparan sulphate and fibronectin have been studied, and this binding is significant in the positioning of fibroblasts, epidermal cells, and endothelium (PMID 3917945, 8838671, 10899711). It has also been shown that heparan sulphate binds to thrombospondin during the establishment of the intercellular contacts (PMID 1940309), and that there is a correlation between cell aggregation and the binding of heparan sulphate with syndecan-1 (PMID 7890615).

HC gp-39, a protein of the chitinase family, has a higher affinity for heparan sulphate than does fibronectin (Medline 96325055). HC gp-39 may compete with fibronectin for the binding of heparan sulphate. If HC gp-39 binds to heparan sulphate replacing fibronectin, intercellular bonds and the structural components which retain tissue structure can be relaxed. Such relaxing is required for successful tissue remodeling and regeneration. By increasing the local concentration of HC gp-39 and thereby locally relaxing structural elements of a tissue, tissue remodeling and regeneration can be stimulated. Such an application would be useful in such areas as wound healing and joint alterations due to arthritis.

Example 3

Arteriosclerosis

Hyaluronic acid (HA) binds to smooth muscle cells and prevents their proliferation. Proliferation of smooth muscle cells in arteriosclerosis leads to the growth of the arteriosclerotic plaque. Therefore, HA is a factor that helps contain the disease. Chitotriosidase, or chitinase 1, may restrict the synthesis of HA by degrading the chitin primers necessary for HA formation. Therefore, chitotriosidase facilitates the growth of arteriosclerotic plaques. Suppression of the activity of chitotriosidase may be useful in the treatment of atherosclerosis (see FIGS. 4A and 4B).

Hyaluronic acid is involved in various processes of tissue repair and remodeling. In particular, HA plays a role in the regulating the migration and proliferation of smooth muscle cells which are critical in the pathogenesis of cardiovascular diseases. HA acts as a negative regulator of the proliferation of smooth muscle cells induced by platelet-derived growth factor (PDGF) and as a positive regulator of PDGF-induced migration (PMID: 9678773, 8842351, 7568237).

Uncontrolled proliferation of smooth muscle cells facilitates the growth of atherosclerotic plaques. As cells start to actively absorb lipid particles, turning into foam cells, the cells form the core of the plaque. Additionally, proliferation of smooth muscle cells leads to the enlargement of the formation and the isolation of the foam cells by covering them with new layers of smooth muscle cells. This further leads to the formation of atheroma, or the degeneration of the artery lining. Drugs that reduce smooth muscle cell proliferation are often used as a part of atherosclerosis therapy. Most of these drugs, however, are hormones that have many undesirable side effects and may be restricted in their use.

HA is synthesized on the extracellular side of the plasma membrane of various cell types, including smooth muscle cells and endothelial cells (PMID: 10493913). Apparently, fibroblasts provide a source for much of the HA implicated in atherosclerotic damage (see e.g., PMID: 11378333, 11327061, 11171074). HA synthesis is catalyzed by the enzyme hyaluronan synthase (HAS). Presently, three human genes for this enzyme have been identified: HAS-1, HAS 2, HAS 3, mapping to chromosomal regions 19q13.3-q13.4, 8q24.12, and 16q22.1, respectively. HAS is a plasma membrane proteins.

It has been shown that human hyaluronan synthase is highly homologous to the enzymes from other organisms including glycosaminoglycan synthase from *Xenopus* (DG42). (PMID: 8798544, 8798477). It has been shown that DG42 and its analogs from zebrafish and mouse exhibit chitin oligosaccharide synthase activity. Furthermore, addition of purified chitinase to zebrafish cell extracts leads to significant (up to 87%) reduction in the synthesis of HA. Based on these data, it is thought that chitin oligosaccharides serve as primers for hyaluronic acid synthesis (PMID: 8643441).

Chitotriosidase (EC 3.2.1.14) and HC gp-39 expressed by macrophages in the area of atherosclerotic damage have been found in the blood vessel wall matrix. It has been suggested that chitotriosidase recognizes the HA primer as its own substrate and, therefore, interferes with the synthesis of HA (PMID: 10073974).

The mechanism by which chitotriosidase participates in the process of regulating proliferation and migration of smooth muscle cells may be based on its enzymatic activity with respect to chitin-like oligosaccharides that serve as primers for HA synthesis. The cleavage of these primers by chitotriosidase may lower the local concentration of HA, therefore, leading to an increase in cell proliferation causing further damage to the blood vessel wall.

Example 4

Cosmetics

Glycosaminoglycans are widely used in dermatology and cosmetology for healing and regeneration of skin damage due to trauma, surgery, or aging. In the past decade, a number of cosmetics and therapeutic treatments; containing glycosaminoglycans were developed and marketed for topical use and for injection. Compositions have included glycosaminoglycans such as chitosan, hyaluronic acid, heparin, heparan sulphate, and others. The inclusion of human lectin HC gp-39 into topical compositions with; glycosaminoglycans may accelerate and prolong skin improvement (FIG. 5).

Addition of HA to the extra-cellular matrix causes hydration and increases turgor in a tissue. As discussed above, HA is also one of the; important factors in tissue remodeling, as it interacts with a number of proteins and non-protein components of extra-cellular matrix to form a scaffold for the formation of cell layers. HA stimulates the expression of metal proteases in the extra-cellular matrix, for example, elastase-like endopeptidases expressed in fibroblasts and keratinocytes. Both of these cell types receptors for binding hyaluronic acid which is needed for tissue remodeling.

Figure 4A:
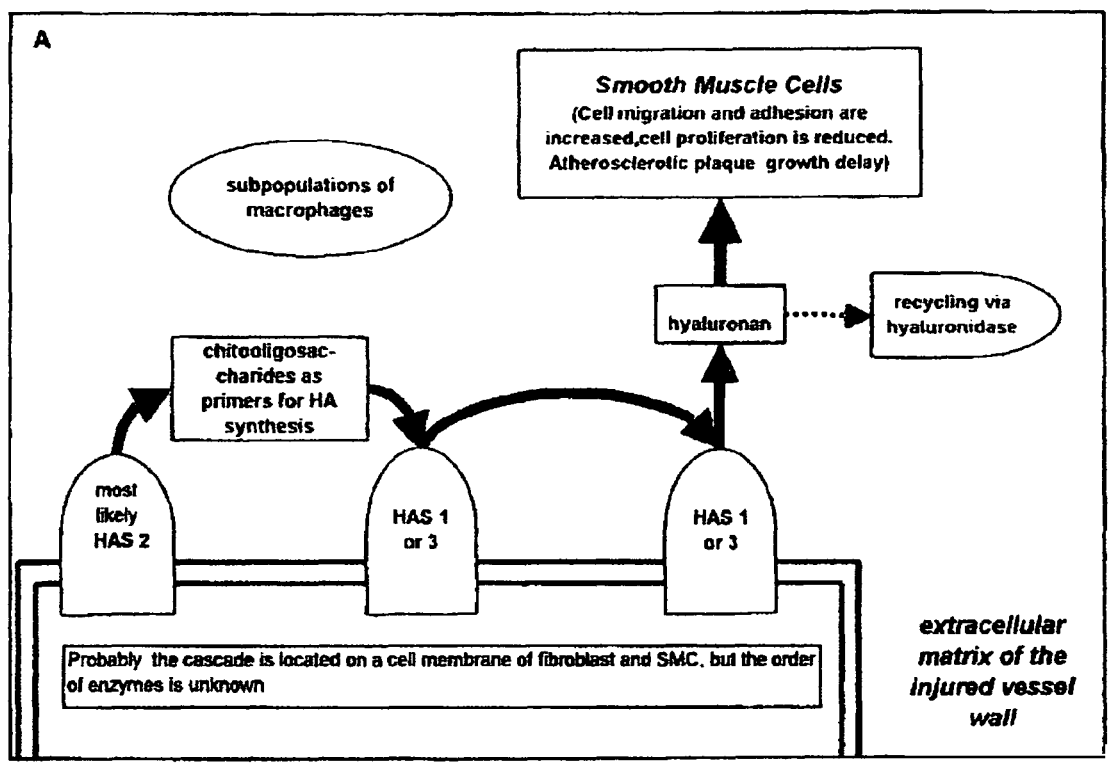
FIG. 4A is a flow diagram illustrating the pathway of chitotriosidase function in atherogenesis when chitotriosidase activity is suppressed.
Figure 4B:
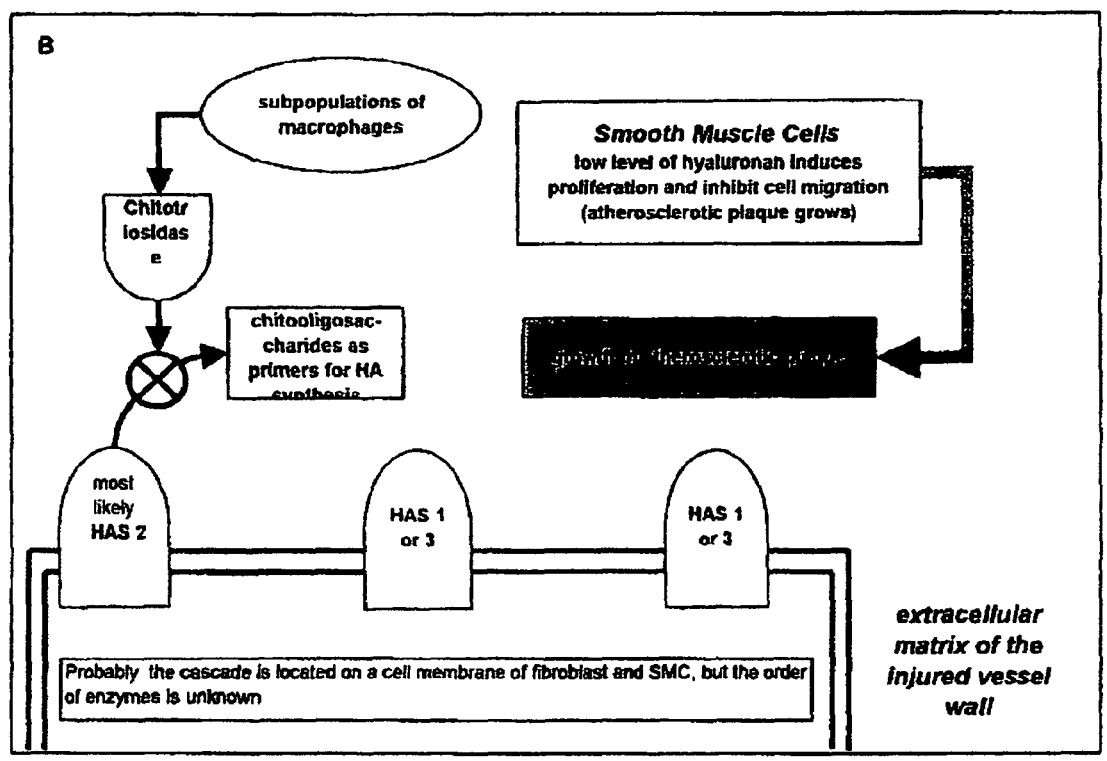
FIG. 4B is a flow diagram illustrating the pathway of chitotriosidase function in atherogenesis when chitotriosidase activity is present.

The use of HC gp-35 in combination with hyaluronic acid, may play a function similar to lectin, having a loosening effect on both protein and; glycosaminoglycan elements of the extra-cellular matrix. Treatment with HC gp-39 and HA would preferably be followed by treatment with fibroblast growth factor (FGF) and insulin-like growth factor (IGF) in order to stimulate expression of HAS1, HAS2 and HAS3 for endogenous synthesis of HA (FIGS. 4A and 4B).

Therapeutic or preventive treatment with HA is especially important for elderly patients or patients with age-related conditions because the level of endogenous HA diminishes with age. (With age, the number of lipid-filled macrophages raises causing an increase in the concentration of chitotriosidase and, correspondingly, the depletion of endogenous HA.) HA is also capable of deep penetration into the epidermis and may be used as a vehicle for drug delivery.

Example 5

Parkinson's Disease

One of the treatments for Parkinson disease includes transplantation of neurons from the substantia nigra of 6-10 week old embryos. The effectiveness of this treatment depends on the successful incorporation of the transplanted tissue. Currently employed techniques show fairly low success rate. The low success rate is; related to rejection of the transplant, usually within several months after surgery. It has been shown that successful transplantation can be achieved with the addition of embryonic neuroectodermal cells of *Drosophila melanogaster* into the transplant tissue. (PMID: 9532720; PMID: 9449456). These cells are known to express a number of growth factors and remodeling factors, including DS47, which is homologous to human protein HO gp-39.

Incorporation of a transplant is related to the processes of tissue remodeling. Integration of transplanted cells into a damaged tissue and; differentiation of the transplanted cells is necessary for restoring the function of the damaged tissue. These processes are related to tissue remodeling, and remodeling factors play a significant role in the interaction of transplanted cells with the extra-cellular matrix and the cells of the recipient. Often rejection of the transplant is not due to an immune response in the recipient, but rather to the lack of tissue integration caused by the formation of filial scar tissue and the lack of blood vessel in-growth into the transplanted tissue. One apparent reason is the low activity of remodeling factors in the recipient tissue. In particular, the rejection it may be related to age-dependent weakening of remodeling capabilities.

It may be possible to regulate tissue remodeling upon transplantation by changing the local concentration of remodeling factors, including proteins belonging to chitinase family such as HC gp-39. Activity of brain chitinases should be related to microglial cells that are descendants of blood monocytes. Neutral cells of a transplant, on the other hand do not accumulate enough remodeling factors due to their nature. The significant increase in transplant integration success rates by incorporating *Drosophila* embryonic cells suggests that these cells actively express remodeling factors that are closely related to such factors in humans. It is known that four proteins belonging to the chitinase family are expressed in the human brain (HC gp-39, chitotriosidase, YKL 39, and FLJ12549). There is also expression of chitinase-like proteins in the embryonic cells of *Drosophila*. These proteins lack catalytic activity, but are capable of binding with proteoglycans of the extra-cellular matrix. One of the *Drosophila* proteins shows slightly homologous to human HC gp-39 (PMID 7875581).

Example 6

System Reconstruction of *Emericella nidulans*

This example presents the first study of metabolic reconstruction of a eukaryotic organism based solely on Expressed Sequence Tag (EST) data. As illustrated in the present example, the process of the present invention can be used to study metabolism, not just in humans, but in any species. This study was performed within the framework of the WIT 2 system, a WEB-based environment for comparative analysis of genomes, publicly available at the University of Oklahoma's Advanced Center for Genome Technology. The WIT Project was instituted to develop a framework for the comparative analysis of genomic sequence data, focusing largely on the development of metabolic models for sequenced organisms.

*Emericella nidulans* (formerly *Aspergillus nidulans*) was chosen as a model organism for this work. *Emericella nidulans* has been a classical genetic organism for more than fifty years. Its unique metabolism has been extensively studied, especially with regard to carbon compounds. Carbon and alcohol metabolism, nitrogen assimilation, acetamide and proline utilization, amino acid metabolism, sulfur metabolism, and penicillin and sterigmatocystin biosynthesis are the best characterized metabolic systems in *E. nidulans*.

Gene expression and regulation have also been studied extensively in *E. nidulans*. There are some fairly well understood systems, such as nitrogen metabolite repression, carbon catabolite repression, regulation of acetamide utilization, regulation of purine degradation, regulation of metabolic flux in the quinate and shikimate pathways, and regulation of gene expression by pH, oxygen and phosphorus. Recently, significant progress has been made towards understanding genetic regulation of reproduction and development in *E. nidulans*. See, Adams et al., Coordinate control of secondary metabolite production and asexual sporulation in *Aspergillus nidulans*. Moreover, *Emericella* belongs to a family of industrially important fungi, some of whose members are common human opportunistic pathogens, and all of which are able to produce penicillin and carcinogenic toxins (aflatoxin, sterigmatocystin, etc.). The genome size of *E. nidulans* is about 30 Mb. This organism has a typical ascomycetes life cycle, which includes a vegetative stage and three reproductive cycles: sexual, asexual, and parasexual.

EST data for *Emericella nidulans* and *Neurospora crassa* were provided by Oklahoma University. Unigene databases for both organisms were created by multiple sequence alignments of different ESTs which were believed to correspond to the same actual gene, providing a more accurate and longer version of the gene sequence. 4155 unigene ESTs were provided for *Emericella nidulans* (abbreviated EN in Table 1) and 633 unigene ESTs were provided for *Neurospora crassa* (abbreviated NC in Table 1).

Using these unigene entries, similarities to known protein sequences were computed using blastx and by comparison to other EST sequences using blastn. The results are summarized in Table 1. The numbers in Table 1 represent the percentage of sequences from *E. nidulans* and *N. crassa* that show similarity to sequences from each of the other organisms listed. For example, 29.2% of *E. nidulans* sequences and 34.9% of *N. crassa* sequences show similarity to the yeast sequence.

TABLE 1

| Organism | Hits | | Hits with Function | |
|---|---|---|---|---|
| | EN | NC | EN | NC |
| Yeast | 0.292 | 0.349 | 0.205 | 0.273 |
| C. elegans | 0.162 | 0.238 | 0.157 | 0.222 |
| N. grasse | 0.067 | N/A | 0.063 | N/A |
| E. nidulans | N/A | 0.202 | N/A | 0.192 |
| Any eukaryote | 0.457 | 0.597 | 0.408 | 0.557 |
| Any bacteria | 0.157 | 0.306 | 0.171 | 0.276 |
| Any archaea | 0.059 | 0.145 | 0.054 | 0.140 |
| Anything | 0.484 | 0.631 | 0.432 | 0.586 |

About 40-60% of the sequences fail to show similarity to any protein in the non-redundant protein database with a cutoff of 1.0e, which is quite strict. When the cutoff was set at 1.0e-2, an additional 5% of the ESTs showed recognizable similarity. The fraction of hits against proteins with known function in *Emericella nidulans* is slightly lower than the percentages that are seen with complete chromosomal sequences for the ORFs, which is about 55-60% at this time). EST data, and even unigene EST data, is made up of relatively short sections of genes that include frameshifts. Without the frameshifts, blastx (or FastA) would produce excellent results. The recognizable similarities would certainly go up in the cases involving frameshifts if they could be corrected or if approximate translations estimating the position of the frameshift could be produced. It may be possible to achieve this type of result if ESTs from a closely related organism were available.

The goal of the instant example is to produce an accurate System Reconstruction for *Emericella nidulans* based on the available EST data. System Reconstruction generally involves two steps. First, assignment of a function to each unigene number is made. Second, a set of metabolic pathways specific for the organism is identified. Since each asserted pathway is composed of a set of functional roles (i.e., enzymes), the unigene entries, with their appropriate functions and corresponding EC numbers, were associated with each of the asserted pathways. The comparative value of the reconstruction from EST data versus reconstruction based on genomic data is summarized in Table 2 below.

TABLE 2

| Organism | S. cerevisiae Genomic Data | E. nidulans EST Data |
|---|---|---|
| Genome Size | 12.01 Mb | About 30 Mb |
| Available ORFs | 6,261 ORFs | 4,472 unigene ESTs |

TABLE 2-continued

| Organism | S. cerevisiae Genomic Data | E. nidulans EST Data |
| --- | --- | --- |
| % of the Genome Functions Assigned | 100% 3,119 ORFs | 15% 2,826 ORFs |
| Pathways Identified | 462 | 602 |

Assignments were made to about 2,800 of the ESTs, and then development of an emerging model of the metabolism of E. nidulans began. An extensive literature search for E. nidulans has been performed. The search focused on known metabolic pathways of this organism, as well as on gene regulation and physiology of filamentous fungi. Almost every pathway asserted for E. nidulans has a corresponding reference included in the annotation. The current reconstruction is composed of more than 600 asserted pathways which connect to about 500 specific ESTs. Many pathways are composed of a single reaction, and many others are known to exist biochemically but specific ESTs corresponding to the appropriate functional roles could not be identified. Thus, the collection of assigned functions and asserted pathways represents a model of the metabolism of E. nidulans. This model can be integrated with the growing body of both genetic sequence data and available biochemical characterizations. Such integration forms the basis for a continuing analysis of the organism. The current status of system reconstruction for both S. cerevisiae and E. nidulans is summarized in Table 3 below. Some of the asserted pathways have broken down into categories. The numbers in Table 3 indicate where the analysis is relatively complete and where it is sparse or lacking altogether. Some of these pathways are single reactions that may have similar forms in different cell states.

TABLE 3

| | Number of Pathways Asserted | |
| --- | --- | --- |
| Metabolic Category | Yeast | E. nidulans |
| Amino Acid | 139 | 162 |
| Aromatic Hydrocarbons | 1 | 8 |
| Carbohydrate Metabolism | 97 | 147 |
| Coenzymes and Vitamins | 23 | 23 |
| Electron Transport | 10 | 10 |
| Lipid | 34 | 36 |
| Membrane Transport | 14 | 22 |
| Oxygen and Radicals | 6 | 8 |
| Nitrogen | 0 | 1 |
| Nucleic Acid | 17 | 17 |
| One-carbon | 3 | 3 |
| Phosphate | 7 | 7 |
| Protein | 23 | 25 |
| Purine | 46 | 51 |
| Pyrimidine | 35 | 36 |
| Sulfur | 4 | 4 |
| Signal Transduction | 1 | 1 |

As the System Reconstruction of E. nidulans for a given number of unigene entries was completed, a visual outline for major parts of metabolism was created. Such schemes not only provide descriptive overviews of certain parts of metabolism, but also reflect the expression patterns specific for a given EST library. The expression patterns become evident when the representation of enzymes in pathways is compared with different sources of expression data, independent from EST data. The expression pattern of identified genes in the reconstruction strongly correlates with data present in the literature, further validating the method of System Reconstruction. For example, one of the most important secondary metabolic pathways, the sterigmatocystin biosynthetic pathway, composed of at least 29 enzymatic activities, is developmentally regulated. A positive correlation between both asexual and sexual sporulation and synthesis of the mycotoxin has been documented. In the present study, a cDNA library was constructed from E. nidulans, strain FGSC A26 (veA 1, bio), which had undergone development for 24 hours on a solid surface with an air interface and, therefore, contained cDNAs from both vegetative mycelial cells and cells involved in asexual reproduction. Indeed, unigene numbers for all 29 genes in the pathway have been identified, and most of them had several candidates for the same gene. Another example is the penicillin biosynthetic pathway which consists of only 3 enzymes: DELTA-(L-ALPHA-AMINOADIPYL)-L-CYSTEINYL-D-VALINE SYNTHETASE (acvA), ISOPENICILLIN N SYNTHETASE (ipnA), and ACYL-COENZYME A:6-AMINOPENICILLANIC ACID ACYLTRANSFERASE (aatA). Expression of both acvA and aatA is slightly repressed by glucose in fermentation medium. Consistent with literature data, there are no unigene candidates for acvA, one for aatA, and two for ipnA.

The reconstruction of E. nidulans metabolism illustrates the use of System Reconstruction from EST data. In fact, alterations to WIT required to support an analysis based upon both EST and chromosomal sequence data have been made. The outcome represents an initial effort to encode the known metabolism of E. nidulans and to relate the analysis to actual sequence data (in this case largely ESTs). Such an effort lays the foundation for an ongoing analysis of the genome and embeds the analysis in a framework that supports comparative analysis between organisms.

Example 7

System Reconstruction of Amino Acid Metabolism

Figure 23A:
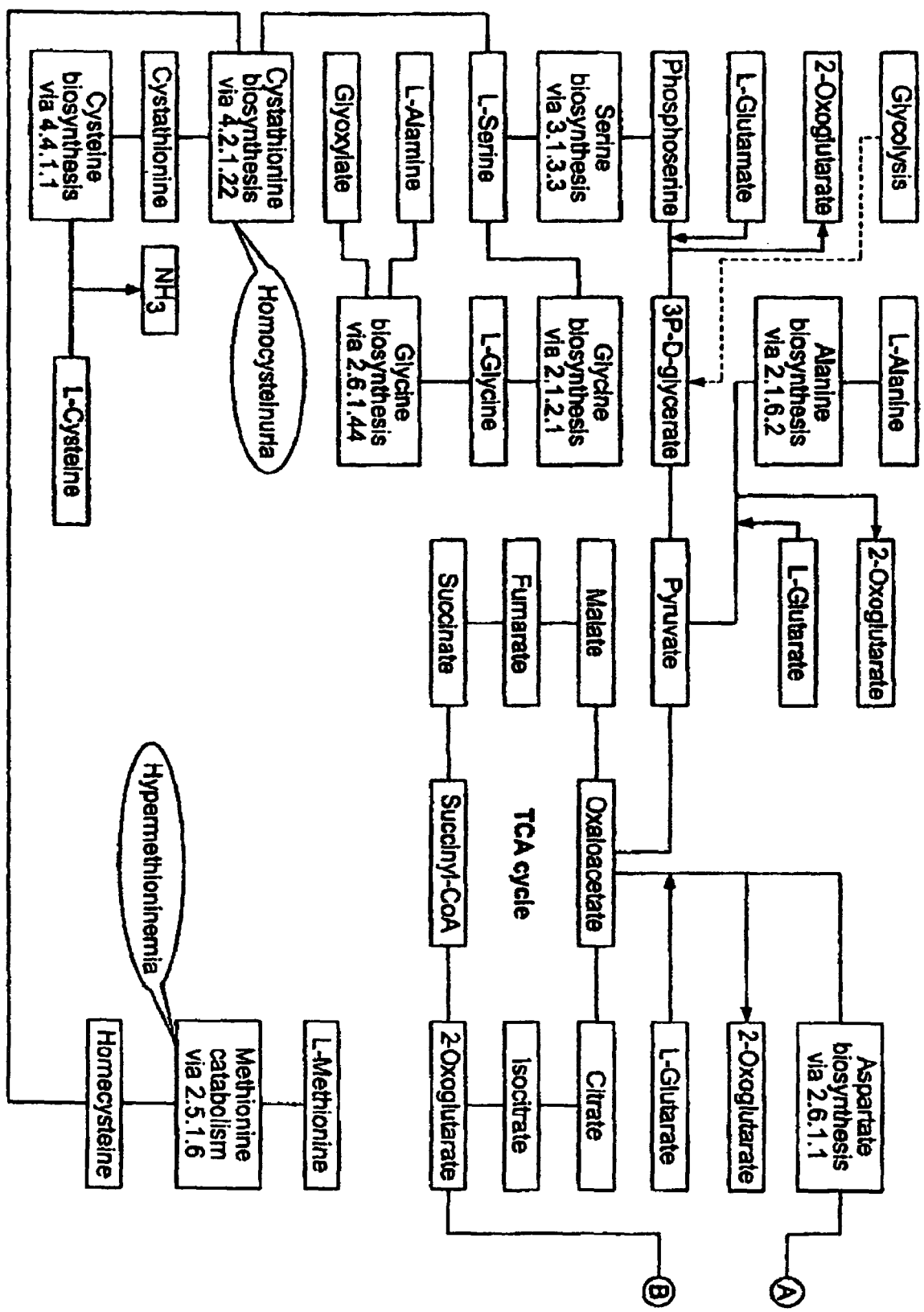
FIG. 23A is an illustration of a TCA cycle map.
Figure 23B:
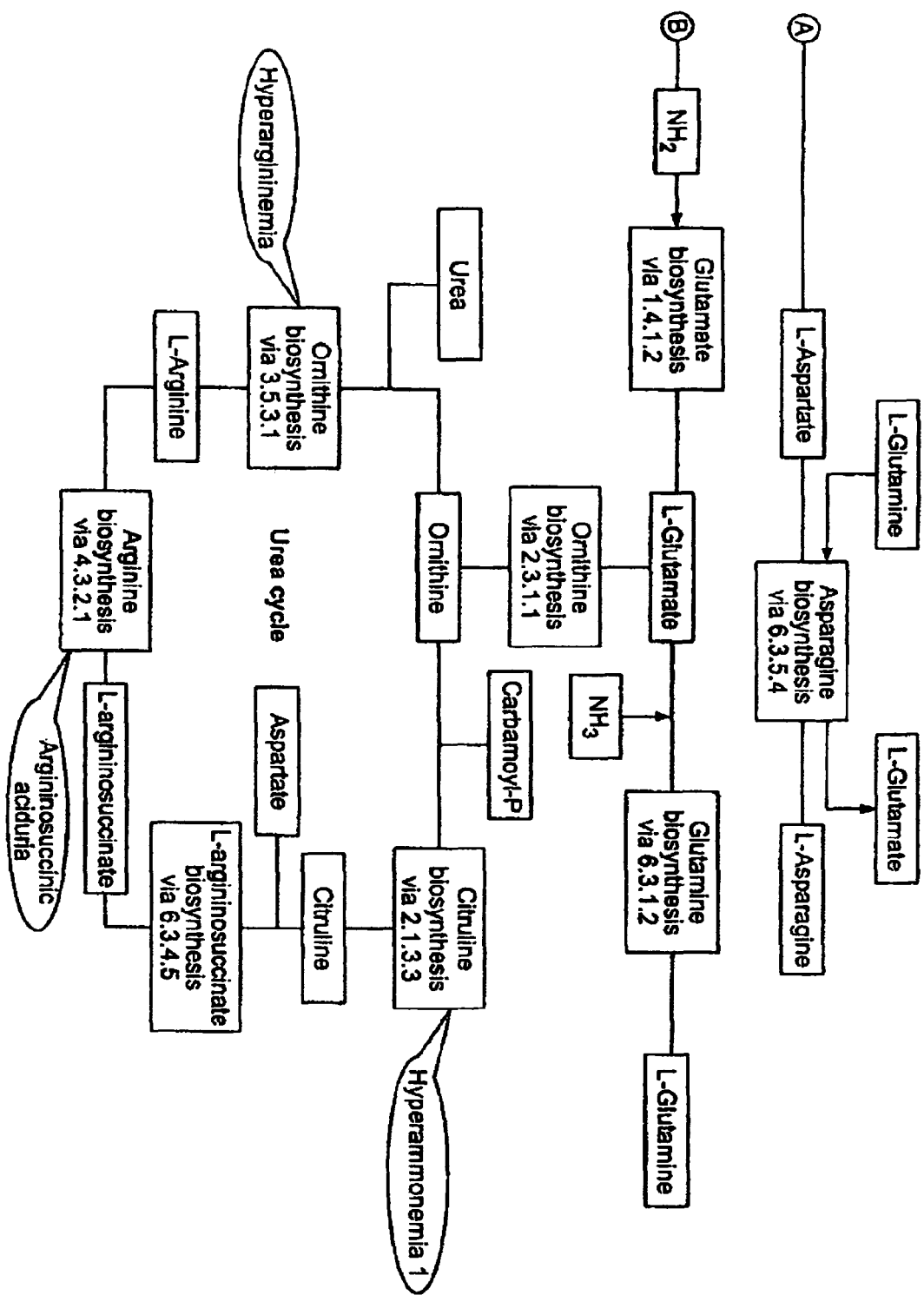
FIG. 23B is an illustration showing an enlarged view of a portion of the TCA cycle map in FIG. 23A.
Figure 23C:
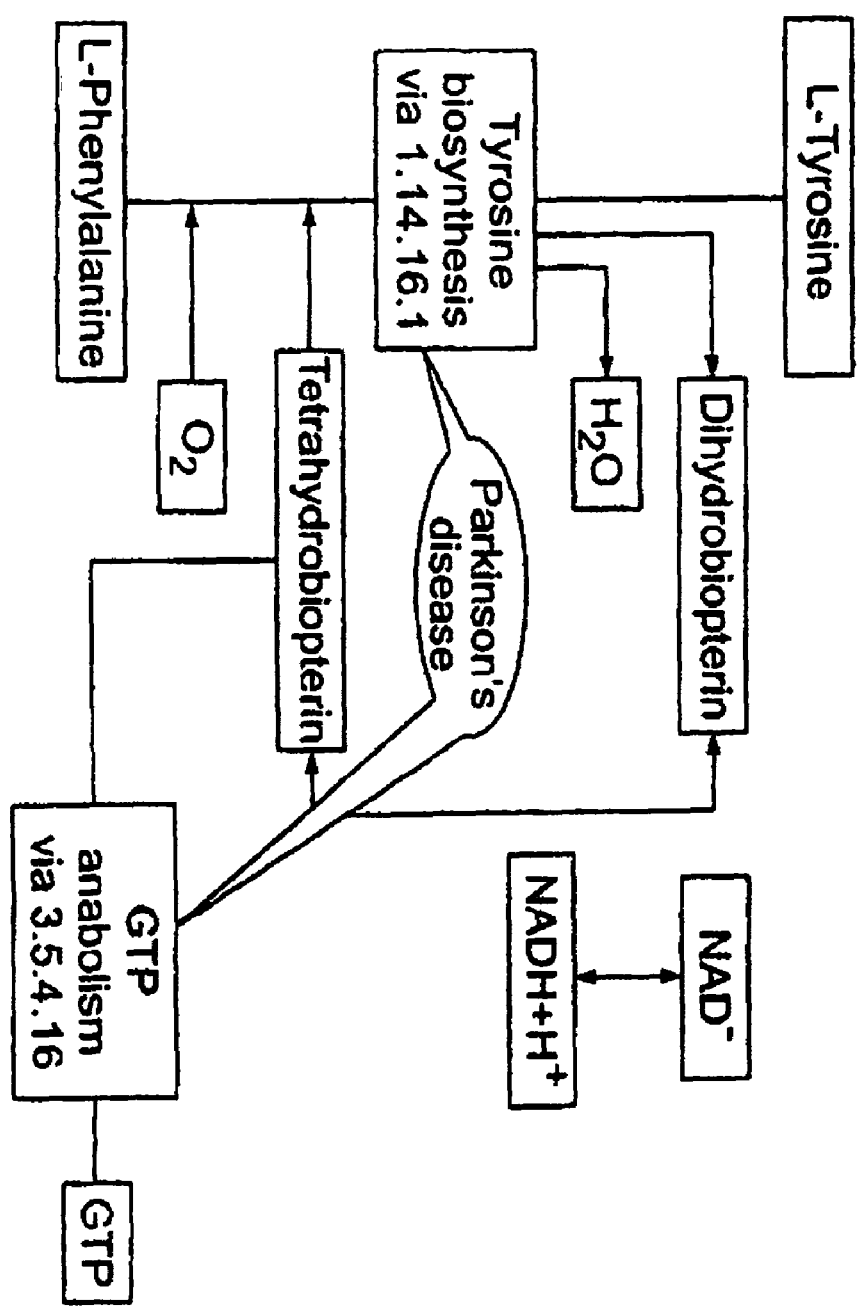
FIG. 23C is an illustration showing an enlarged view of a portion of the TCA cycle map in FIG. 23A.

The System Reconstruction method was used to analyze amino acid metabolism in humans. A portion of the reconstructed map showing the TCA cycle is shown in FIGS. 23A-C. System Reconstruction utilizes various types of information for different data fields. Examples of the types of data gathered, analyzed, and integrated are discussed below.

For each of the enzymes, the following data is collected: systematic name and synonyms; EC number (if assigned); a spectrum of substrates and products, including not only specific compounds, but also classes of compounds; known inhibitors and activators; kinetic data, including constants such as KM and Vmax for the enzyme or semi-quantitative data on reaction time-scales; and bibliographic references.

The database of amino acid metabolism includes about 150 reactions and pathways described in biomedical literature as involved in biosynthesis and degradation of amino acids. These are reactions and pathways that have been identified experimentally. The following types of information are collected for each reaction or pathway: participating compounds and their roles; a spectrum of enzymes catalyzing the reactions in the pathway, indicating enzymes whose involvement has been identified experimentally in vivo and, those that could participate in the pathways based on their ability to catalyze pathway's reactions; localization and compartmentalization of components; kinetic data, whenever available; and bibliographic references.

For intermediate compounds that occur in the collected pathways and reactions, the following types of data are collected: systematic name of the compound and synonyms; compound classification and compound major structural and functional groups; the endogenous status of the compound in human metabolism (whether the compound occurs as a natural intermediate in human metabolism); thermodynamic data such as free energy, enthalpy and entropy of formation; and bibliographic references. Thermodynamic data are used in combination with metabolic profiles to evaluate the plausibility of the proposed novel pathways.

The first step in building functional models is to link the collected pathways into metabolic networks. There are different types of molecules as well as different types of interactions between biological molecules, and these are indicated through different types of links. Such links are implicitly contained in the database. Indeed, whenever two pathway records share a common intermediate, or an intermediate in one pathway occurs as a regulatory factor in a record for the enzyme from another pathway, it implies a link between these two pathways. Further computations would be facilitated, however, if such links translate into explicit relations among pathways. To this end, a set of special database queries have been developed that extract such relationships and generate tables to describe such links explicitly. These tables constitute a computer representation of a biochemical network that forms a skeleton of the System Reconstruction Model. Unlike the assembled or statistically inferred networks used in many studies, the System Reconstruction Model is built from experimentally verified pathways that may be thought of as identified routes on a biochemical network. It is important to note that only a small fraction of all possible reaction sequences are realizable as functional pathways in any given organism. The types of relationships included in the network may include, for example, the following: pathways linked by shared substrates and/or products; activation of an enzyme by the intermediate metabolite; inhibition of an enzyme by the intermediate metabolite; metabolites that lead to the induction of expression of an enzyme-related gene; metabolites that lead to the suppression of the expression of a gene; and regulation of a transporter or channel by an intermediary metabolite. As the data are collected, other import links may become evident and can be included in the model.

The next step involves converting the network of pathways into a System Model. A network of pathways is only a skeleton on which other data can be assembled. Data integration is accomplished by a specially developed procedure called Structured Annotation. In the course of this procedure, links are established between particular elements in a pathway network. Elements include, for example, pathways, enzymes, metabolites, and the like. This procedure is practically achieved by filling in the annotation tables associated with each element. There are three major categories of data that are integrated into the model at this stage: function-related information; molecular data; and clinical manifestations of human diseases.

Function-related information for pathways and reactions includes functional roles in the human body. These roles may be represented as the catabolism or biosynthesis of certain important molecules, cell energetics, activation, inhibition of various cellular processes, and the like. Functional assignments are not exhaustive, as they have likely resulted from the sets of experiments focused on the specific function. Taken together and integrated within the network of pathways, however, they represent a useful picture of biological functionality and its underlying mechanisms. The types of information used include organ and tissue localization of the pathway element; intracellular localization and/or compartmentalization; the existence and subcellular localization of the element in other organisms; and references to the primary information source.

Molecular data may include, for example, sequence data, such as genes, ORFs, and Unigene clusters that are associated with enzymes; conditional expression information for an enzyme; genetic polymorphisms of an enzyme and the impact of such polymorphisms on its properties; references to the primary information source; cross-references to records in public genomic databases such as Genebank and TrEMBl; and the like.

Clinical manifestations may include, for example, connection of the element with a disorder (cause, manifestation, and the like), references to the primary information source, and the like. One feature of the model is the incorporation of clinical manifestations (traits) and the ability to view and analyze these data types within the framework of other data integrated into the model. Some clinical traits are directly linked to alteration of a certain biological functions while others are associated with particular genes, proteins, or compounds. The latter are often statistical correlations (e.g., a mutation in a gene correlates with predisposition to a certain disease). In the System Reconstruction Model, biological functions, molecular data, and clinical traits are all linked to a network of pathways. Such a representation allows for the elucidation of the biochemical mechanisms that underlie specific clinical observations.

The user interface of the reconstruction is an interactive map (FIGS. 23A-C) showing pathways involved in amino acid metabolism. Pathways are interconnected into a network by shared metabolites. By clicking the mouse on a pathway or a component of a pathway, a user can access the pathway page showing detailed diagrams with all reactions and enzymes. In this example, the specific pathway for serine biosynthesis is illustrated. Similar information is available for other areas of metabolism, and the System Reconstruction technology can be applied to any area of metabolism. By clicking on the link for "serine biosynthesis via 3.1.3.3" as shown on the TCA cycle diagram in FIG. 23A, the link to the serine biosynthesis scheme (FIG. 24) is accessed. While serine biosynthesis is used as an example here, the database contains similar integrated information for each pathway or component that has a dot in the corner, as seen in FIGS. 23A-C.

Figure 24:
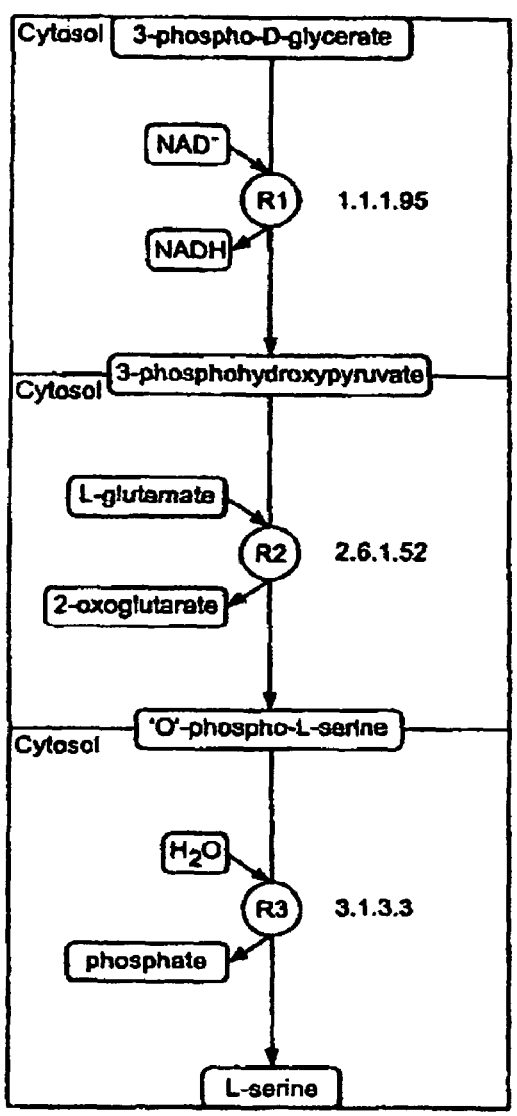
FIG. 24 illustrates a serine biosynthesis scheme (3-phospho-D-glycerate/L-glutamate//2-oxoglutarate/L-serine/cyt).

The serine biosynthesis scheme, illustrated in FIG. 24, shows each reaction of the pathway, each enzyme, and the cellular localization of each reaction. Notes regarding the pathway are accessible from the serine biosynthesis scheme page (FIG. 24) by clicking on "notes." The notes associated with the serine biosynthesis scheme are shown in FIGS. 25A-B. The notes page (FIGS. 25A-B) contains (1) a list of the reactions involved; (2) the enzymes, including the EC number, the name of the associated gene, expression information, and links to ESTs; (3) annotations including diseases associated with the pathway, information about the diseases, and links to references about the diseases; and (4) a list of tissues and cell types in which the pathway is known to occur.

Details for each reaction in the pathway also are accessible from the scheme page. In the serine biosynthesis scheme (FIG. 24), additional information is accessible by clicking on a reaction center (indicated as R1, R2, or R3 in FIG. 24) or by clicking on an enzyme (indicated as 1.1.1.95, 2.6.1.52, or 3.1.3.3 in FIG. 24). For example, by clicking on R1 in FIG. 24, one can access the reaction page for the first reaction in the pathway (3 phospho-D-glycerate+NAD+=3-phosphohydroxypyruvate+NADH), shown in FIG. 26. The reaction page shows the overall reaction, details of the reaction, the cellular localization of the reaction, the catalyst, and any available annotations.

From the scheme page (FIG. 24), from the notes page (FIGS. 25A-B), or from the reaction page (FIG. 26), various enzyme pages can be accessed. By clicking on 1.1.1.95 from any of these pages, the enzyme page (FIGS. 27A-B) for EC 1.1.1.95, phosphoglycerate dehydrogenase, is accessed. The enzyme page (FIGS. 27A-B) contains a list of alternative names for the enzyme, genes associated with the enzyme, pathways and reactions in which the enzyme is involved, and annotations regarding the enzyme. Annotations can include, for example, information on diseases associated with the enzyme, tissues and cells in which the disease has been implicated, and links to references. Additional reaction pages are shown for reaction 2 of the serine biosynthesis scheme (FIG. 28) and reaction 3 of the serine biosynthesis scheme (FIG. 30). Additional enzyme pages are shown for the enzymes, which catalyze reactions 2 and 3 in FIGS. 29 and 31, respectively.

Links to nucleic acid sequences and related literature are also available from the enzyme pages. For example, from the enzyme page for EC 3.1.3.3, phosphoserine phosphatase, shown in FIG. 31, one can access a gene page (FIG. 33) by clicking on the gene name. In this case, by clicking on PSPH, the user is linked to the gene page for phosphoserine phosphatase, EC 3.1.3.3, as shown in FIG. 32. The gene page contains information including the symbol used for the gene, its chromosomal localization, alternate names, expression data, the amino acid sequence encoded by the gene, and links to ESTs.

Figure 34A:
FIG. 34A is the UniGene Cluster Hs.56407 page for EC 3.1.3.3, phosphoserine phosphatase.
Figure 35A:
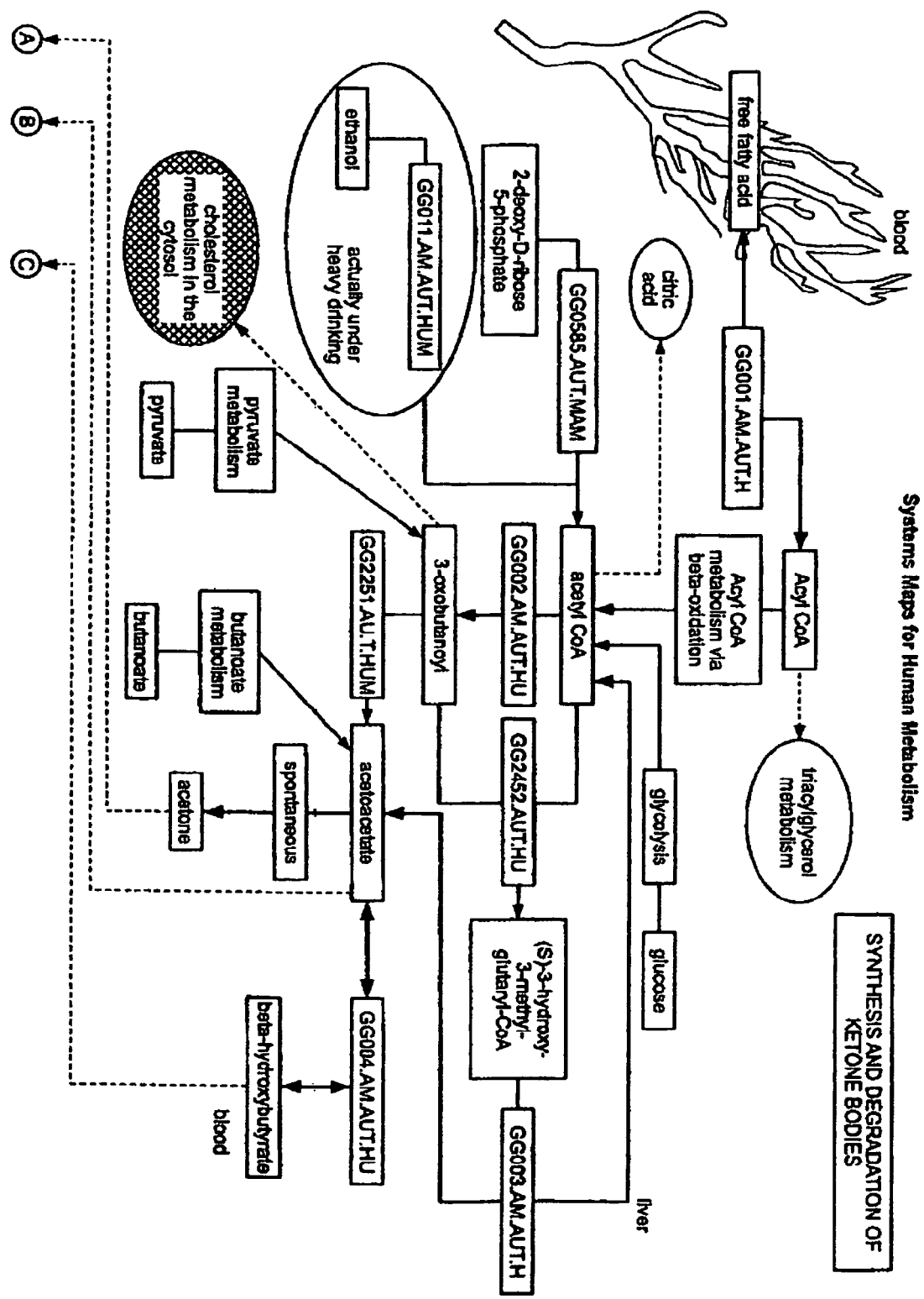
FIG. 35A is a schematic diagram of Systems Maps for Human Metabolism.
Figure 35B:
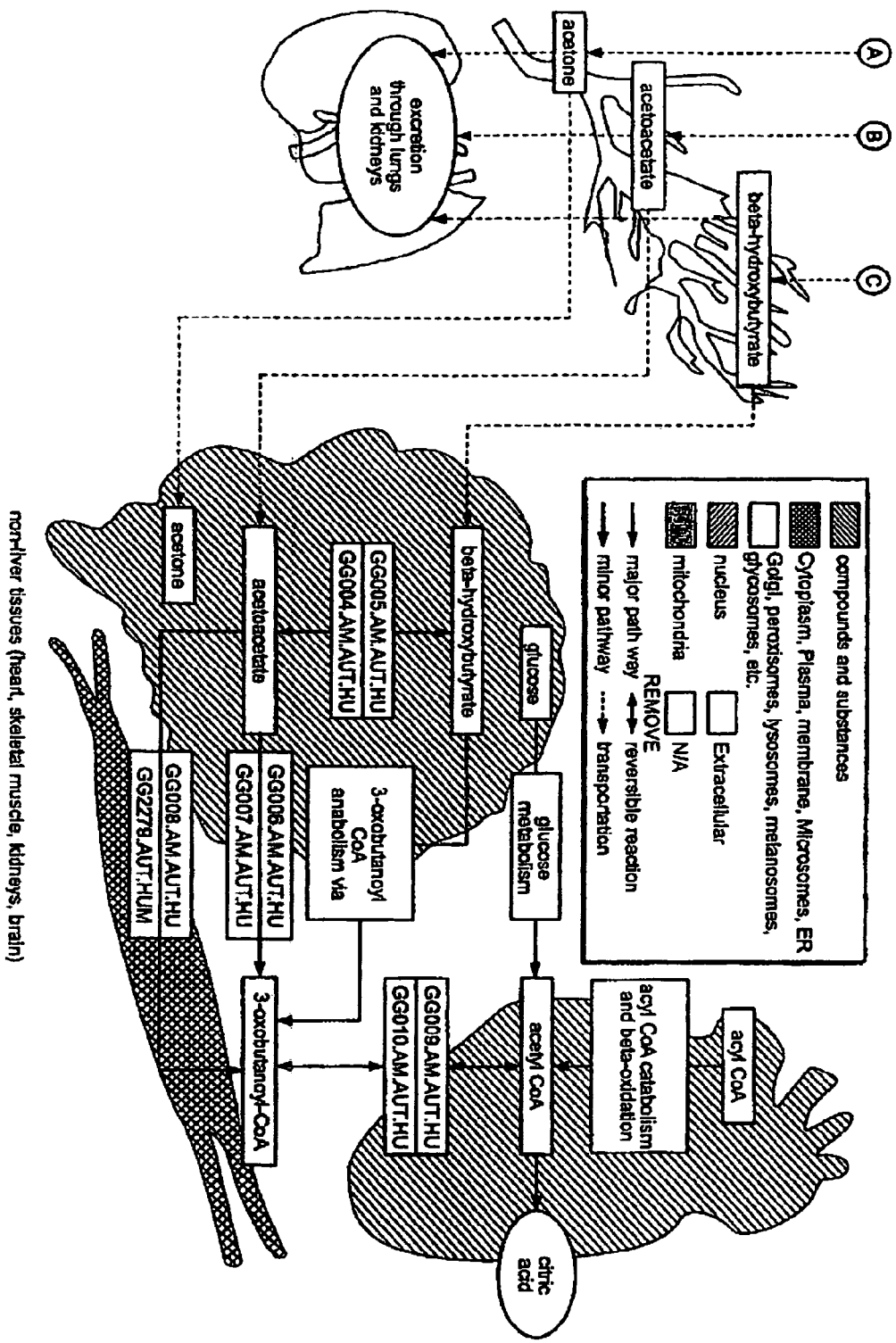
FIG. 35B is a schematic diagram of Systems Maps for Human Metabolism continued from FIG. 35A.
Figure 36A:
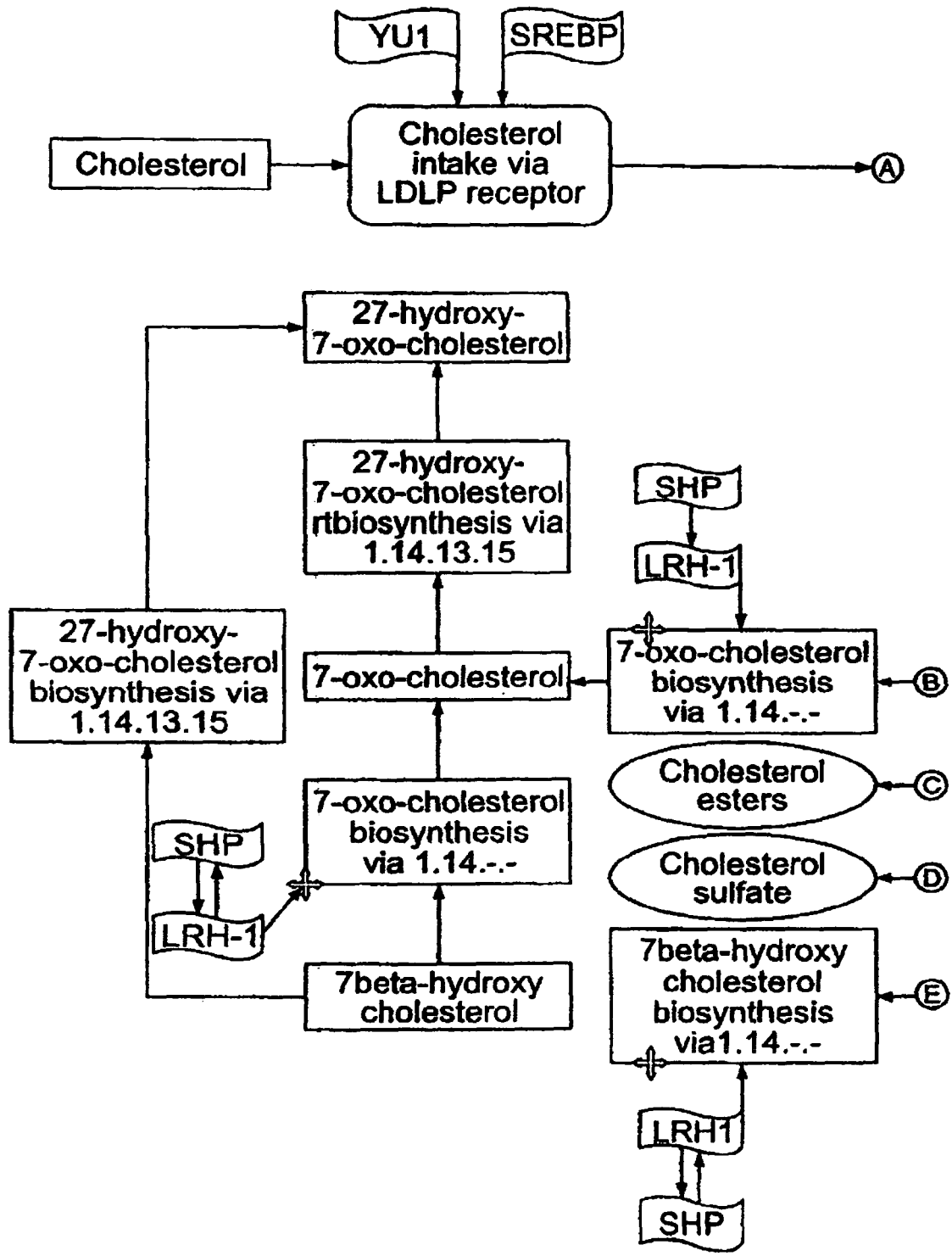
FIG. 36A is a schematic diagram of Systems Maps for Regulation.
Figure 36B:
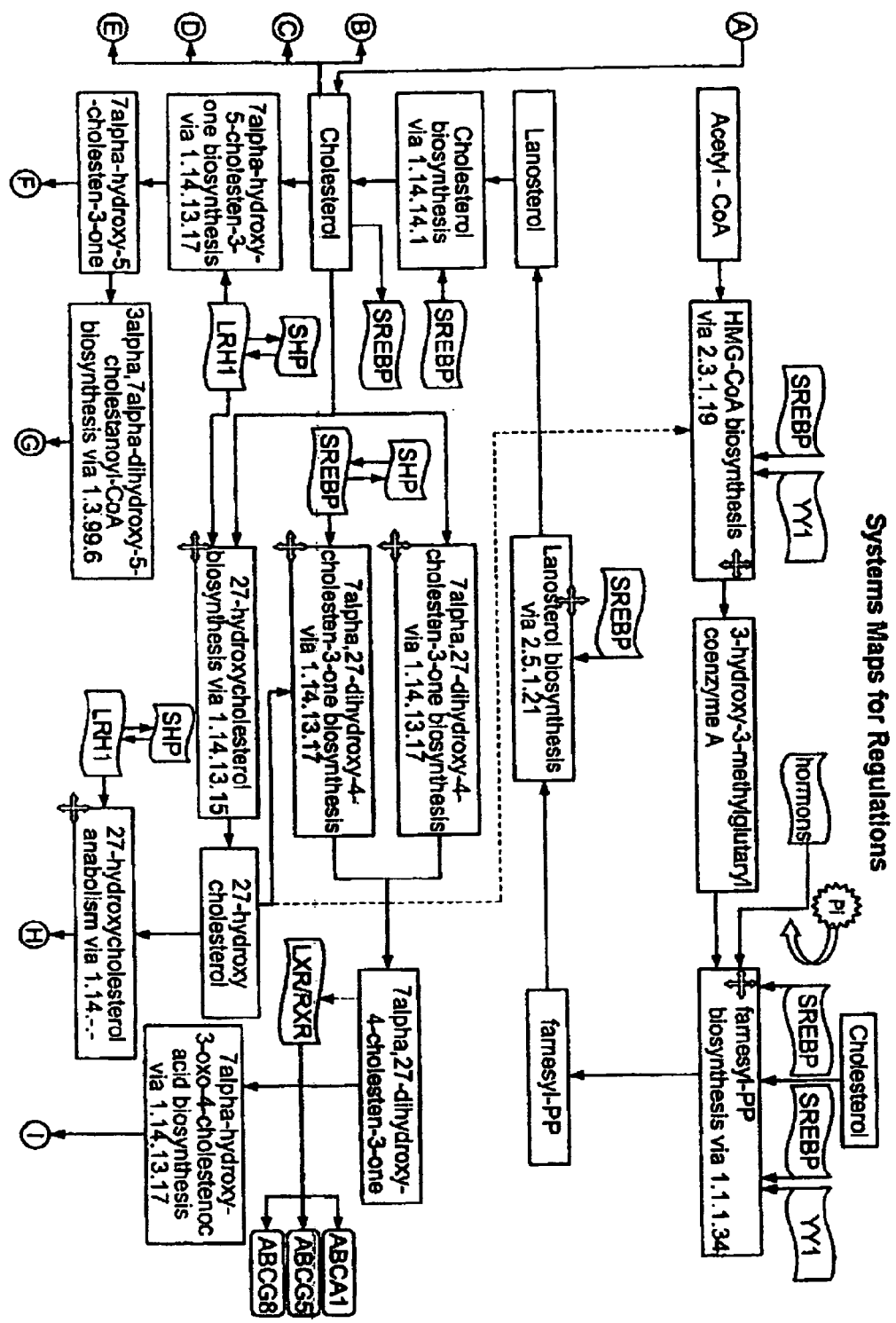
FIG. 36B is a schematic diagram of Systems Maps for Regulation continued from FIG. 36A.
Figure 36C:
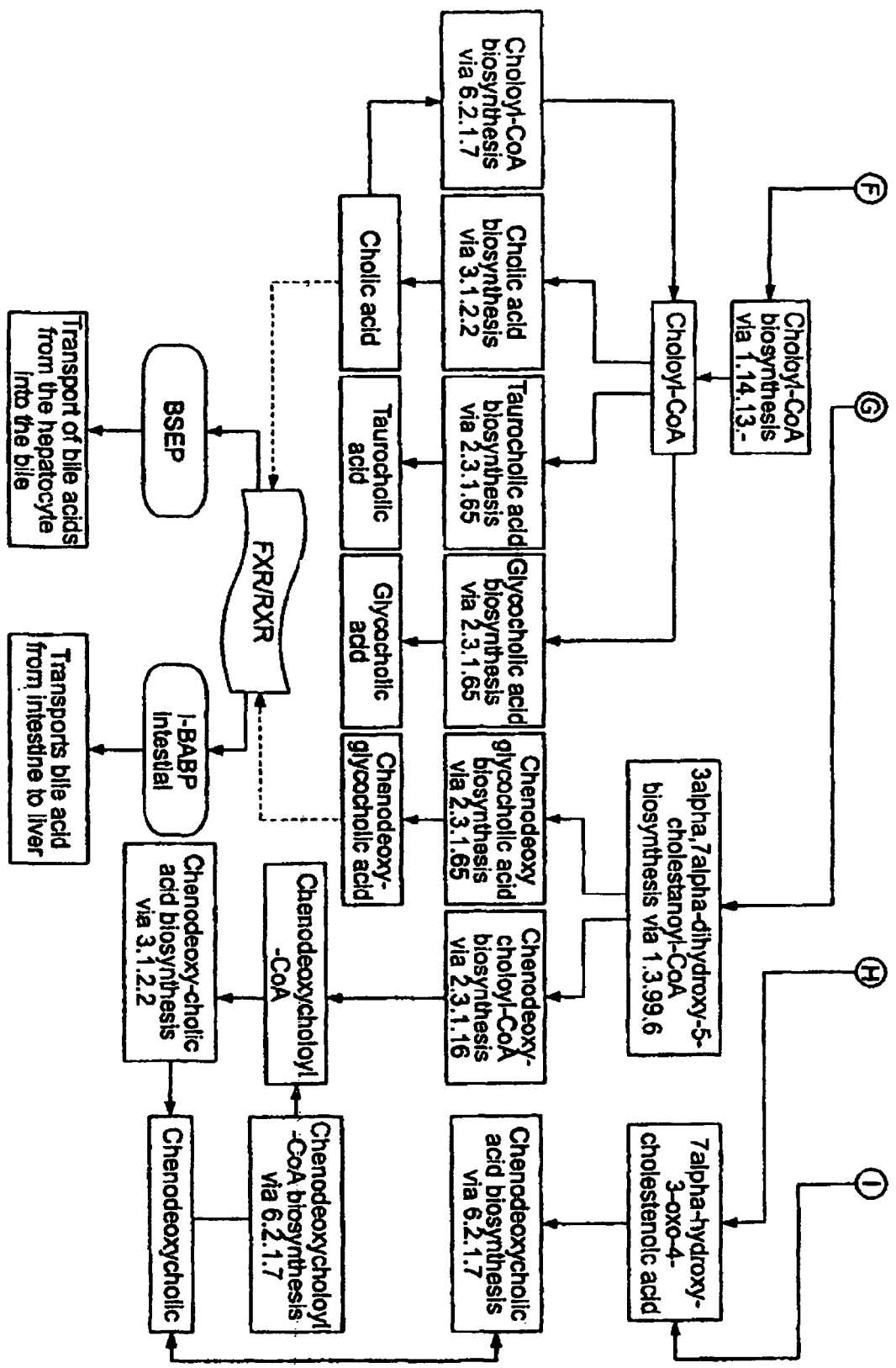
FIG. 36C is a schematic diagram of Systems Maps for Regulation continued from FIGS. 36A and 36B.
Figure 37:
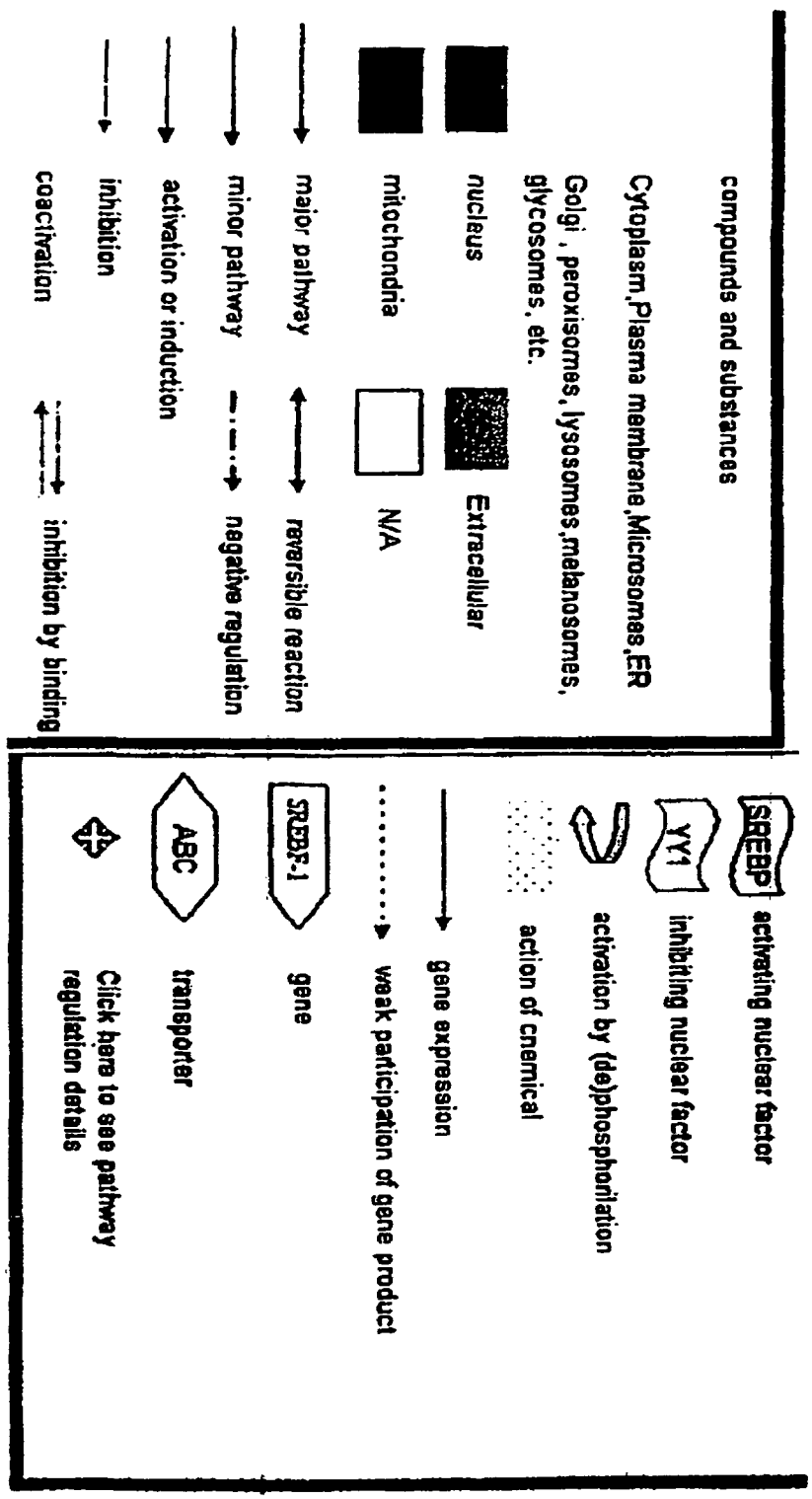
FIG. 37 illustrates a legend of Regulatory Elements.
Figure 38:
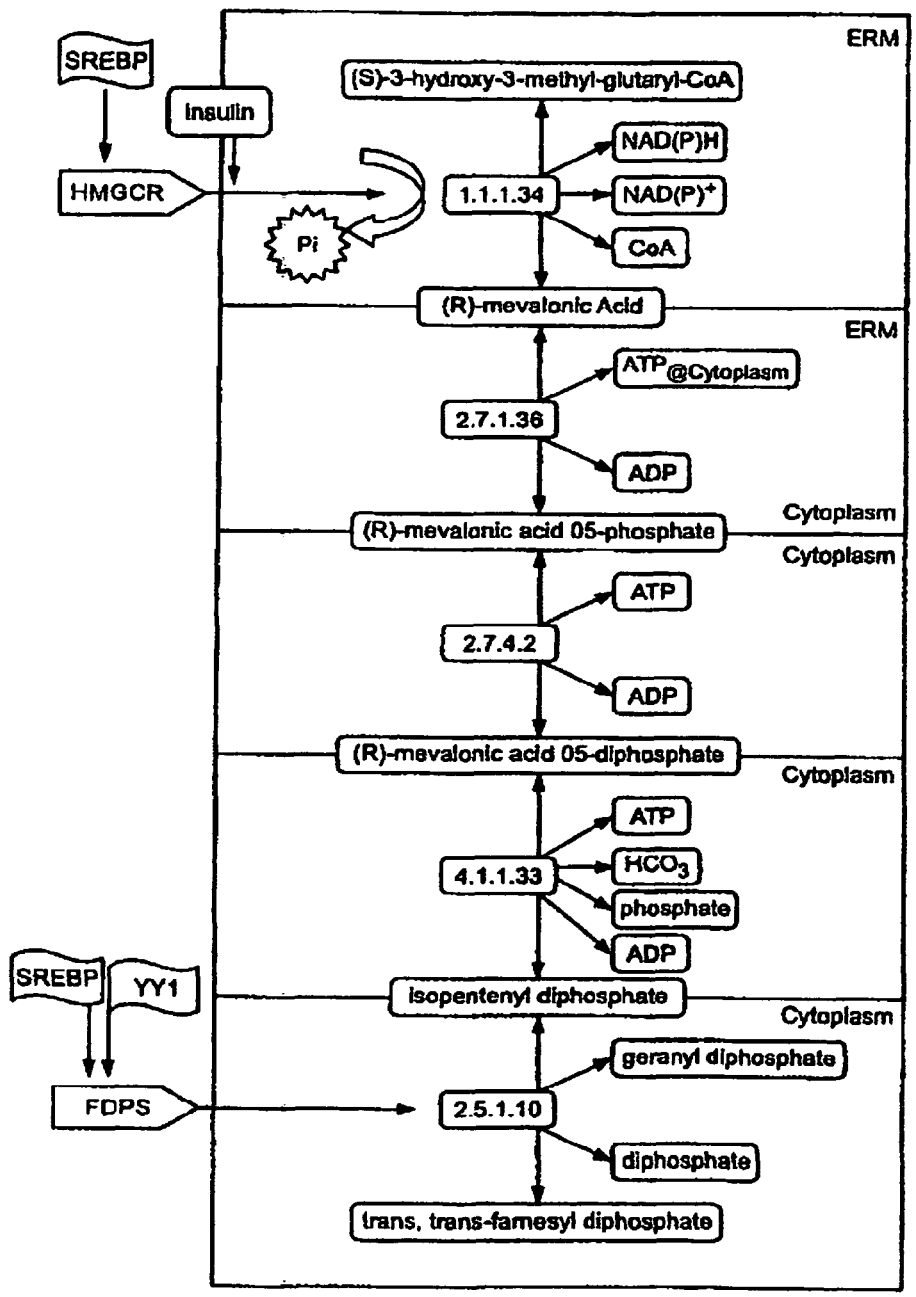
FIG. 38 is a schematic diagram of Links between Metabolism and Regulation.

Examples of sequences linked to the enzyme page (FIG. 31) or to the gene page (FIG. 32) are shown in FIGS. 33A-B and 34A-C. FIGS. 33A-B is the SWISS-PROT page for EC 3.1.3.3, phosphoserine phosphatase, and FIGS. 34A-C is UniGene page for EC 3.1.3.3, phosphoserine phosphatase.

Example 8

Parkinson's Disease

Figure 18:
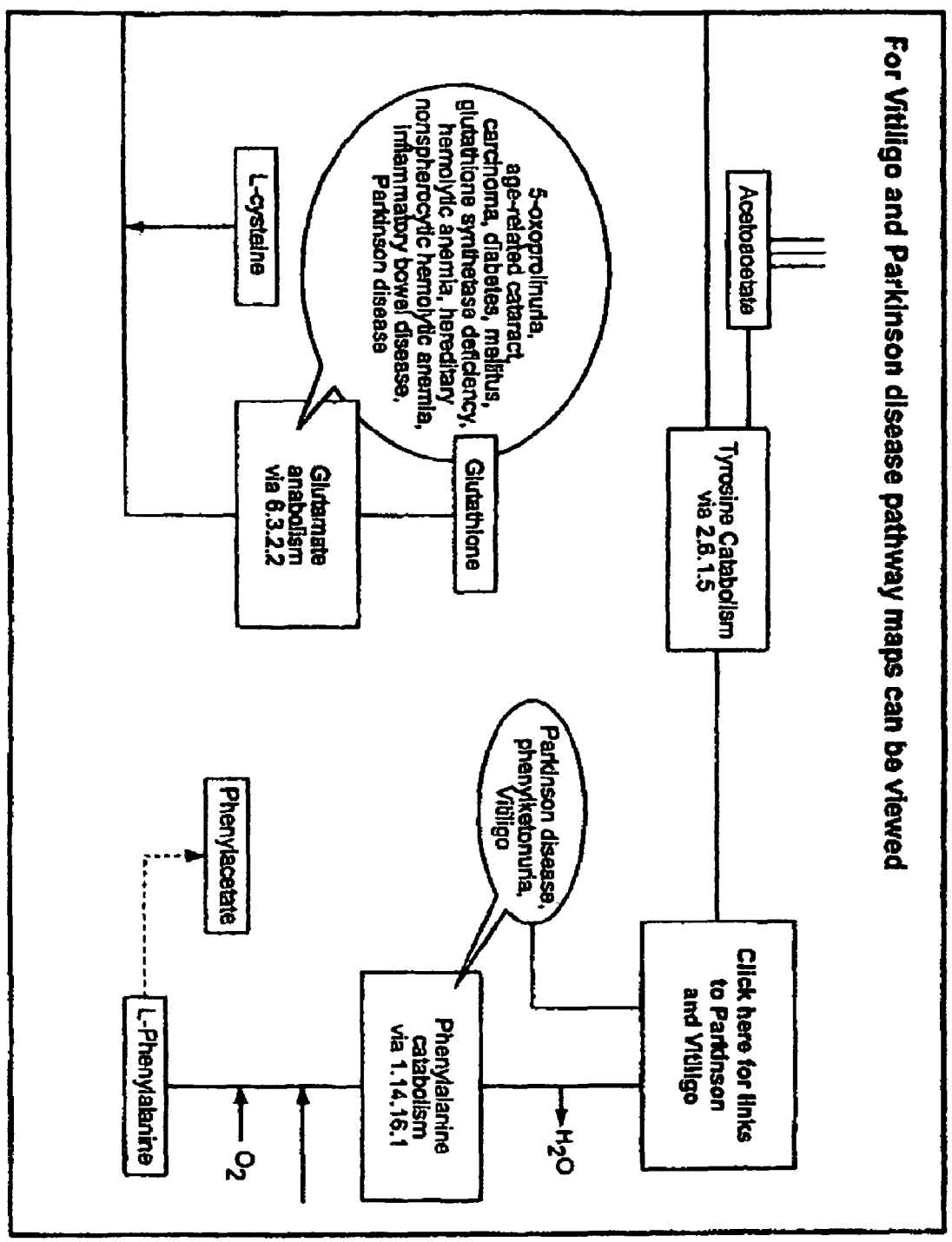
FIG. 18 is an example of a diagram showing diseases associated with pathways, specifically showing links for Vitiligo and Parkinson disease pathway maps.
Figure 19:
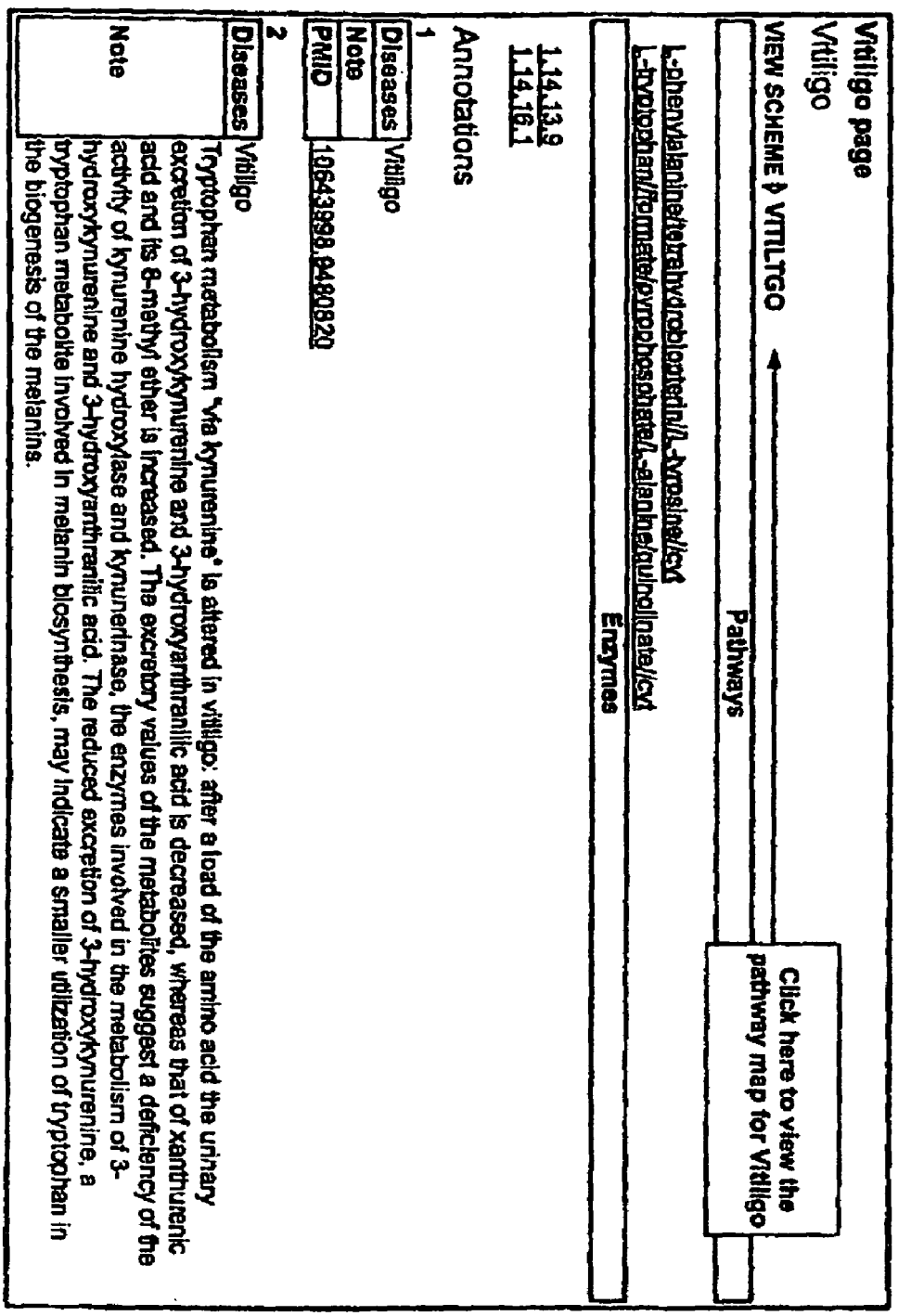
FIG. 19 shows a Vitiligo page.

The System Reconstruction method used to analyze amino acid metabolism in humans, as discussed in Example 7, allowed the elucidation of a number of previously unidentified metabolic links. One such example is related to Parkinson's disease. As illustrated in FIG. 18, diseases associated with various enzymes can be indicated on the interactive metabolic map. By clicking in a link for the disease, or a link for diseases known to be associated with a particular enzyme, the user can access additional information about the mechanism of the disease.

Figure 21:
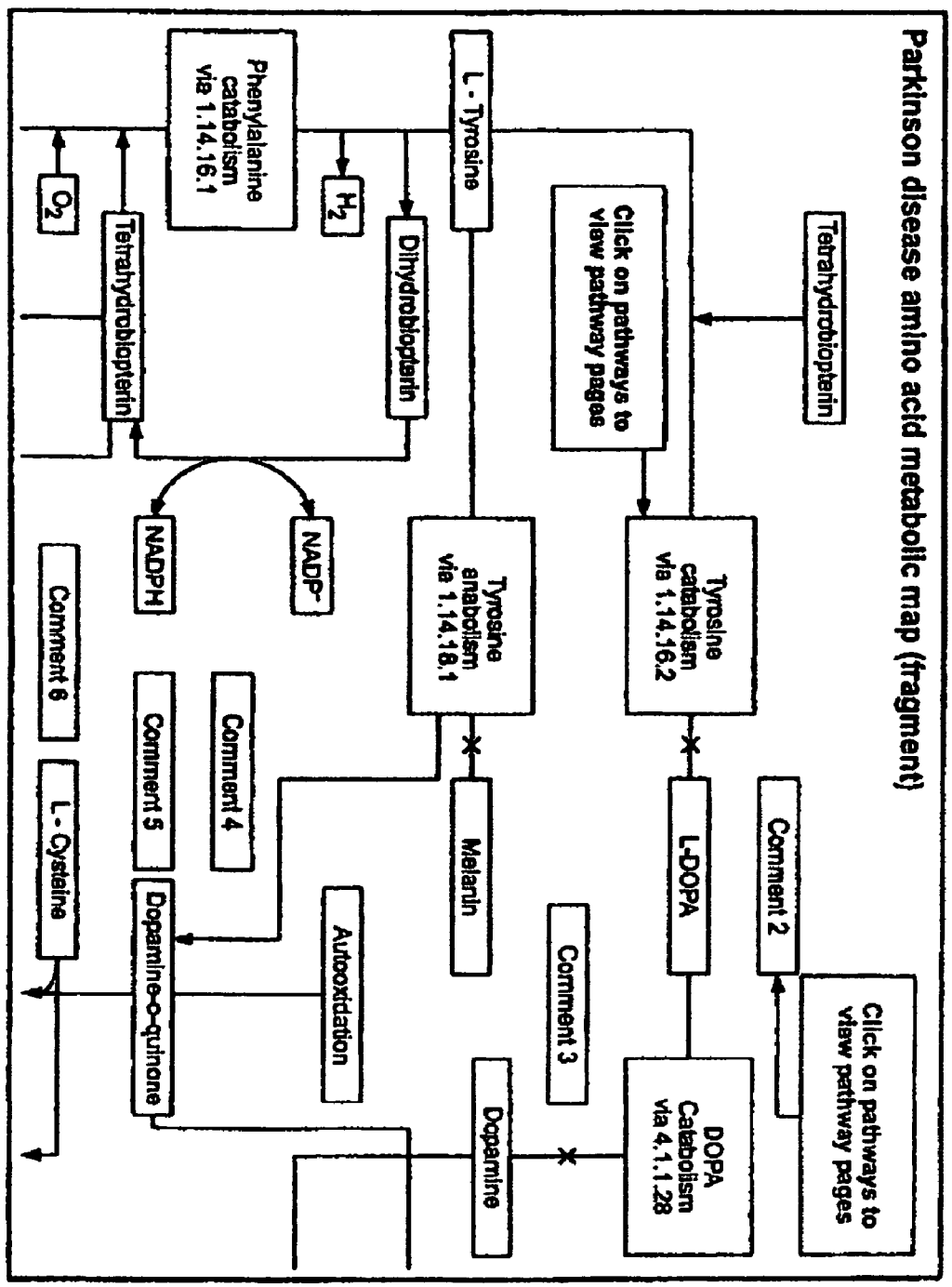
FIG. 21 is an illustration of a Parkinson disease amino acid metabolic map (fragment).
Figure 22:
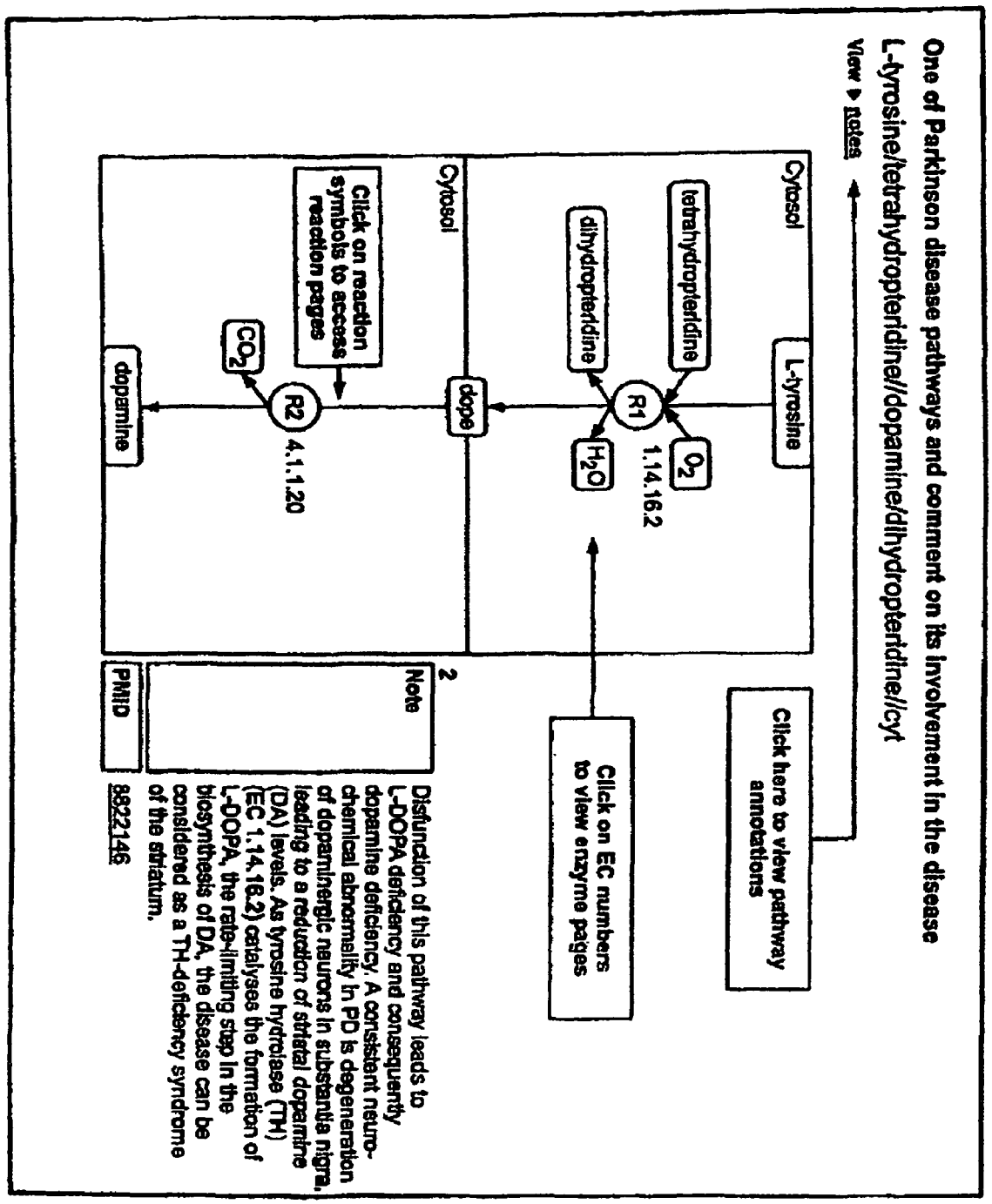
FIG. 22 is an illustration of one of the Parkinson disease pathways and comments.

By clicking on the link for Parkinson's disease from the phenylalanine catabolism portion of the interactive metabolic map (FIG. 18), additional information about Parkinson's disease is accessed. The user is linked to FIG. 20, the Parkinson's disease page. The disease page contains the name of the disease and related diseases or syndromes, and notes regarding the disease, including links to articles relating to the disease. A map of the metabolism specifically associated with the disease is also accessible. FIG. 21 shows a portion of the metabolic pathways that are specifically associated with Parkinson's disease and how those pathways are altered in the disease state. From the disease metabolic map (FIG. 21), the user can access pathway pages and pages with additional comments on the mechanism of the disease. One such disease pathway page is illustrated in FIG. 22.

The metabolic map for Parkinson's disease shows the mechanism by which L-DOPA metabolism is linked to a respiratory pathway (via 1.6.5.3). Deficiencies in L-DOPA metabolism have long been known as one of the causes of Parkinson's disease. The involvement of the respiratory pathway is, however, a recent discovery. This illustrates one example of how of linkages are determined through the method of System Reconstruction.

As illustrated by the foregoing examples, System Reconstruction provides a highly interactive visual overview of metabolism as well as easy access to an abundant amount of information related to the metabolic pathways in question.

Example 9

Network Analysis

The method consists of network analysis of multiple experimental datasets relevant to the diseases. We applied the commercial systems biology platform MetaCore (GeneGo, Inc., St. Joseph, Mich.) as a source of protein-protein interactions and as the means for building and visualization of the networks. The workflow proceeds as following:

A small experiment dataset of genes relevant for the disease is compiled from the literature data. The genes in the dataset have been shown associated with the disease pathology in genetic and biochemical experiments. The exact mechanisms for genes involvement in the disease may or may not be known. Small experiments datasets can include SNP and mutation data, gene amplification data due to chromosomal rearrangements; genes identified by family analysis and other genetic analysis methods. We consider such list as a seed dataset for building the initial networks The second, high-throughput dataset is defined as a list of genes or proteins with changed expression or abundance in the disease condition. These genes and proteins are typically identified in high-throughput experiments such as global gene expression profiling with DNA microarrays, proteomics or metabolomics methods. Such list can also include the genome-wide SNP maps.

The third, analytical dataset is defined as the table of protein-protein, protein-DNA and protein-compound interactions characteristic for human. The interactions are extracted from the experimental literature in scientific journals. Currently, MetaCore contains 45,000 of such interactions, including metabolic reactions and signaling interactions. Only experimentally proven interactions are included in the dataset.

Figure 47:
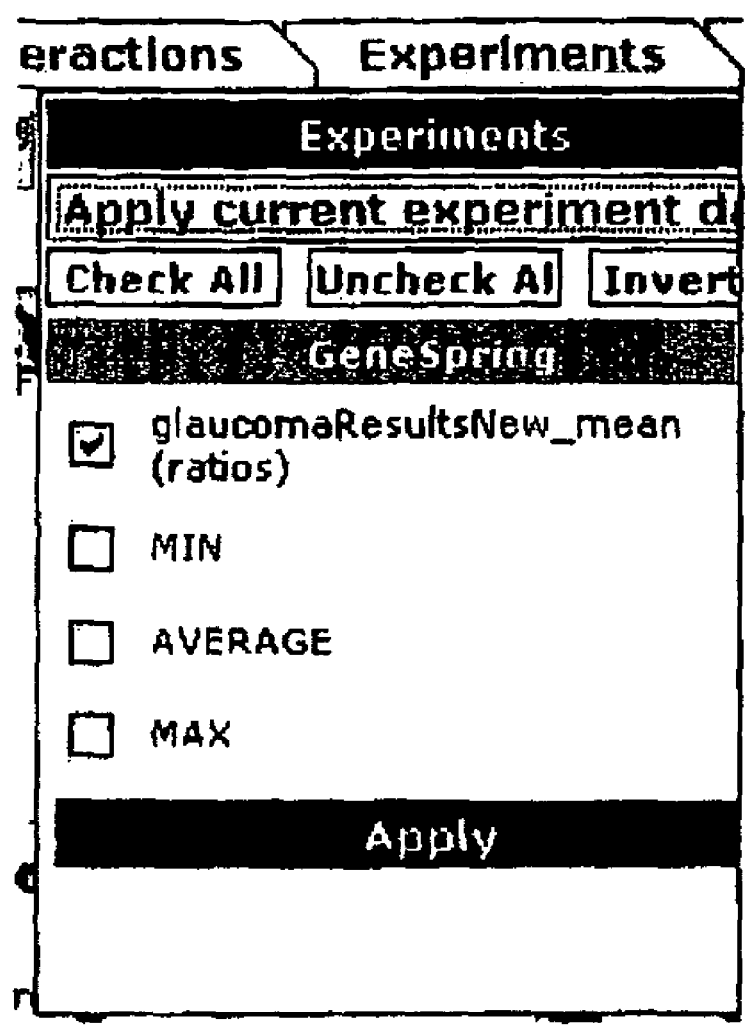
FIG. 47 is a representation of the mapping of data from high-throughput dataset on the initial networks according to one embodiment of the invention.
Figure 48:
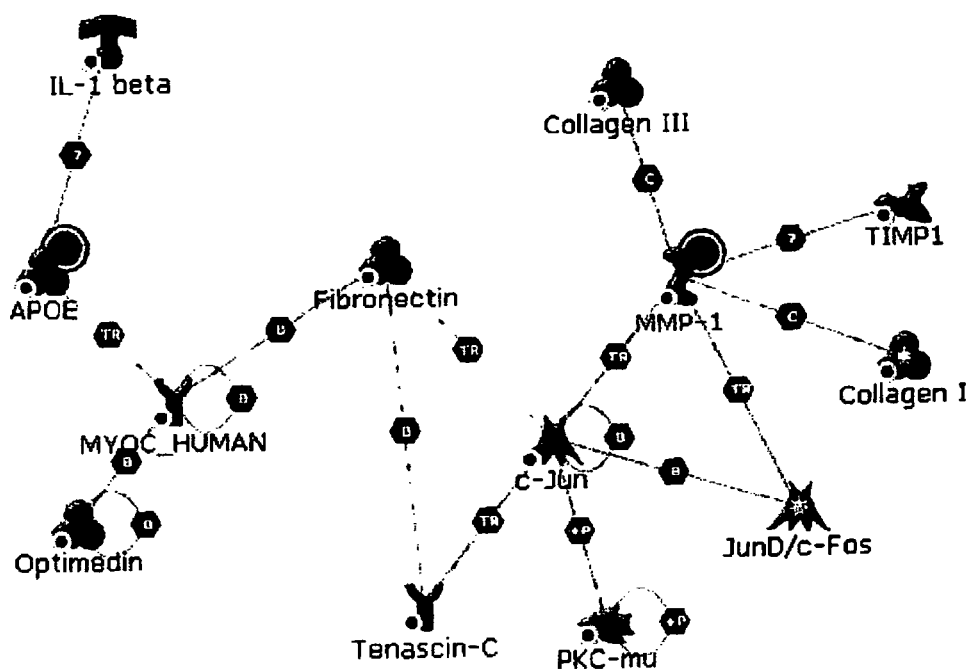
FIG. 48 is a representation of the direct interactions network with the genetics list as root objects according to one embodiment of the invention.

The seed gene lists are uploaded into MetaCore followed by building the initial networks by the standard algorithms in the software (FIGS. 47, 48).

The high-throughput dataset is mapped (superpositioned) on the initial networks by the standard Select Experiments tool in MetaCore as shown on FIG. 47.

The differentially expressed genes (or differentially abundant proteins) are identified on the same networks as the corresponding nodes connected directly or in two steps to the nodes from the seed dataset.

Therefore, the whole list of all high-throughput data is narrowed down to several genes (proteins), most relevant to the seed dataset. The differentially expressed genes connected in one step to the genes from seed list are considered as the most likely candidates for drug targets and molecular biomarkers.

The final list of genes includes the genes from genetics list and the list of over-expressed genes (highly abundant proteins). Direct interactions algorithm is used for building the final network. This network represents the most relevant network for the disease/condition based on the initial three datasets. The over-expressed genes (abundant proteins) on this network are considered as the most likely targets and biomarkers for the disease (condition).

Further network analysis to determine specific implication of the selected genes.

Example 10

Identification of Novel Drug Targets in Glaucoma

As a source of an independent, non-expression dataset, we have compiled a list of 51 genes shown to be associated with glaucoma pathology from small-scale, mostly genetics, experiments (Table 4). We named this dataset as the genetics list. The Direct Interactions algorithm allowed to connect 13 of these genes into a concise network (FIG. 48). The network was statistically significant with p-value of 0.95.

Only six genes of 51 small scale dataset were common with the set of 496 of differentially expressed genes from microarrays: the over-expressed MMP-1, APOE and c-Fos and under-expressed ENPP1, MMP1, and SLC4A4. Such small direct overlap, typical for is not sufficient for any functional interpretation, rather that the gene lists are inconsistent.

On the next step, we identified the differentially expressed genes in the closest interactions proximity to the core of small experiments set as the most relevant set of differentially expressed genes to the small experiments set. The Analyzed Networks algorithm was applied to the small experiments set and the network built. The cluster size was limited to 50 objects, and only highest confidence interactions mechanisms allowed. The resulted networks were sorted based on z-scores (see above) and 20 top networks with z-scores from 38 to 56 chosen for the analysis.

$$\text{score} = \frac{r - 1 - n\frac{R-1}{N}}{\ln(n)}$$

$$z\text{-score} = \frac{r - n\frac{R}{N}}{\sqrt{n\left(\frac{R}{N}\right)\left(1 - \frac{R}{N}\right)\left(1 - \frac{n-1}{N-1}\right)}}$$

Where:

N—total number of nodes in MetaCore database

Figure 49A:
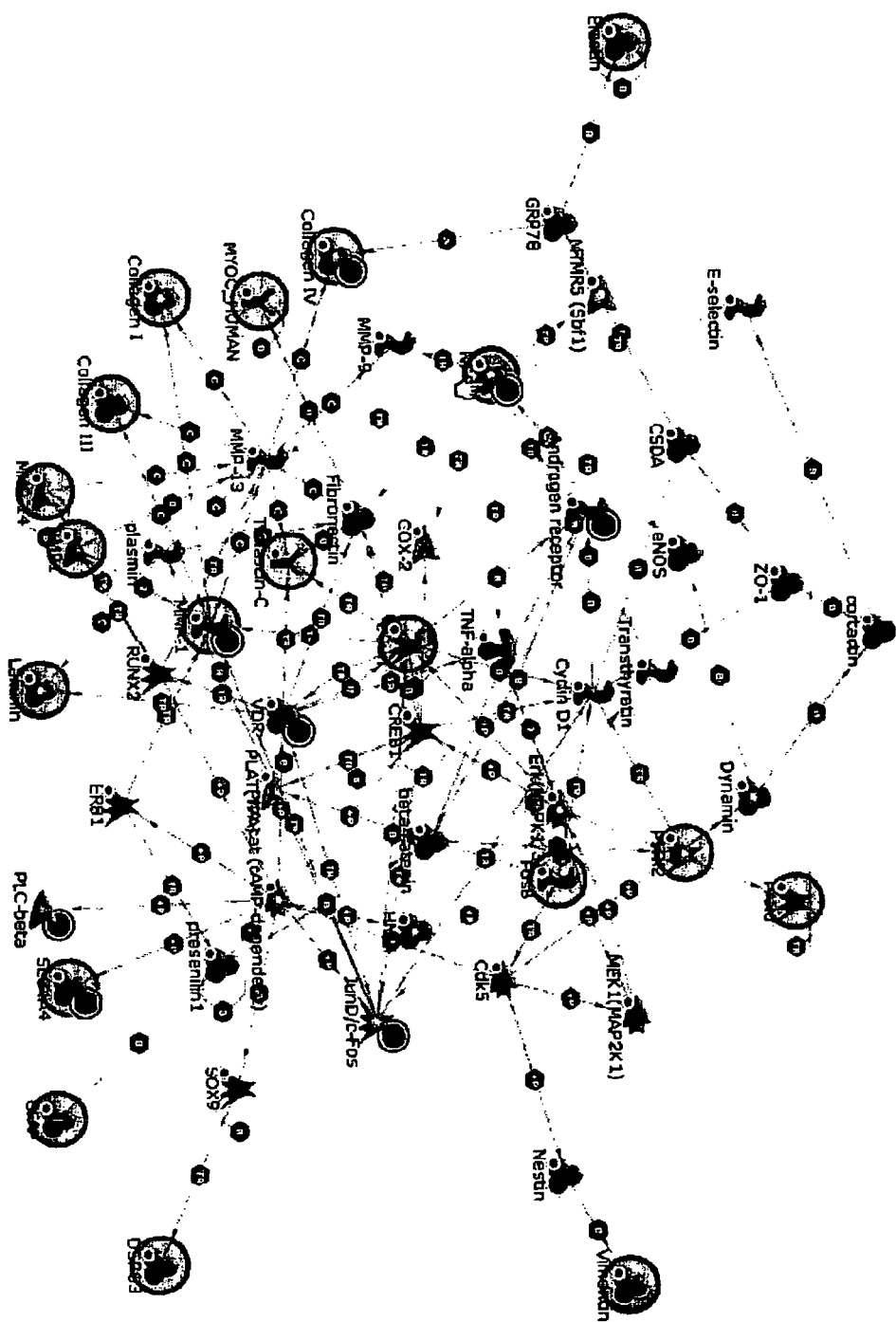
FIG. 49A is a representative diagram showing the highest scored Analyze Networks network according to one embodiment of the invention.
Figure 49B:
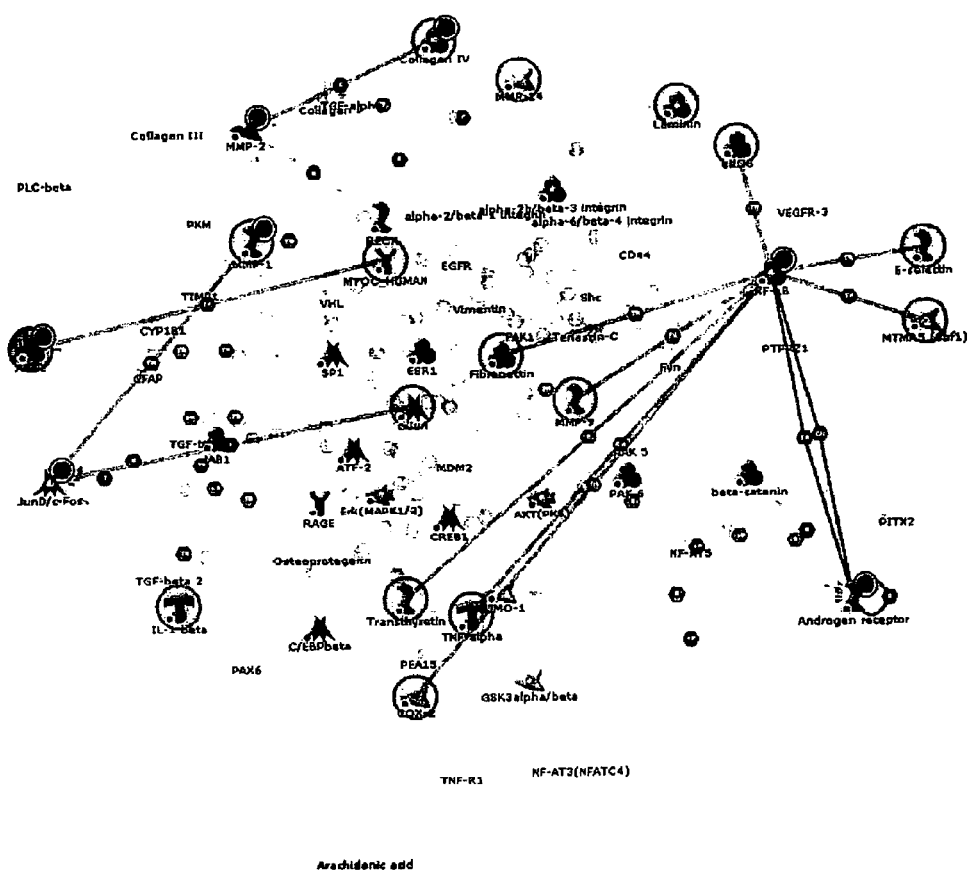
FIG. 49B is a diagrammatic representation of the genes from genetics list directly regulated by the over-expressed in glaucoma genes.

R—number of the network's objects corresponding to the genes and proteins in your list n—total number of nodes in each small network generated from your list r—number of nodes with data in each small network generated from your list The z-scores reflect the relative saturation of the networks with the root objects; in this case with the genes from the genetics list. On each out of top 20 networks, at least 40% of the objects were root objects from the genetics list. The networks included two to six differentially expressed genes, connected with the small experiments genes in one or two steps (FIGS. 49A-B and Table 4, first column). 14 out of 23 over-expressed genes were connected in one step with small set genes (Table 4, third column). NF-kB, vitamin D receptor and androgen receptor had the largest number of one-step interactions with the small experiments nodes: 10, 5 and 4 connections, correspondingly.

TABLE 4

| Genetics List | Over-Expressed Genes | 1-Step Connections | Under-Expressed Genes |
|---|---|---|---|
| PKM | Collagen IV, VI | | STAT1 |
| GFAP | NF-kB | 10 | PLCbeta |
| HSPB7 | | | Protein kinase G |
| c-Fos | c-Fos | 1 | ENPP1 |
| FosB | Andr. Receptor | 4 | Neurogranin |
| JunD/c-Fos | HDL | 2 | PAI1 |
| c-Jun | VDR | 5 | SLC4A4 |
| E-selectin | SPD/SPM | 1 | MAPK8 |
| Fibrillin 1 | ApoE | 1 | MMP1 |
| MMP-1 | MMP2 collagenase | 2 | ETS1 |
| MMP-9 | ENPP2 | | Adenylate cyclase |
| MMP-14 | Fibromodulin | 1 | |
| TIMP1 | IL-8 | | |
| MYOC_HUMAN | Caspase 1 | 1 | |
| PITX2 | MAPK10 | | |
| SPP | C/EBP | | |
| eNOS | EPB41 | | |
| APOE | Clusterin | | |
| Optimedin | Progesterone receptor | 1 | |
| Optineurin | Caspase 4 | | |
| Olfactory receptor | cMyb | 2 | |
| NOE1_HUMAN | Myeloperoxidase | | |
| FoxL2 | Integrin | 1 | |
| TNF-alpha | GNRH-R | 1 | |
| TNF-R1 | NCAM | | |
| TGF-beta 2 | | | |
| ENPP1 | | | |
| CYP1B1 | | | |
| Elastin | | | |
| Tenascin-C | | | |
| Fibronectin | | | |
| Vimentin | | | |
| Laminin | | | |
| Collagen I | | | |
| Collagen IV | | | |
| Collagen III | | | |
| Collagen VI | | | |
| PKC-mu | | | |
| PLC-beta | | | |
| Arachidonic acid | | | |
| CSPG4 (NG2) | | | |
| DSPG3 | | | |
| LMX1B | | | |
| Transthyretin | | | |
| MTMR5 (Sbf1) | | | |
| SLC4A4 | | | |
| ELF5 | | | |
| COX-2 | | | |
| IL1RN | | | |
| IL-1 beta | | | |
| PAX6 | | | |

Figure 50A:
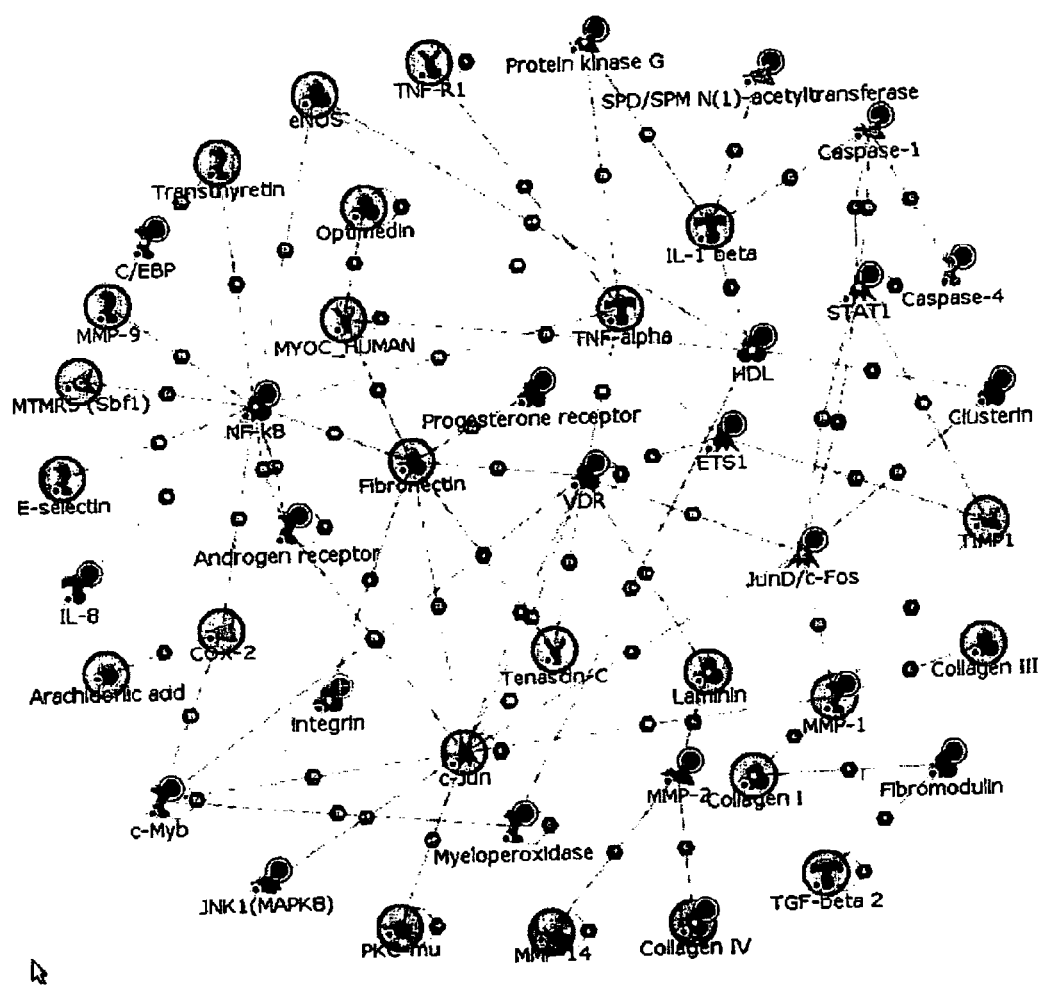
FIG. 50A is a representative diagram showing the final network for genetics list and over-expressed in glaucoma genes (threshold 2.5 fold) built by Direct Interactions algorithm.

In the next step, we combined the genetics list with the list of 32 differentially expressed genes identified at the previous steps. Six genes were common between the lists. The resulted list of 78 genes was used as root objects for building the final Direct Interactions network. A surprising high number of objects, 46 formed one concise network which included 24 nodes from the genetics list, 18 overexpressed genes and 5 down-regulated nodes (FIG. 50A). The top ten cellular GO processes included cell cycle regulation, inflammatory response, proteolysis and induction of apoptosis (FIG. 50B). The main hubs included c-Jun (9 edges), fibronectin (7 edges), MMP-1 (5 edges), TNF-alpha (4 edges), IL-1beta (4 edges), eNOS (3 edges), MYOC (3 edges) from the genetics list; and NF-kB (10 edges), JunD/c-Fos (5 edges), VDR (8 edges), HDL (4 edges), cMyb (4 edges) from over-expressed genes list. (The complete set in Table 4.) We consider this network as the most relevant for the patient's dataset and the genetics association data known up-to-date on glaucoma.

We evaluated the specificity and non-randomness of the final network. First, sets of 78 objects randomly selected from the relevant dataset (the known gene content of Affymetrix microarray recognized at MetaCore networks) were run 500 times as described above. The p-value of the resulted network was 0.99. Second, we added the list of 32 of most highly expressed genes from the dataset to the genetics set and built networks with the same Direct Interactions algorithm. The resultant network contained 15 nodes total, which is non-essentially more than the genetics network itself.

Example 11

Figure 51:
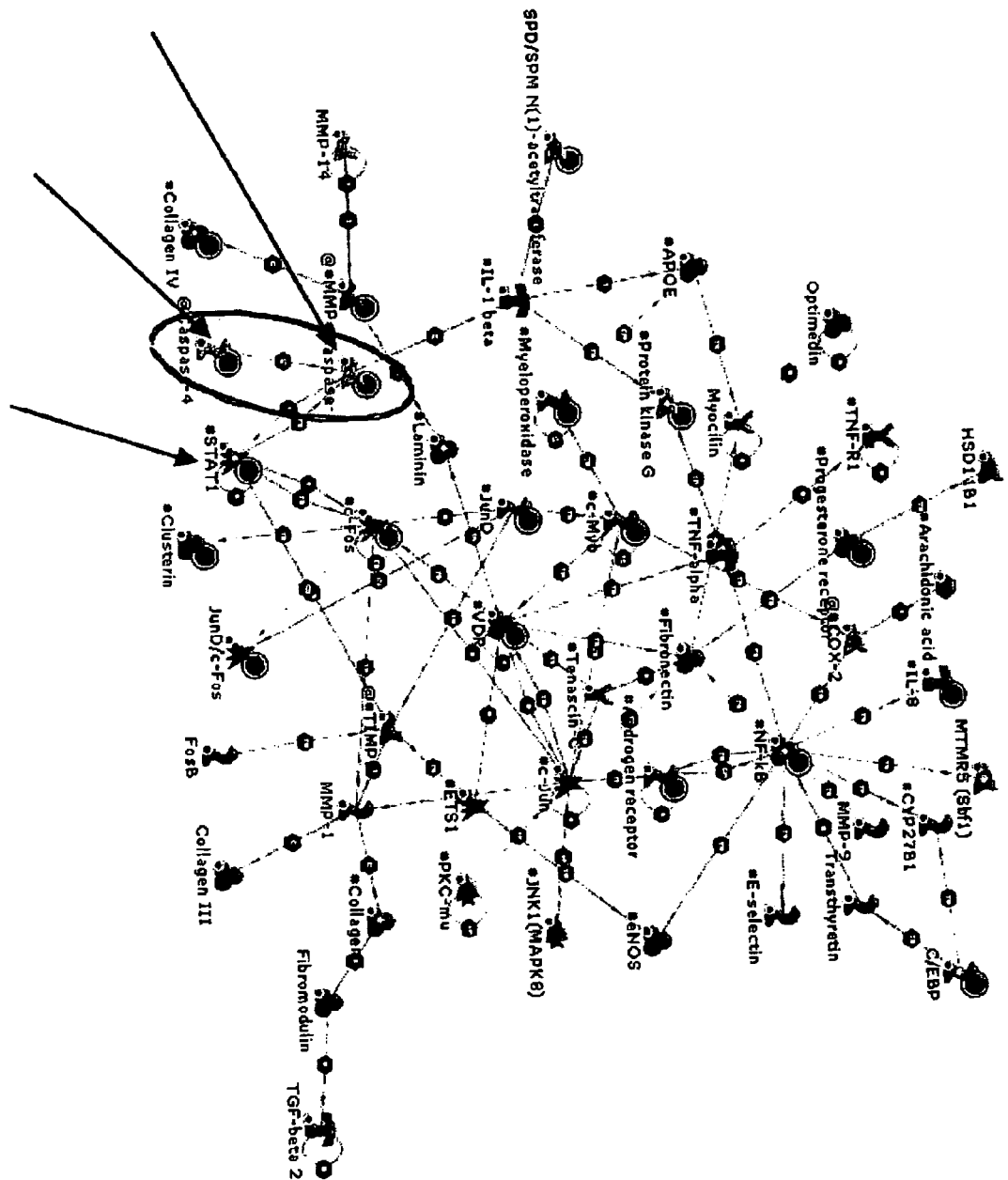
FIG. 51 is a diagrammatic representation of Caspases 1,4 as therapeutic targets.

Potential Drug Targets, Drugs and Preventive Therapy for Glaucoma Based on Network Analysis Small molecules, siRNA and antibody inhibitors of Caspases 1, 4 and 8 may be utilized as therapy for glaucoma. (see FIG. 51). STAT1 is down-regulated in glaucoma. Caspases 1,4, and 8 decrease the amount of STAT1 protein and, therefore, could be a drug targets and are up-regulated in glaucoma. Inhibitors for Caspases 1, 4, and 8 could be used as drugs for glaucoma. STAT1 deficiency is linked to severe encephalopathy and neurodegeneration.

Small molecules, siRNA and protein modulators of human vitamin D receptor may be identified as therapy for glaucoma. Networks show that VDR—vitamin D receptor is connected to and initiates all major hubs on glaucoma-related networks. VDR is over-expressed in glaucoma.

Small molecules, siRNA and antibody inhibitors of MAPK10 kinase may be identified as therapy for glaucoma. MAPK10- map kinase 10- activates AP-1 (c-Jun/c-fos) transcription factor, NF-kb. It is over-expressed in glaucoma.

Figure 52A:
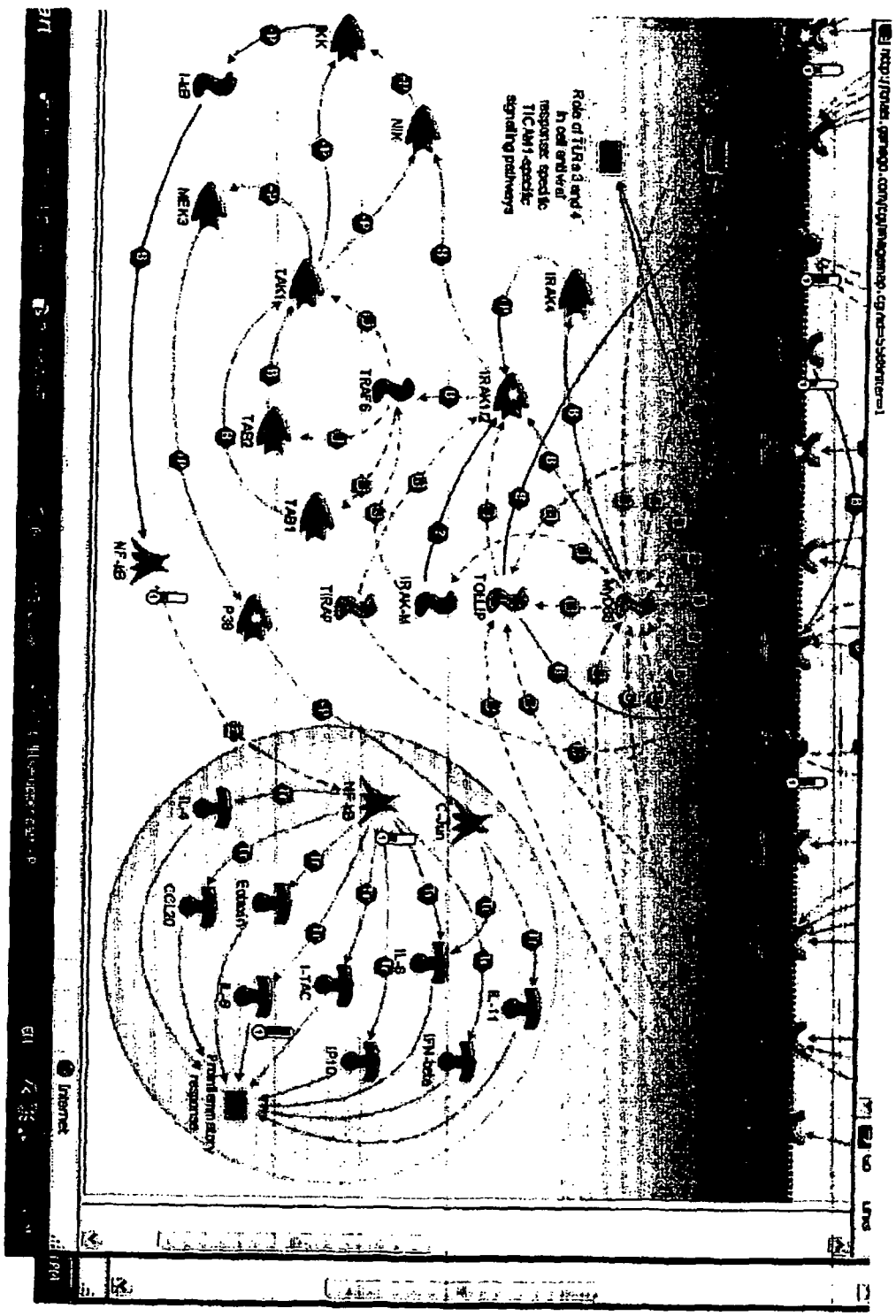
FIG. 52A is a diagrammatic representation of the pathways map for inflammatory response in glaucoma.
Figure 52B:
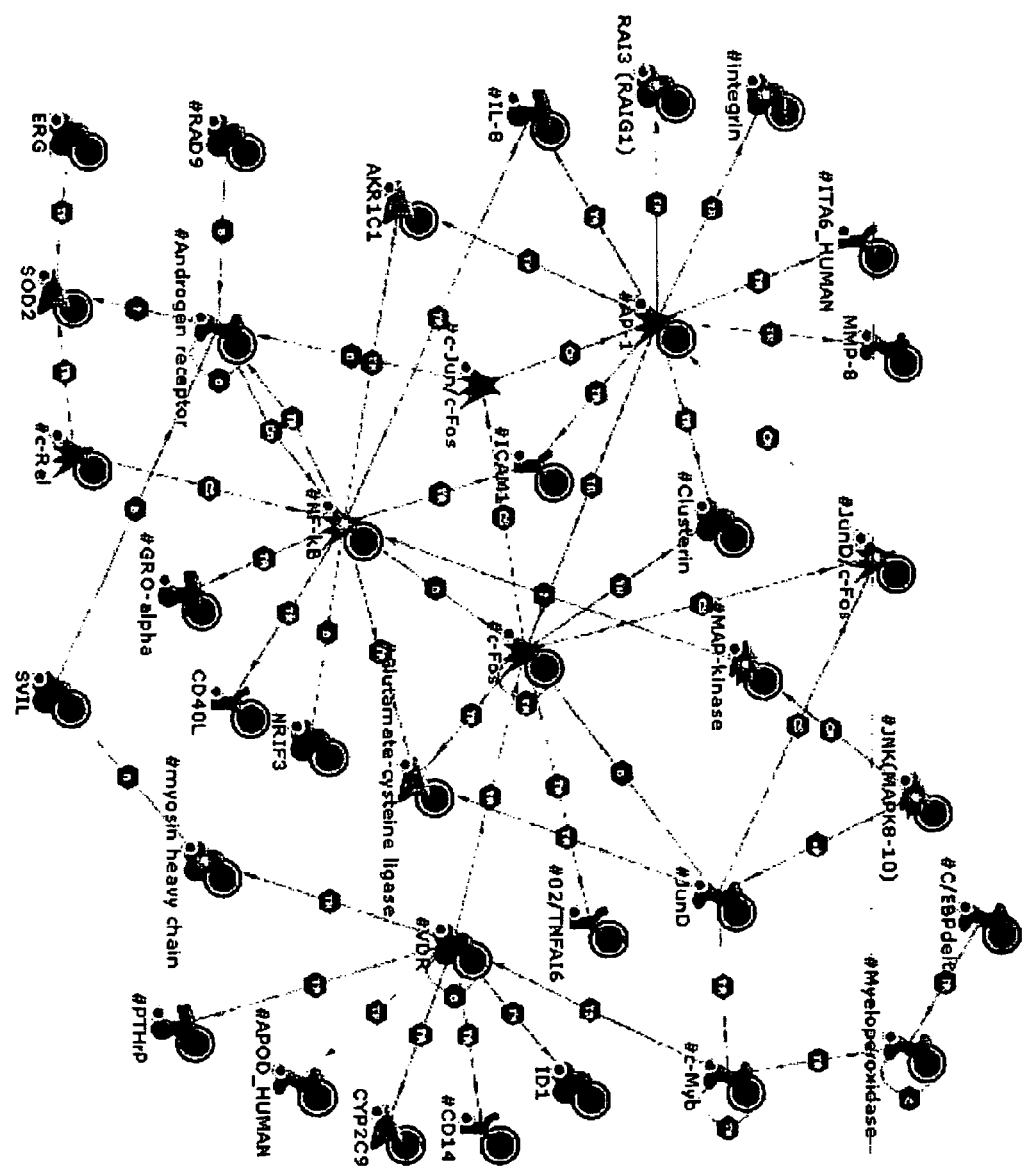
FIG. 52B is a diagrammatic representation of the network for inflammatory response in glaucoma.

Small molecules, siRNA and protein inhibitors of the proteins involved in inflammatory response in glaucoma may be identified such as GRO-alpha, CD40L, Clusterin, CD14, IL-8, Toll-like receptors (TLR1). All of these genes implicated in pro-inflammatory and anti-inflammatory responses are all over-expressed in glaucoma (see FIG. 52).

Figure 53:
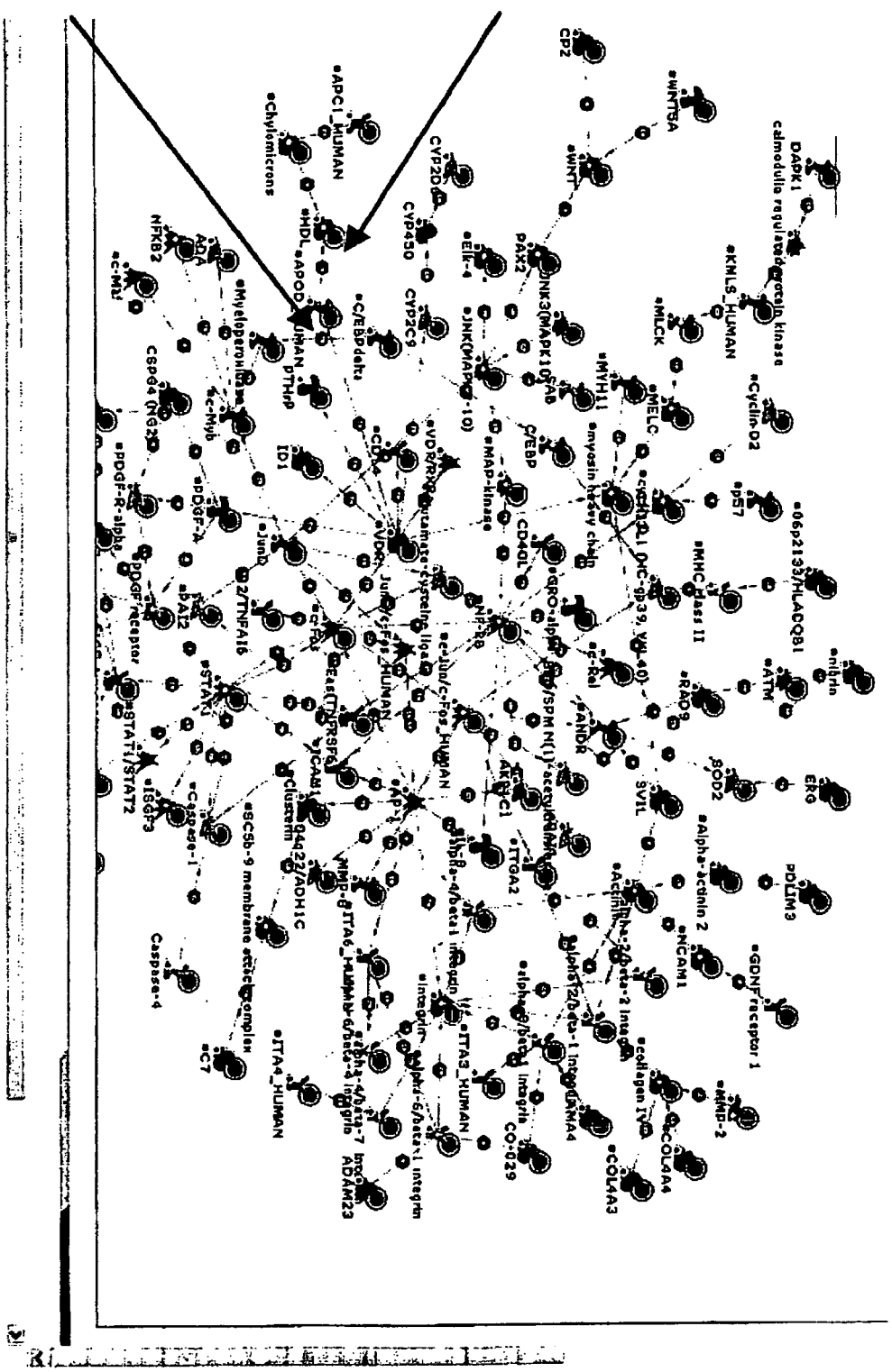
FIG. 53 is a diagrammatic representation of proteins implicated in membrane homeostasis and cell adhesion that are over-expressed in glaucoma.

Small molecules, siRNA and protein modulators for the proteins implicated in membrane homeostasis and cell adhesion APOD, HDL, SVIL, Actinin—all of which are over-expressed in glaucoma and may be identified using the present system (see FIG. 53).

Figure 54:
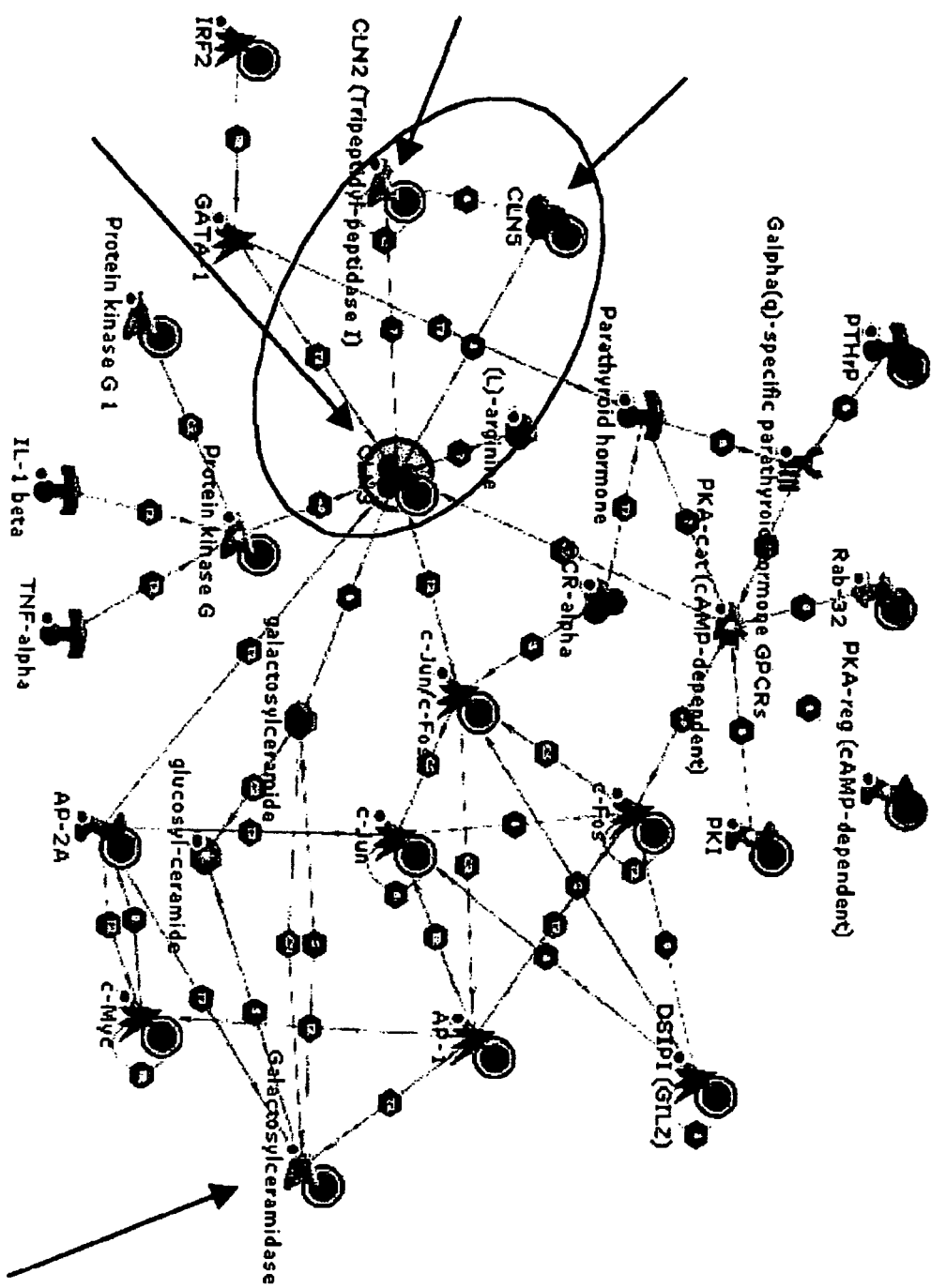
FIG. 54 is a diagrammatic representation of genes involved in hereditary neurodegenerative disorders.

Genes, involved in hereditary neurodegenerative disorders CLN3, CLN2, CLN5 and Galactosylceramidase are all slightly over-expressed in glaucoma (1.5-1.9 times) and small molecules, siRNA or protein inhibitors or modifiers may be identified using the present system (see FIG. 54). Localization is generally lysosomal in this defect.

Defects in CLN3 are a cause of Batten Disease (BD) (also known as juvenile-onset neuronal ceroid lipofuscinosis type 3; JNCL), a recessively inherited neurodegenerative disorder of childhood, characterized by progressive loss of vision, seizures and psychomotor disturbances. Biochemically the disease is characterized by lysosomal accumulation of hydrophobic material, mainly ATP synthase subunit C. Clinical onset is usually from five to ten years of age. No treatment is available and BD is usually fatal within a decade. The incidence is estimated at 1/20000 to 1/100000 live birth, making it one of the most common neurodegenerative diseases of childhood.

Defects in CLN5 are the cause of Finish variant late-infantile neuronal ceroid lipofuscinosis (VLINCL, also known as ceroid lipofuscinosis neuronal 5 (CLN5), a fatal childhood neurodegenerative disease characterized by progressive visual and mental decline, motor disturbance, epilepsy and behavioral changes. The first symptom is motor clumsiness, followed by progressive visual failure, mental and motor deterioration and later by myoclonia and seizures.

Defects in CLN2 are the cause of classical late-infantile neuronal ceroid lipofuscinosis (LINCL), also known as ceroid lipofuscinosis neuronal 2 (CLN2), a fatal childhood neurodegenerative disease characterized by progressive visual and mental decline, motor disturbance, epilepsy and behavioral changes. The three main subtypes of childhood NCLS defined by the age of onset, clinical features and ultrastructural morphology are infantile NCL (INCL), classical late-infantile NCL (LINCL), or juvenile NCL (JNCL), although a number of other distinct variant forms have been described. Catalytic activity occurs with the release of an N-terminal tripeptide from a polypeptide. Detected in all tissues examined with highest levels in heart and placenta and relatively similar levels in other tissues.

Defects in GALC in the brain are the cause of globoid cell leukodystrophy (GLD, or Krabbe disease). This autosomal recessive disorder deficiency results in the insufficient catabolism of several galactolipids that are important in the production of myelin. Clinically the most frequent form is the infantile form. Most patients (90%) present before six months of age with irritability, spasticity, arrest of motor and mental development, and bouts of temperature elevation without infection. This is followed by myoclonic jerks of the arms and legs, oposthotonus, hypertonic fits and mental regression which progresses to a severe decerebrate condition with no voluntary movements and death from respiratory infections or cerebral hyperpyrexia before two years of age. However, a significant number of cases with later onset, presenting with unexplained blindness, weakness, and/or progressive motor and sensory neuropathy that can progress to severe mental incapacity and death, have been identified.

Defects in GALC in skin fibroblasts, which belongs to family 59 of glycosyl hydrolases show the highest level of activity in testes compare to brain, kidney, placenta, and liver and can also be found in urine.

In the testes galactosylceramidase hydrolyzes the galactose ester bonds of galactosylceramide, galactosylsphingosine, lactosylceramide, and monogalactosyldiglyceride. It is an enzyme with very low activity responsible for the lysosomal catabolism of galactosylceramide, a major lipid in myelin, kidney and epithelial cells of the small intestine and colon. It has an optimal pH between 4.0 and 4.4. Activity is lost when heated at 52 degrees Celsius for five minutes.

In the placenta two forms of galactosylceramidase are produced by alternative splicing.

Example 12

Hormone Therapy in Glaucoma

Individual or combined application of parathyroid hormone, androgen, estrogen and progesterone may be utilized to treat glaucoma. PTHrP may play a protective role in glaucoma.

Androgen, estrogen and progesterone should play protective role in glaucoma. ANDR, ESTR and progesterone receptors are significantly up-regulated protective role in glaucoma.

TABLE 5

| Name | Description | URL address |
|---|---|---|
| Protein Interaction Databases | | |
| BIND | A curated database of interactions, derived both from the literature and experimental datasets. 8,500 interactions are deduced from high-confidence small scale experiments from multiple species. BIND can be used for querying and as a browser. | bind.ca |
| DIP | A database of experimentally determined protein-protein interactions, mostly from yeast. About 10% of DIP interactions are derived from high confidence small scale experiments. | dip.doe-mbi.ucla.edu/ |
| HPRD | Hunan Protein Reference Database provides curated human-specific protein interactions; currently over 22,000 interactions for over 10,000 human proteins. It also contains 7 signaling maps. HPRD is used as a browser for interactions, protein annotations, motifs and domains. | www.hprd.org/ |
| MetaCore database | A manually curated interactions database for over 90% human proteins with known function. Content of MetaCore (see below). | www.genego.com. |
| MINT and HomoMINT | A searchable interaction database with total of 40,000 interactions, mostly from yeast and fly. 70% interactions are from lower-confidence Y2H screens. Only 3800 interactions include human proteins. | mint.bio.uniroma2.it/mint/ |
| MIPS | A well-known searchable database on high-quality small scale experiments protein-protein interactions in yeast (65) and most recently mammals. Several hundred human interactions. | mips.gsf.de |
| PathArt database | A manually curated database of about 7,500 protein-protein and protein-compound interactions and pathways. Content of PathArt (see below). | jubilantbiosys.com |
| Pathway Analysis database | The mammalian interactions content of Pathway Analyst (see below). The number of interactions is not announced. | www.ingenuity.com |
| STRING | A database of known and predicted protein interactions deduced from over 110 genomes, high-throughput experiments and gene co-expression. | string.embl.de |
| Pathways Maps and Process Ontologies | | |
| BIOCarta | A commercial collection of about 350 maps on human biology representing canonical pathways. | www.biocarta.com/genes/index.asp |
| Gene Ontology | The most often referred to publicly available protein classification based on cellular processes developed by Gene Ontology Consortium. | www.geneontology.org |
| GenMAPP | Gene MicroArray Pathway Profiler is a database of GO-derived diagrams designed for viewing and analyzing gene expression data. | www.genmapp.org |
| KEGG | A well known database of generic metabolic maps for bacteria and eukaryotes. Recently added some regulation maps. Software allows comparison of genome maps, graph comparison and path computation. | www.genome.jp/kegg/pathway.html |
| MetaCore, pathway module | A part of the commercial tool MetaCore™. The pathways module contains 350 interactive maps for >2,000 established pathways in human signaling, regulation and metabolism. HT data can be superimposed on the maps and networks built for any object. | www.genego.com |
| Protein Lounge | A commercial package with about 300 human metabolic and signaling maps. | www.proteinlounge.com |
| Network Data Mining Suites | | |
| MetaCore/ MetaDrug, GeneGo, Inc. | An integrated analytical suite based on a manually curated database of human protein-protein and protein-DNA interactions. All types of HT data can be used for building networks. Medicinal chemistry module allows predicting human metabolism and toxicity for novel compounds. Networks are connected to functional processes, 350 proprietary metabolic and signaling maps. Web access or enterprise solution. | www.genego.com |
| Pathway Analyst, Ingenuity, Inc. | An integrated analytical suite based on a manually curated database of literature-derived mammalian protein-protein interactions. Visualization on networks and analysis of HT data. Networks are connected to GO processes, 60 KEGG metabolic maps and Cell Signaling Inc.'s signaling maps. Web access, enterprise solution. | www.ingenuity.com |

TABLE 5-continued

| Name | Description | URL address |
| --- | --- | --- |
| PathArt, Jubilant Biosystems | A curated database of generic protein interactions, pathways and bioactive molecules supported by HT data parsers and visualization tools. Connectivity with ligand databases, GO categories. Web access. | www.jubilantbiosys.com/pd.htm |
| Pathway Assist, Ariadne Genomics | A software tool for mapping the HT data on networks, maps and pathways. The source of interactions data is NLP mining of PubMed abstracts. PathwayAssist is bundled with Jubilant and Integrated Genomics pathways content. A desktop product. | ariadnegenomics.com |

Having thus described several aspects of at least one embodiment of this invention, it is to be appreciated that various alterations, modifications and improvements will readily occur to those skilled in the art. Such alterations, modifications, and improvements are intended to be part of this disclosure, and are intended to be within the spirit and scope of the invention.

What is claimed is:

1. A method for identifying a human drug or gene therapy target, said method comprising:
   a) collecting metabolic data for a non-disease state and a disease state;
   b) linking the data into at least two metabolic pathways using a relational database;
   c) ranking the metabolic pathways based on their relevance to human metabolism, wherein the ranking of the metabolic pathways comprises assigning each pathway to one of the following categories, from the most relevant to the least relevant to human metabolism:
      (i) a multi-step pathway wherein all of the reactions are catalyzed by known human enzymes and/or enzymes that have open reading frame (ORF) candidates in the human genome;
      (ii) a multi-step pathway wherein only the first and last reactions are catalyzed by known human enzymes and/or enzymes that have ORF candidates in the human genome;
      (iii) a multi-step pathway wherein only an intermediate reaction is catalyzed by an identified human enzyme or an enzyme that has an ORF candidate in the human genome; and
      (iv) a multi-step pathway wherein none of the reactions are catalyzed by identified human enzymes or enzymes that have ORF candidates in the human genome;
   d) generating structured annotations of the ranked metabolic pathways;
   e) identifying interconnections between the ranked and annotated metabolic pathways;
   f) reconstructing human metabolism by integrating information obtained in steps a) to e); and
   g) identifying a human drug or gene therapy target by comparing differences between the non-disease and disease states using the reconstruction of step (f).

2. The method according to claim 1, wherein the metabolic data comprise a list of genes associated with the onset of the disease state.

3. The method according to claim 1, wherein the metabolic data comprise a list of genes that are over- or under-expressed in the disease state relative to the non-disease state.

4. The method according to claim 1, wherein the metabolic data are selected from the group consisting of enzymes, proteins, and metabolites.

5. The method of claim 1, wherein the generation of structured annotations of the ranked metabolic pathways comprises:
   a) comparing the ranked metabolic pathways to published information;
   b) confirming, modifying or rejecting the ranked metabolic pathways based on their differences from the published information; and
   c) describing the ranked pathways as a hierarchy of biochemical units.

6. The method of claim 5, wherein the biochemical units comprise a ranked metabolic pathway, metabolic steps that constitute the pathway, chemical compounds, reactions and/or enzymatic functions.

7. The method of claim 6, wherein the enzymatic functions comprise genes and proteins.

8. The method of claim 6, wherein each of the biochemical units is linked to an annotation table.

9. The method of claim 8, wherein the annotation table comprises a field selected from the group consisting of organ localization, tissue localization, intracellular localization, intracellular compartmentalization, subcellular localization in another organism, a relationship to a disease, and a reference to an information source.

* * * * *